United States Patent
Lancaster et al.

(10) Patent No.: US 12,410,407 B2
(45) Date of Patent: Sep. 9, 2025

(54) CHOROID PLEXUS ORGANOIDS AND METHODS FOR PRODUCTION THEREOF

(71) Applicant: UNITED KINGDOM RESEARCH AND INNOVATION, Swindon (GB)

(72) Inventors: Madeline A. Lancaster, Cambridge (GB); Laura Pellegrini, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 782 days.

(21) Appl. No.: 17/425,043

(22) PCT Filed: Jan. 23, 2020

(86) PCT No.: PCT/EP2020/051631
§ 371 (c)(1),
(2) Date: Jul. 22, 2021

(87) PCT Pub. No.: WO2020/152272
PCT Pub. Date: Jul. 30, 2020

(65) Prior Publication Data
US 2022/0106571 A1     Apr. 7, 2022

(30) Foreign Application Priority Data
Jan. 23, 2019 (GB) ..................... 1900930

(51) Int. Cl.
C12N 5/071 (2010.01)
G01N 33/50 (2006.01)

(52) U.S. Cl.
CPC ....... C12N 5/0697 (2013.01); G01N 33/5082 (2013.01); *C12N 2501/155* (2013.01); *C12N 2501/415* (2013.01); *C12N 2506/02* (2013.01)

(58) Field of Classification Search
CPC .......................... C12N 5/0697; C12N 2502/08
See application file for complete search history.

(56) References Cited

U.S. PATENT DOCUMENTS

2016/0289635 A1 * 10/2016 Sasai .................... C12N 5/0619
2018/0030409 A1    2/2018 Lewis et al.

FOREIGN PATENT DOCUMENTS

CN         108853589 A     11/2018

OTHER PUBLICATIONS

Lun et al., Development and functions of the choroid plexus-cerebrospinal fluid system, 2015, Nature Reviews Neuroscience, 16: 445-457 (Year: 2015).*
Eiraku et al. "Self-organized formation of polarized cortical tissues from ESCs and its active manipulation by extrinsic signals." Cell Stem Cell 3(5): 519-532 (2008).
Erb et al. "Review of functional in vitro models of the blood-cerebrospinal fluid barrier in leukaemia research." Journal of Neuroscience Methods 329: 108478 pp. 1-9 (2020).
Lancaster et al. "Guided self-organization and cortical plate formation in human brain organoids." Nature Biotechnology 35(7): 659-666 (2017).
Marsoner et al. "Cortical organoids: why all this hype?." Current Opinion in Genetics & Development 52: 22-28 (2018).
Sakaguchi et al. "Generation of functional hippocampal neurons from self-organizing human embryonic stem cell-derived dorsomedial telencephalic tissue." Nature Communications 6(1): 1-11 (2015).
CN Search Report for Application No. 2020800229029, dated Feb. 23, 2024 (6 pages).
Masters et al. "Sequential emergence and contraction of epithelial subtypes in the prenatal human choroid plexus revealed by a stem cell model." bioRxiv: Jun. 2024 (2024).
Renner et al. "Self-organized developmental patterning and differentiation in cerebral organoids." The EMBO journal 36.10: 1316-1329 (2017).
Lancaster et al. "Generation of Cerebral Organoids from Human Pluripotent Stem Cells." Nat Protoc 9(10): 2329-2340 (2014).

* cited by examiner

*Primary Examiner* — Marcia S Noble
(74) *Attorney, Agent, or Firm* — Nixon Peabody LLP; David S. Resnick; Nicole D. Kling

(57) ABSTRACT

Methods and materials relating to cultured choroid plexus organoids comprising: (a) an epithelium comprising a tight epithelial barrier; and/or (b) one or more cysts surrounded by an epithelium, plus other authentic features and markers.

7 Claims, 28 Drawing Sheets

Specification includes a Sequence Listing.

CHOROID PLEXUS ORGANOIDS AND METHODS FOR PRODUCTION THEREOF

CROSS-REFERENCE TO RELATED APPLICATIONS

This application is a 35 U.S.C. § 371 National Phase Entry Application of International Application No. PCT/EP2020/051631 filed Jan. 23, 2020, which designates the U.S. and claims benefit under 35 U.S.C. § 119(a) of G.B. Provisional Application No. 1900930.7 filed Jan. 23, 2019, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 31, 2021, is named 062915-190310USPX_SL.txt and is 3,929 bytes in size.

FIELD OF THE INVENTION

The present invention relates to choroid plexus organoids, in particular choroid plexus organoids that comprise a tight epithelial barrier and which are capable of producing a cerebrospinal fluid-like liquid. The invention also relates to methods for the production of the choroid plexus organoids.

BACKGROUND TO THE INVENTION

The choroid plexus is a highly conserved and understudied secretory tissue in the brain. This tissue is enlarged in humans proportionately to our brain size and displays a number of important functions in the brain, such as forming a protective epithelial barrier and secreting the cerebrospinal fluid (CSF)(1).

Anatomically, the choroid plexus is localised in the lateral, third and fourth ventricles emerging in each respective lumen. The mature choroid plexus is composed of a single cuboidal epithelium, surrounding a core of mesenchyme-derived stromal tissue and fenestrated capillaries. The epithelial cells are closely connected with tight junctions and highly polarised with an apical brush border facing the lumen of the ventricle and a basal surface on the stromal side.

The highly polarised, secretory epithelium of the choroid plexus displays a number of important functions in the brain, such as forming a protective epithelial barrier and secreting the CSF.

The CSF is important for the maintenance of physiological levels of nutrients in the brain, for the transport of signalling molecules and growth factors, and for its protective role in the regulation of intracranial pressure. The CSF is a clear, colourless fluid that circulates through the ventricles of the brain and the subarachnoid spaces, and is then partly reabsorbed into the blood circulation through arachnoid granulations (2-4).

The CSF is produced by active secretion from the choroid plexus epithelial cells, which maximise the number of transporters and pumps in their apical brush border, and from filtration of blood granted by the presence of tight junctions within the epithelial cells. The choroid plexus has a key role in maintaining the rates of production and reabsorption of CSF. Disturbances of this equilibrium lead to pathologies such as hydrocephalus.

There are different mechanisms involved in CSF production. First, the $Na^+$—$K^+$ ATPase pumps, located on the apical side of choroid plexus epithelial cells, and the cytoplasmic carbonic anhydrase generate an osmotic gradient mainly driven by secretion of $Na^+$ into the lumen of the ventricle. This osmotic force drives transcellular water influx through aquaporin channels. Second, ATP-binding cassette (ABC) proteins and solute carrier transporters (SLCs) allow the exchange of amino acids, nucleosides and small peptides with and without the requirement of ATP hydrolysis, respectively. The choroid plexus epithelial cells also express efflux transporters, such as MRP1 and MRP4. These pumps regulate the clearance of metabolites, and prevent entry of drugs and toxic compounds, thus reducing their availability in the CSF. Third, the highly specialised and expanded secretory system of choroid plexus epithelial cells enables more complex protein and hormone secretion. For example, transthyretin (TTR), a carrier of thyroid hormones and retinol, is the most abundant protein synthesised and secreted by the choroid plexus (Li, X. and Buxbaum, J. N. (2011) Mol. Neurodegener. 6: 1-17; Richardson, S. J. et al. (2015) Front. Neurosci. 9: 1-8; Johnson, B. A. et al. (2018) Fluids Barriers CNS 15: 22). TTR-mediated delivery of thyroid hormones to the CSF appears to have an important role in regulation of brain development.

The choroid plexus tightly sealed epithelium is also known as the blood-CSF barrier (B-CSF-B). The B-CSF-B, similar to the blood-brain barrier (BBB), prevents toxic substances or signals in the circulation from reaching the brain. However, in contrast to the BBB, the B-CSF-B is formed by a single cell type, the choroid plexus epithelial cells, and it faces the CSF rather than the brain parenchyma directly (5, 6). However, because the CSF has free access to the brain, transport of molecules across the B-CSF-B is an alternative route into the brain.

Little is known about choroid plexus human development. The development of choroid plexus follows a series of stages from a pseudostratified epithelium, to a columnar and then highly folded cuboidal epithelium with microvilli and basally located nuclei at the latest stages. In the dorsal telencephalon, around the $7^{th}$ week of gestation, the local BMP signalling gradient drives choroid plexus development from the neuroepithelium, which begins to elongate towards the lumen of the ventricle. By establishing local thresholds, the BMP secreted signals gradually specify the choroid plexus epithelium and the adjacent cortical hem, a Wingless-related (WNT) signalling centre from which the hippocampal primordium develops.

Studies toward the patterning of choroid plexus have been carried out in vitro. Over the past decade, significant progress in 3D culture systems such as cerebral organoids has allowed fundamental discoveries in human developmental biology (7-12).

However, the induced choroid plexus cells generated so far have not been shown to exhibit the same complex architecture as the in vivo choroid plexus, nor have they been shown to be functional in generating CSF.

Accordingly, there remains a significant need in the art for the establishment of functional models of the choroid plexus. The choroid plexus is an important point of entry of drugs to the CNS; however, little is known about the regulation and permeability of the B-CSF-B and how it could be exploited as a tool to improve the availability of certain drugs in the brain.

The study of functional models of the choroid plexus may aid understanding in this regard, in particular for assaying candidate drugs for the ability to cross the B-CSF-B and/or BBB.

SUMMARY OF THE INVENTION

The inventors have established a protocol to generate choroid plexus organoids using a combination of signalling molecules.

The organoids (which may be referred to hereinafter as "ChP organoids") have a selective epithelial barrier that secrete CSF-like fluid in self-contained compartments, much like the CSF of brain ventricles. Characterization of ChP organoids by single cell RNA sequencing reveals the presence of epithelial and stromal ChP populations. Proteomic analysis of the organoid CSF-like fluid reveals human-specific and developmental factors, as well as disease-related biomarkers. Finally, using NMR the inventors show that this in vitro barrier exhibits the same selectivity to small molecules as the in vivo counterpart, and that ChP-CSF organoids can predict CNS permeability of novel compounds.

Thus, the organoids provided by the inventors' protocol recapitulate fundamental functions of the choroid plexus, namely secretion and formation of a tight epithelial barrier. The inventors determined that the organoids provided by their protocol reliably and reproducibly develop choroid plexus epithelium with polarised cells that actively secrete a fluid within the organoid with properties closely resembling cerebrospinal fluid (CSF).

Furthermore, the inventors discovered the presence of choroid plexus-specific water channels and transporters localised on the apical brush border of the choroid plexus organoid epithelium using histological and electron microscopy (EM) analysis. These tissues were found to display tight junctions forming the epithelial barrier, and the inventors observed the formation of large fluid-filled cysts protruding from the organoids, the contents of which, analysed by mass spectrometry, highly resemble human embryonic CSF.

The invention provides a tool to study, for example, choroid plexus function, CSF production, and the permeability of compounds, peptides and serum-derived proteins into the human brain through the CSF.

Accordingly, in one aspect the invention provides a choroid plexus organoid comprising: (a) an epithelium comprising a tight epithelial barrier; and/or (b) one or more cysts surrounded by an epithelium.

In some embodiments, the choroid plexus organoid comprises an epithelium comprising a tight epithelial barrier. In some embodiments, the choroid plexus organoid comprises one or more cysts surrounded by an epithelium. In preferred embodiments, the choroid plexus organoid comprises an epithelium comprising a tight epithelial barrier and one or more cysts surrounded by the epithelium.

In preferred embodiments, the epithelium is cuboidal epithelium.

In some embodiments the choroid plexus organoid further comprises (c) stromal cell populations.

In some embodiments the choroid plexus organoid has a lateral ventricle identity.

In preferred embodiments, the choroid plexus organoid is LUM+, DCN+, and DLK1+.

In some embodiments, the choroid plexus organoid is TTR+, MRP1+, Aqp1+ and/or ZO1+.

In preferred embodiments, the choroid plexus organoid is TTR+, MRP1+, Aqp1+ and ZO1+.

In other embodiments, the choroid plexus organoid is TTR+, MRP1+, MRP4+, Aqp1+ and/or ZO1+. In other embodiments, the choroid plexus organoid is TTR+, MRP1+, MRP4+, Aqp1+ and ZO1+.

In some embodiments, the choroid plexus organoid comprises at least 50% TTR+ tissue. In some embodiments, the choroid plexus organoid comprises at least 60% TTR+ tissue. In some embodiments, the choroid plexus organoid comprises at least 70% TTR+ tissue. In some embodiments, the choroid plexus organoid comprises at least 80% TTR+ tissue. In some embodiments, the choroid plexus organoid comprises at least 90% TTR+ tissue.

In some embodiments, the epithelium is TTR+, MRP1+, Aqp1+ and/or ZO1+. In preferred embodiments, the epithelium is TTR+, MRP1+, Aqp1+ and ZO1+.

In some embodiments, the epithelium is MRP4+.

In some embodiments, the TTR is enriched on the apical side of the epithelium. In some embodiments, the Aqp1 is enriched on the apical side of the epithelium. In some embodiments, the ZO1 is enriched on the apical side of the epithelium.

In some embodiments, the TTR and Aqp1 are enriched on the apical side of the epithelium.

In some embodiments, the TTR, Aqp1 and ZO1 are enriched on the apical side of the epithelium.

In some embodiments, the MRP1 is enriched on the apical and basal sides of the epithelium.

In some embodiments, the MRP4 is enriched on the apical and basal sides of the epithelium.

Enrichment of a marker in a certain area, for example of a cell, may mean that the marker is present in that area in greater abundance than other areas (e.g. all other areas). The marker may be substantially absent in other areas (e.g. all other areas).

In some embodiments, the choroid plexus organoid is FOXG1−.

In some embodiments, the epithelium comprises apical microvilli.

In some embodiments, the epithelium comprises centro-basally located nuclei.

In some embodiments, the epithelium is apico-basal polarised.

In some embodiments, the epithelium is polarised, and Aqp1 and ZO1 are expressed on the luminal side of the epithelium.

In some embodiments, LAT-1 is expressed on the apical side of the epithelium.

In some embodiments, the epithelia are enriched in specific transporters involved in the trafficking of nutrients e.g. SLC23A2 (vitamin C) and/or SLC46A2 (folate). In some embodiments, the choroid plexus organoid is capable of secreting a liquid comprising one or more proteins selected from the group consisting of transthyretin (TTR), clusterin (CLU), apolipoprotein E (APOE), apolipoprotein A4 (APOA4) and lumican (LUM).

In some embodiments, the liquid comprises phospholipid transfer protein (PLTP)

In some embodiments, the liquid comprises alphafetoprotein (AFP).

In some embodiments, the choroid plexus organoid is capable of secreting a cerebrospinal fluid (CSF)-like fluid.

In some embodiments, the choroid plexus organoid is capable of secreting a cerebrospinal fluid (CSF).

In preferred embodiments, the cysts comprise a liquid. In preferred embodiments, the liquid comprises one or more proteins selected from the group consisting of transthyretin (TTR), clusterin (CLU), apolipoprotein E (APOE), apolipoprotein A4 (APOA4) and lumican (LUM). In some embodiments, the liquid is a CSF.

In some embodiments, the liquid comprises alphafetoprotein (AFP).

In some embodiments, the liquid comprises developmental-specific CSF proteins e.g. Insulin-like growth factor 2 (IGF2), IGFBP7, and/or Follistatin-like protein 1 (FSTL1).

In some embodiments, the choroid plexus organoid comprises less than 25%, 20%, 15%, 10%, 5%, 4%, 3%, 2% or 1% (v/v) forebrain neuronal tissue. In some embodiments, the choroid plexus organoid comprises substantially no forebrain neuronal tissue.

In some embodiments, the choroid plexus organoid comprises less than 25%, 20%, 15%, 10%, 5%, 4%, 3%, 2% or 1% (v/v) FOXG1+ tissue. In some embodiments, the choroid plexus organoid comprises substantially no FOXG1+ tissue.

In some embodiments, the choroid plexus organoid comprises extracellular matrix (ECM).

In some embodiments, the choroid plexus organoid have primary cilia, for example, with microvilli apically located, tight junctions between cells, multi-vesicular bodies and extracellular vesicles.

In some embodiments, the choroid plexus organoid is a human or mouse organoid, preferably a human organoid.

In some embodiments, the choroid plexus organoid is obtainable by the method of the invention.

In some embodiments, the choroid plexus organoid is produced from stem cells, optionally embryonic stem cells or induced pluripotent stem cells.

In another aspect, the invention provides use of a WNT pathway activator and a bone morphogenetic protein (BMP) signalling pathway activator for producing a choroid plexus organoid, wherein the choroid plexus organoid comprises (a) an epithelium comprising a tight epithelial barrier; and/or (b) one or more cysts surrounded by an epithelium.

Although there are previous reports of using Bmp4 and/or CHIR (see (15) and (16)) these earlier publications did not yield ChP organoids having the authentic characteristics demonstrated herein.

In another aspect, the invention provides a method for producing a choroid plexus organoid comprising contacting a population of neuroepithelial cells with a WNT pathway activator and a bone morphogenetic protein (BMP) signalling pathway activator, wherein the choroid plexus organoid comprises: (a) an epithelium comprising a tight epithelial barrier; and/or (b) one or more cysts surrounded by an epithelium.

The method may be performed with or without fibrous microscaffolds. The absence of microscaffolds may be preferred.

In another aspect, the invention provides a method for producing a choroid plexus organoid comprising producing a population of neuroepithelial cells from a population of stem cells, and culturing the population of neuroepithelial cells in the presence of a WNT pathway activator and a bone morphogenetic protein (BMP) signalling pathway activator.

In preferred embodiments, the population of neuroepithelial cells is an aggregate of neuroepithelial cells.

In preferred embodiments, the choroid plexus organoid comprises: (a) an epithelium comprising a tight epithelial barrier; and/or (b) one or more cysts surrounded by an epithelium.

In some embodiments, the stem cells are embryonic stem cells. In some embodiments, the stem cells are induced pluripotent stem cells.

In some embodiments, culturing the population of neuroepithelial cells in the presence of a WNT pathway activator and a BMP signalling pathway activator is started less than 18 days e.g. between about 8-12 days after starting culturing the population of stem cells. In some embodiments, culturing the population of neuroepithelial cells in the presence of a WNT pathway activator and a BMP signalling pathway activator is started between about 9-11 days after starting culturing the population of stem cells. In some embodiments, culturing the population of neuroepithelial cells in the presence of a WNT pathway activator and a BMP signalling pathway activator is started between about 9.5-10.5 days after starting culturing the population of stem cells. In some embodiments, culturing the population of neuroepithelial cells in the presence of a WNT pathway activator and a BMP signalling pathway activator is started about 10 days after starting culturing the population of stem cells.

In another aspect, the invention provides a method for producing a choroid plexus organoid comprising the steps:
(a) producing a population of embryoid bodies by culturing a population of stem cells;
(b) culturing the population of embryoid bodies under conditions suitable for neural induction;
(c) embedding the product of step (b) in a three-dimensional matrix, preferably an extracellular matrix (ECM);
(d) culturing the product of step (c) in the presence of a WNT pathway activator and a bone morphogenetic protein (BMP) signalling pathway activator, preferably wherein step (d) is started between about 8-12 days after the start of step (a).

In some embodiments, the stem cells are embryonic stem cells. In some embodiments, the stem cells are induced pluripotent stem cells.

In some embodiments, the culturing of step (a) is for about 4-6 days, preferably about 4.5-5.5 days, preferably about 5 days.

In preferred embodiments, the culturing of step (b) is carried out until neuroepithelia are present. In some embodiments, the culturing of step (b) is for about 1-3 days, preferably about 1.5-2.5 days, preferably about 2 days.

In some embodiments, the ECM is a polymerised ECM. In some embodiments, the ECM is a polymerised ECM gel. In some embodiments, the ECM is Matrigel.

Thus in some embodiments step (c) is performed using Matrigel, about 5-9 days, more preferably 6-8 days, most preferably 7 days after starting culture.

In some embodiments, step (c) further comprises culturing the embedded embryoid bodies.

In some embodiments, the culturing of step (c) is for about 2-4 days, preferably about 2.5-3.5 days, preferably about 3 days.

In some embodiments, step (d) is started between about 9-11 days, preferably about 9.5-10.5 days, preferably about 10 days after the start of step (a).

In some embodiments, the culturing in the presence of a WNT pathway activator and a BMP signalling pathway activator is for about 6-8 days, preferably about 6.5-7.5 days, preferably about 7 days.

In preferred embodiments, the culturing of step (d) comprises agitation.

In some embodiments, agitation is not applied during contact with the WNT pathway activator and the BMP signalling pathway activator. In some embodiments, the agitation is started at about day 15.

In some embodiments, the method comprises feeding the culture every 3-4 days with culture medium starting at day 15, optionally wherein ECM is added to the culture medium starting at day 30. Preferably, the ECM is soluble ECM—for example dissolved Matrigel.

In preferred embodiments, the method is an in vitro method.

In some embodiments, the WNT pathway activator is selected from the group consisting of CHIR99021, Wnt1, Wnt2, Wnt3, Wnt3a, Wnt8a, Wnt8b, Wnt10a, Wnt10b, BML-284, 6-bromoindirubin-3'-oxime (BIO), WAY-316606, IQ1, QS11, SB-216763, LY2090314, DCA, 2-amino-4-[3,4-(methylenedioxy)benzyl-amino]-6-(3-methoxyphenyl)pyrimidine and lithium.

In preferred embodiments, the WNT pathway activator is CHIR99021.

In some embodiments, the BMP signalling pathway activator is selected from the group consisting of Bmp4, Bmp2, Bmp3, Bmp5, Bmp6, Bmp7, Bmp8a, Bmp8b, Bmp10, Bmp11, Bmp15, isoliquiritigenin, 4'-hydroxychalcone, apigenin, diosmetin, and a ventromorphins (e.g. SJ000291942, SJ000063181 and/or SJ00037178).

In preferred embodiments, the BMP signalling pathway activator is Bmp4.

In preferred embodiments, the WNT pathway activator is CHIR99021 and the BMP signalling pathway activator is Bmp4.

In some embodiments, the method or use does not comprise contacting the cells with a WNT pathway inhibitor.

In some embodiments, the method or use does not comprise exposing the cells to high oxygen partial pressure, for example an oxygen partial pressure greater than that of air (20%). In some embodiments, the method or use comprises culturing only under an oxygen partial pressure of less than or equal to 20%.

As explained above, as part of its selective barrier function, the ChP epithelium is also highly selective to small molecules, including therapeutics. The present invention has particular utility in investigating and screening CNS-active drugs.

New drugs too often progress to clinical trial before failing for lack of efficacy, inability to cross in to the CNS, or limited translatability between animal models (52).

The present ChP organoids have utility in, for example, preclinical testing and modelling in vivo drug permeability into the CNS which may have benefits compared to the current standard in preclinical assays of CNS permeability (e.g. canine MDCK or Caco-2 cells, or artificial membrane assays that are based on phospholipid mixtures which lack transporters and carrier proteins (53)).

In another aspect, the invention provides use of the choroid plexus organoid of the invention for drug discovery screening or assaying drug toxicity. The drug may be a CNS drug e.g. a small molecule drug e.g. for a neurodegenerative disease such as Alzheimer's Disease In some embodiments, the use is for testing the ability of a candidate agent to cross and/or selectively cross the blood-cerebrospinal fluid (CSF) barrier. In another aspect, the invention provides a method for testing the ability of a candidate agent to cross the blood-cerebrospinal fluid (CSF) barrier, comprising contacting the choroid plexus organoid of the invention with the candidate agent and determining if the candidate agent crosses the epithelium.

DETAILED DESCRIPTION OF THE INVENTION

Figure 1:
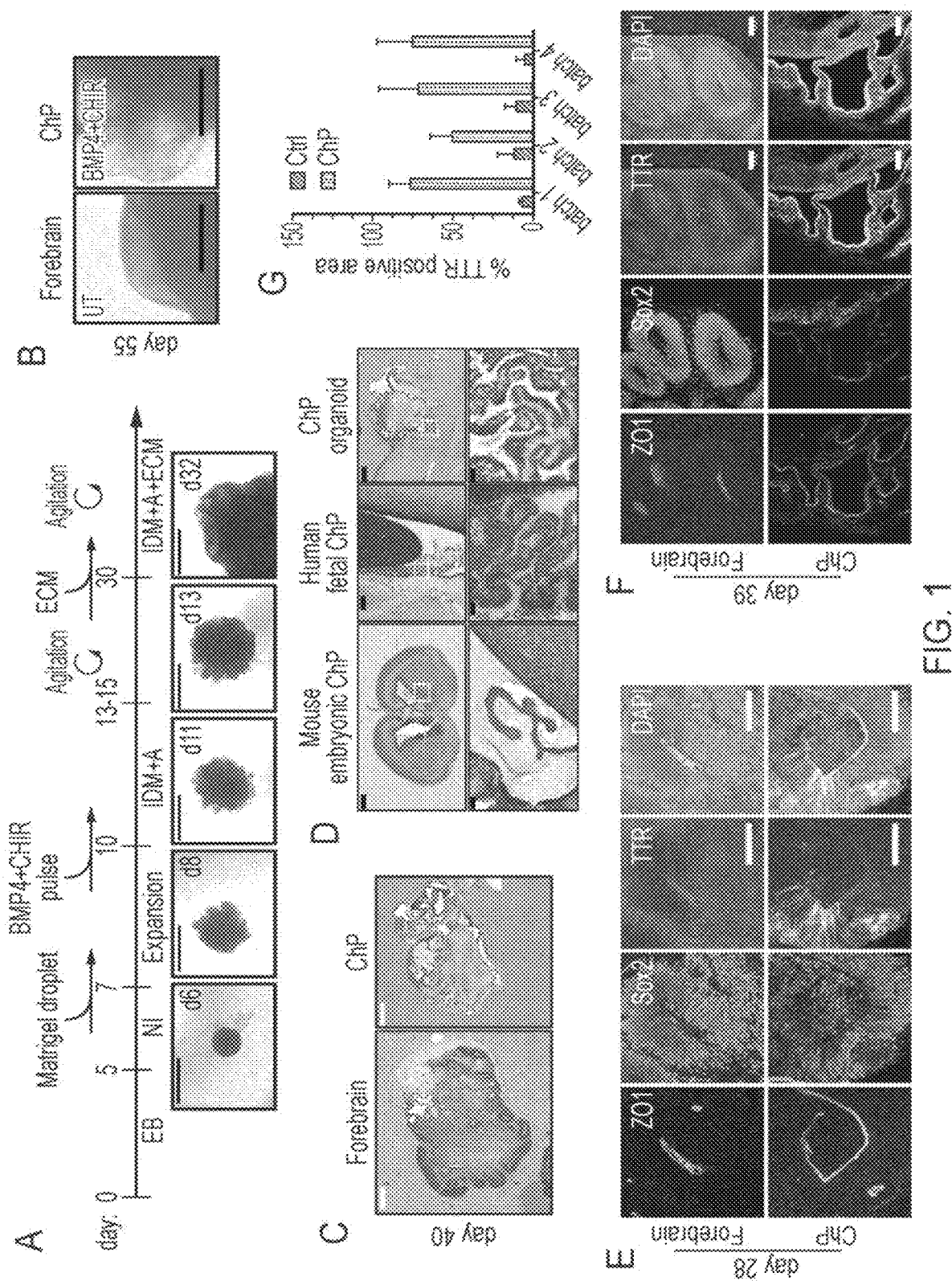
FIG. 1. Generation of choroid plexus organoids from human PSCs. (A) Protocol timeline showing different images from H9 organoid stages of growth. BMP4 and Wnt activator CHIR are added at day 10 of the protocol to promote dorsalisation. Scale bar: 1000 µm. (B) Comparison of H1 treated, choroid plexus (ChP) organoid to untreated (UT), forebrain organoid at day 55. Scale bar: 1 mm. (C) H&E stained sections of H1 forebrain and choroid plexus organoids at day 40. Scale bar: 500 µm. (D) Histological sections of E18.5 mouse embryonic brain (H&E stained), human fetal ChP at 15 post-conception weeks (Nissl stained, taken from Allen Brain Map http://portal.brain-map.org/), H1 human ChP organoid at day 40 (H&E stained). Scale bar: 500 µm, 50 µm for magnification. (E), (F) Representative confocal images of IMR90-4 iPSC derived forebrain and ChP organoids stained for TTR (grey, anti-sheep Alexafluor 647), ZO1 (green, anti-mouse Alexafluor 488) and Sox2 (magenta, anti-rabbit Alexafluor 568) at day 28 (E) and day 39 (F). Nuclei in blue are stained for DAPI. Scale bar: 100 µm. (G) Quantification of percentage of TTR positive area over total organoid area in n=4 independent H9 batches (3-4 organoids per batch collected at d30, d40, d48).

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Organoid

Organoids are three-dimensional (3D) in vitro cell cultures. Organoids may provide a miniaturised and simplified version of an organ, which incorporate some key features of the organ. These in vitro culture systems may contain a self-renewing stem cell population that differentiates into multiple, organ-specific cell types with spatial organisation similar to the organ.

Choroid Plexus

The choroid plexus is a highly conserved secretory tissue in the brain, which displays a number of important functions, such as forming a protective epithelial barrier and secreting the cerebrospinal fluid (CSF).

Anatomically, the choroid plexus is localised in the lateral, third and fourth ventricles emerging in each respective lumen. The mature choroid plexus is composed of a single cuboidal epithelium, surrounding a core of mesenchyme-derived stromal tissue and fenestrated capillaries. The epithelial cells are closely connected with tight junctions and highly polarised with an apical brush border facing the lumen of the ventricle and a basal surface on the stromal side.

There are different mechanisms involved in CSF production. First, the $Na^+$—$K^+$ ATPase pumps, located on the apical side of choroid plexus epithelial cells, and the cytoplasmic carbonic anhydrase generate an osmotic gradient mainly driven by secretion of $Na^+$ into the lumen of the ventricle. This osmotic force drives transcellular water influx through aquaporin channels. Second, ATP-binding cassette (ABC) proteins and solute carrier transporters (SLCs) allow the exchange of amino acids, nucleosides and small peptides with and without the requirement of ATP hydrolysis, respectively. The choroid plexus epithelial cells also express efflux transporters, such as MRP1 and MRP4 (Redzic, Z. (2011) Fluids Barriers CNS 8: 3; Strazielle, N. and Ghersi-Egea, J. F. (2013) Mol. Pharm. 10: 1473-1491). These pumps regulate the clearance of metabolites, and prevent entry of drugs and toxic compounds, thus reducing their availability in the CSF. Third, the highly specialised and expanded secretory system of choroid plexus epithelial cells enables more complex protein and hormone secretion. For example, transthyretin (TTR), a carrier of thyroid hormones and retinol, is the most abundant protein synthesised and secreted by the choroid plexus (Li, X. and Buxbaum, J. N. (2011) Mol. Neurodegener. 6: 1-17; Richardson, S. J. et al. (2015) Front. Neurosci. 9: 1-8; Johnson, B. A. et al. (2018) Fluids Barriers CNS 15: 22). TTR-mediated delivery of thyroid hormones to the CSF appears to have an important role in regulation of brain development.

Choroid plexus tissue may be identified by the expression of choroid plexus markers and/or by the structural features of the tissue.

The choroid plexus may be characterised by the expression of one or more markers selected from the group consisting of transthyretin (TTR), MRP1, MRP4, aquaporin 1 (Aqp1) and zonula occludens (ZO1).

The choroid plexus may be characterised by the expression of markers localised or enriched in certain types of cells. For example, the choroid plexus may be characterised by the expression of one or more markers selected from the group consisting of TTR, MRP1, MRP4, Aqp1 and ZO1 in epithelial cells.

In addition, the markers may be localised or enriched in certain areas of certain cells. For example, TTR, Aqp1 and/or ZO1 may be enriched on the apical side of the epithelium. MRP1 and/or MRP4 may be enriched on the apical and basal sides of the epithelium.

The choroid plexus may be characterised by the absence or low expression of FOXG1.

The choroid plexus may be characterised by the presence of apical microvilli in the epithelium. The choroid plexus epithelium may comprise centro-basally located nuclei.

The choroid plexus epithelium may be apico-basal polarised. For example, the epithelium may be polarised, with Aqp1 and ZO1 expressed on the luminal side of the epithelium.

The presence, absence and localisation of such markers can be readily determined by the skilled person. For example, markers may be identified by immunostaining using antibodies specific to the markers, for example in association with visualisation techniques such as confocal microscopy. In addition, or in the alternative, specific oligonucleotide probes, which preferably bind to a marker nucleic acid may be employed.

Tight Epithelial Barrier

A tight epithelial barrier may be formed by tight junctions between epithelial cells.

Tight junctions (also referred to as occluding junctions or zonulae occludentes) may be formed by multiprotein complexes, and may seal the paracellular pathway and prevent leakage of transported solutes and water.

The choroid plexus tightly sealed epithelium is also known as the blood-CSF barrier (B-CSF-B). The B-CSF-B, similar to the blood-brain barrier (BBB), prevents toxic substances or signals in the circulation from reaching the brain. However, in contrast to the BBB, the B-CSF-B is formed by a single cell type, the choroid plexus epithelial cells, and it faces the CSF rather than the brain parenchyma directly. However, because the CSF has free access to the brain, transport of molecules across the B-CSF-B is an alternative route into the brain.

Tight junctions, such as comprised in a tight epithelial barrier, may be characterised by the expression of zonula occludens (ZO1).

Cerebrospinal Fluid (CSF)

Cerebrospinal fluid (CSF) is a clear, colourless fluid that circulates through the ventricles of the brain and the subarachnoid spaces, and is then partly reabsorbed into the blood circulation through arachnoid granulations.

CSF is important for the maintenance of physiological levels of nutrients in the brain, for the transport of signalling molecules and growth factors, and for its protective role in the regulation of intracranial pressure.

CSF is produced by active secretion from the choroid plexus epithelial cells, which maximise the number of transporters and pumps in their apical brush border, and from filtration of blood granted by the presence of tight junctions within the choroid plexus epithelial cells. The choroid plexus has a key role in maintaining the rates of production and reabsorption of CSF. Disturbances of this equilibrium lead to pathologies such as hydrocephalus.

CSF may be characterised by the presence of one or more markers selected from the group consisting of TTR, clusterin (CLU), apolipoprotein E (APOE), apolipoprotein A4 (APOA4) and lumican (LUM).

CSF may be characterised by the presence alphafetoprotein (AFP).

WNT Pathway Activator

The WNT pathway activator that may be used to produce the choroid plexus organoids of the invention is not particularly limited, provided that it is capable of activating the WNT signalling pathway.

WNT pathway activators include, but are not limited to agents such as CHIR99021, Wnt1, Wnt2, Wnt3, Wnt3a, Wnt8a, Wnt8b, Wnt10a, Wnt10b, BML-284, 6-bromoindirubin-3'-oxime (BIO), WAY-316606, IQ1, QS11, SB-216763, LY2090314, DCA, 2-amino-4-[3,4-(methylenedioxy)benzyl-amino]-6-(3-methoxyphenyl)pyrimidine and lithium In preferred embodiments, the WNT pathway activator is CHIR99021 (also referred to herein as "CHIR").

CHIR99021 is an aminopyrimidine derivative that is an extremely potent inhibitor of GSK3, inhibiting GSK3β ($IC_{50}$=6.7 nM) and GSK3α ($IC_{50}$=10 nM) and functions as a WNT activator. CHIR99021 has the structure:

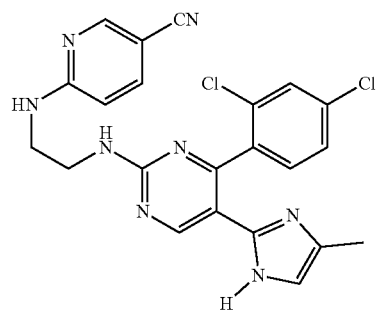 [SMILES: Cc1c[nH]c(-c2cnc(NCCNc3ccc(C#N)cn3)nc2-c2ccc(Cl)cc2Cl)n1]

In some embodiments, the CHIR99021 is used at a concentration of about 1-25, 1-20, 1-15, 1-10, 1-9, 1-8, 1-7, 1-6, 1-5, 1-4 or 1-3 µM. In some embodiments, the CHIR99021 is used at a concentration of about 1-5 µM.

In some embodiments, the CHIR99021 is used at a concentration of about 2-25, 2-20, 2-15, 2-10, 2-9, 2-8, 2-7, 2-6, 2-5 or 2-4 µM. In preferred embodiments, the CHIR99021 is used at a concentration of about 2-4 µM.

In some embodiments, the CHIR99021 is used at a concentration of about 1, 2, 3, 4, 5, 6, 7, 8, 9, 10, 11, 12, 13, 14, 15, 16, 17, 18, 19, 20, 21, 22, 23, 24 or 25 µM. In preferred embodiments, the CHIR99021 is used at a concentration of about 3 µM.

Bone Morphogenetic Protein (BMP) Signalling Pathway Activator

The bone morphogenetic protein (BMP) signalling pathway activator that may be used to produce the choroid plexus organoids of the invention is not particularly limited, provided that it is capable of activating the BMP signalling pathway.

BMP signalling pathway activators include, but are not limited to agents such as Bmp4, Bmp2, Bmp3, Bmp5, Bmp6, Bmp7, Bmp8a, Bmp8b, Bmp10, Bmp11, Bmp15, isoliquiritigenin, 4'-hydroxychalcone, apigenin, diosmetin, and a ventromorphins (e.g. SJ000291942, SJ000063181 and/or SJ00037178).

In preferred embodiments, the BMP signalling pathway activator is Bmp4.

Bone morphogenetic protein 4 (Bmp4) is a member of the TGF-β superfamily of proteins. It is involved in bone and cartilage development, for example tooth and limb development and fracture repair.

In human embryonic development, Bmp4 is an important signalling molecule involved in the early differentiation of the embryo and establishing of a dorsal-ventral axis.

An example amino acid sequence of human Bmp4 is the sequence deposited under NCBI Accession No. NP_001193.2.

An example amino acid sequence of human Bmp4 is:

(SEQ ID NO: 1)
MIPGNRMLMVVLLCQVLLGGASHASLIPETGKKKVA

EIQGHAGGRRSGQSHELLRDFEATLLQMFGLRRRPQ

PSKSAVIPDYMRDLYRLQSGEEEEQIHSTGLEYPE

RPASRANTVRSFHHEEHLENIPGTSENSAFRFLFNL

SSIPENEVISSAELRLFREQVDQGPDWERGEHRINI

YEVMKPPAEVVPGHLITRLLDTRLVHHNVTRWETFD

VSPAVLRWTREKQPNYGLAIEVTHLHQTRTHQGQHV

RISRSLPQGSGNWAQLRPLLVTFGHDGRGHALTRRR

RAKRSPKHHSQRARKKNKNCRRHSLYVDFSDVGWND

WIVAPPGYQAFYCHGDCPFPLADHLNSTNHAIVQTL

VNSVNSSIPKACCVPTELSAISMLYLDEYDKVVLKN

YQEMVVEGCGCR

In some embodiments, the Bmp4 is used at a concentration of about 1-40, 5-35, 10-30, 15-25, 16-24, 17-23, 18-22 or 19-21 ng/ml. In some embodiments, the Bmp4 is used at a concentration of about 19-21 ng/ml.

In some embodiments, the Bmp4 is used at a concentration of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 ng/ml. In preferred embodiments, the Bmp4 is used at a concentration of about 20 ng/ml.

Salts

The agents of the invention (e.g. the WNT pathway activator and/or the BMP signalling pathway activator) can be present as salts, in particular pharmaceutically-acceptable salts or esters.

Pharmaceutically-acceptable salts of the agents of the invention include suitable acid addition or base salts thereof. A review of suitable pharmaceutical salts may be found in Berge. et al. (1977) J. Pharm. Sci. 66: 1-19. Salts are formed, for example, with strong inorganic acids such as mineral acids, e.g. sulphuric acid, phosphoric acid or hydrohalic acids; with strong organic carboxylic acids, e.g. alkanecarboxylic acids of 1 to 4 carbon atoms which are unsubstituted or substituted (e.g. by halogen), such as acetic acid; with saturated or unsaturated dicarboxylic acids, e.g. oxalic, malonic, succinic, maleic, fumaric, phthalic or tetraphthalic acid; with hydroxycarboxylic acids, e.g. ascorbic, glycolic, lactic, malic, tartaric or citric acid; with amino acids, e.g. aspartic or glutamic acid; with benzoic acid; or with organic sulfonic acids, such as ($C_1$-$C_4$)-alkyl- or aryl-sulfonic acids, which are unsubstituted or substituted (e.g. by a halogen), such as methane- or p-toluene sulfonic acid.

Enantiomers/Tautomers

The invention also includes where appropriate all enantiomers and tautomers of the agent. The corresponding enantiomers and/or tautomers may be isolated/prepared by methods known in the art.

Stereo and Geometric Isomers

Some of the agents of the invention may exist as stereoisomers and/or geometric isomers. For example, they may possess one or more asymmetric and/or geometric centres and so may exist in two or more stereoisomeric and/or geometric forms. The invention contemplates the use of all the individual stereoisomers and geometric isomers of those agents, and mixtures thereof. The terms used in the claims encompass these forms, provided said forms retain the appropriate functional activity (though not necessarily to the same degree).

The invention also includes all suitable isotopic variations of the agent or pharmaceutically-acceptable salts thereof. An isotopic variation of an agent of the invention or a pharmaceutically-acceptable salt thereof is defined as one in which at least one atom is replaced by an atom having the same atomic number, but an atomic mass different from the atomic mass usually found in nature. Examples of isotopes that can be incorporated into the agent and pharmaceutically-acceptable salts thereof include isotopes of hydrogen, carbon, nitrogen, oxygen, phosphorus, sulphur, fluorine and chlorine, such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically-acceptable salts thereof, for example, those in which a radioactive isotope such as $^3$H or $^{14}$C is incorporated, are useful in drug and/or substrate tissue distribution studies. Tritiated, i.e. $^3$H, and carbon-14, i.e. $^{14}$C, isotopes are particularly preferred for their ease of preparation and detectability. Further, substitution with isotopes such as deuterium, i.e. $^2$H, may afford certain therapeutic advantages resulting from greater metabolic stability, for example, increased in vivo half-life or reduced dosage requirements and hence may be preferred in some circumstances. Isotopic variations of the agent of the invention and pharmaceutically-acceptable salts thereof of this invention can generally be prepared by conventional procedures using appropriate isotopic variations of suitable reagents.

Solvates

The invention also includes solvate forms of the agents of the invention. The terms used in the claims encompass these forms.

Polymorphs

The invention also relates to the agents of the invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Stem Cells

The choroid plexus organoids of the invention may be produced (e.g. in vitro) from stem cells. The choroid plexus organoids are not isolated from the brain of an animal, which facilitates the production of tissue without the need to obtain tissue samples from an animal.

Stem cells are cells that have the capacity to differentiate into more specialised cells and can also divide to produce more stem cells.

With decreasing differentiation capabilities, stem cells differentiate in the following order: pluripotent, multipotent, unipotent. During development of the organoid of the disclosure, stem cells may differentiate, for example, from pluripotent into multipotent neural stem cells, further into unipotent stem cells and subsequently into non-stem tissue cells. The tissue cells may be, for example, neuroepithelial cells.

The methods of the invention may comprise contacting a population of precursor cells (e.g. a population of neuroepithelial cells) with a WNT pathway activator and a bone morphogenetic protein (BMP) signalling pathway activator, wherein the population of precursor cells has itself been produced (e.g. in vitro) by the differentiation of a population of stem cells.

Thus, the methods of the invention may comprise the step of producing a population of cells (e.g. in vitro) from a population of stem cells.

Preferably, the stem cells of the invention are pluripotent stem cells.

Pluripotent stem cells are stem cells that may propagate indefinitely. Pluripotent stem cells are not capable of growing into an entire organism, but are capable of giving rise to cell types originating from all three germ layers, i.e. mesoderm, endoderm and ectoderm, and may be capable of differentiating into all cell types of the human body. These stem cells hold promise in providing a single source of cells that may replace cells affected by damage or disease.

Pluripotent stem cells may be created through a number of techniques, such as the generation of induced pluripotent stem cells or embryonic stem cells.

In some embodiments, the stem cells of the invention are induced pluripotent stem cells (iPSCs).

iPSCs are a type of pluripotent stem cell that may be created directly from adult cells. The skilled person is readily able to prepare iPSCs, for example by introducing specific transcription factors into adult cells or contacting adult cells with specific protein combinations.

iPSCs are advantageous over embryonic stem cells in that they overcome the need for using embryonic material and can be prepared from a subject to which they (or cells produced from them) are later re-introduced. Such autologous cell transplantation may overcome the risk of immune rejection of transplanted material.

The stem cells of the invention may be embryonic stem cells, in particular those produced without destruction of an embryo.

Methods are known in the art for producing pluripotent stem cells, such as mammalian embryonic stem cells, without the destruction of an embryo. In particular, it has been shown that mouse and human embryonic stem cells may be produced from single blastomeres while leaving the embryo intact. For example Chung, Y. et al. (2006) Nature 439: 216-219 describes methods for making mouse embryonic stem cells from a single blastomere. Later advances on this procedure provided methods where co-culturing the blastomere cell lines with other ESCs is not required (Chung, Y. et al. (2008) Cell Stem Cell 2: 113-117).

In some embodiments, the stem cells of the invention are mammalian stem cells, preferably human stem cells.

Method for Producing Choroid Plexus Organoids

The choroid plexus organoid of the invention may be produced using a WNT pathway activator and a bone morphogenetic protein (BMP) signalling pathway activator.

In one aspect, the invention provides use of a WNT pathway activator and a bone morphogenetic protein (BMP) signalling pathway activator for producing a choroid plexus organoid, wherein the choroid plexus organoid comprises (a) an epithelium comprising a tight epithelial barrier; and/or (b) one or more cysts surrounded by an epithelium.

In another aspect, the invention provides a method for producing a choroid plexus organoid comprising contacting a population of neuroepithelial cells with a WNT pathway activator and a bone morphogenetic protein (BMP) signalling pathway activator, wherein the choroid plexus organoid comprises: (a) an epithelium comprising a tight epithelial barrier; and/or (b) one or more cysts surrounded by an epithelium.

In another aspect, the invention provides a method for producing a choroid plexus organoid comprising producing a population of neuroepithelial cells from a population of stem cells, and culturing the population of neuroepithelial cells in the presence of a WNT pathway activator and a bone morphogenetic protein (BMP) signalling pathway activator. In preferred embodiments, the choroid plexus organoid comprises: (a) an epithelium comprising a tight epithelial barrier; and/or (b) one or more cysts surrounded by an epithelium.

In some embodiments, the stem cells are embryonic stem cells. In some embodiments, the stem cells are induced pluripotent stem cells.

In preferred embodiments, the population of neuroepithelial cells is an aggregate of neuroepithelial cells.

In preferred embodiments, the population of neuroepithelial cells is embedded in a three-dimensional matrix, preferably an extracellular matrix (ECM), before contacting with a WNT pathway activator and a bone morphogenetic protein (BMP) signalling pathway activator.

In some embodiments, culturing the population of neuroepithelial cells in the presence of a WNT pathway activator and a BMP signalling pathway activator is started between about 8-12 days after starting culturing the population of stem cells. In some embodiments, culturing the population of neuroepithelial cells in the presence of a WNT pathway activator and a BMP signalling pathway activator is started between about 9-11 days after starting culturing the population of stem cells. In some embodiments, culturing the population of neuroepithelial cells in the presence of a WNT pathway activator and a BMP signalling pathway activator is started between about 9.5-10.5 days after starting culturing the population of stem cells. In some embodiments, culturing the population of neuroepithelial cells in the presence of a WNT pathway activator and a BMP signalling pathway activator is started about 10 days after starting culturing the population of stem cells.

In some embodiments, the method or use comprises agitation, preferably after contact with the WNT pathway activator and the BMP signalling pathway activator. Agitation may be achieved using, for example, a shaker, such as an orbital shaker.

In another aspect, the invention provides a method for producing a choroid plexus organoid comprising the steps:
(a) producing a population of embryoid bodies by culturing a population of stem cells;
(b) culturing the population of embryoid bodies under conditions suitable for neural induction;
(c) embedding the product of step (b) in a three-dimensional matrix, preferably an extracellular matrix (ECM);
(d) culturing the product of step (c) in the presence of a WNT pathway activator and a bone morphogenetic protein (BMP) signalling pathway activator, preferably wherein step (d) is started between about 8-12 days after the start of step (a).

Embryoid bodies (EBs) are three-dimensional aggregates of pluripotent stem cells that undergo spontaneous or directed differentiation.

The method and use of the invention may comprise embedding cells or aggregates of cells in a three-dimensional matrix, preferably an extracellular matrix (ECM).

In some embodiments, the ECM is a polymerised ECM. In some embodiments, the ECM is a polymerised ECM gel. A suitable three-dimensional matrix may comprise collagen. Preferably, the three dimensional matrix comprises ECM secreted by Engelbreth-Holm-Swarm (EHS) mouse sarcoma cells or any component thereof such as laminin, collagen, type 4 collagen, entactin, and optionally further heparan-sulfated proteoglycan or any combination thereof. In some embodiments, the ECM is Matrigel. Matrigel is described in, for example, U.S. Pat. No. 4,829,000.

Typically, the three-dimensional matrix is a three-dimensional structure of a biocompatible matrix. It preferably comprises collagen, gelatin, chitosan, hyaluronan, methylcellulose, laminin and/or alginate. The matrix may be a gel, in particular a hydrogel. Organo-chemical hydrogels may comprise polyvinyl alcohol, sodium polyacrylate, acrylate polymers and copolymers with an abundance of hydrophilic groups. Hydrogels comprise a network of polymer chains that are hydrophilic, sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content.

Production of a population of embryoid bodies may be carried out by culturing a population of stem cells in suitable media (referred to herein as embryoid body (EB) media).

An example EB media comprises serum replacement formulation, foetal bovine serum, glutamine, non-essential amino acids, 2-mercaptoethanol and FGF (e.g. basic FGF) (preferably about 4 ng/ml bFGF). Preferably, EB media comprises ROCK inhibitor. Preferably, EB media comprises ROCK inhibitor only for the first 3 days of culturing the stem cells.

A particularly suitable medium is the EB media used in the examples or the EB media disclosed below.

Neural induction may be carried out by culturing in a suitable media (referred to herein as neural induction media). Neural induction media may be a depleted media, for example lacking serum or serum substitutes. The absence of such nutrients, which are required by non-neural tissue may result in a loss of other non-neural identities and purification toward neural identity.

An example neural induction media comprises N2 supplement (Price and Brewer (2001) Protocols for Neural Cell Culture 255-264; e.g. Invitrogen, Catalogue No. 17502048), glutamine, non-essential amino acids and heparin.

A particularly suitable medium is the neural induction media used in the examples or the neural induction media disclosed below.

In preferred embodiments, individual embryoid bodies are embedded in separate three-dimensional matrix droplets.

Embedding in a three-dimensional matrix may be achieved by adding embryoid bodies to soluble matrix in a suitable container and subsequently incubating under conditions suitable for polymerisation of the matrix. For example, embryoid bodies may be transferred one by one to dimpled Parafilm; after removal of excess media and droplets of matrix (e.g. Matrigel) may be added to each embryoid body; and the mixtures may then be incubated under conditions suitable for polymerisation of the matrix (e.g. at 37° C. for about 20 min).

In preferred embodiments, the embryoid bodies embedded in three-dimensional matrix are cultured under conditions suitable for expansion. Expansion may be carried out by culturing in a suitable media (referred to herein as expansion media).

An example expansion media comprises N2 supplement (Price and Brewer (2001) Protocols for Neural Cell Culture 255-264; e.g. Invitrogen, Catalogue No. 17502048), B27 supplement lacking vitamin A (Price and Brewer (2001) Protocols for Neural Cell Culture 255-264; e.g. Invitrogen, Catalogue No. 12587010), insulin, 2-mercaptoethanol, glutamine and non-essential amino acids.

A particularly suitable medium is the expansion media used in the examples or the expansion media disclosed below.

Culturing in the presence of a WNT pathway activator and a bone morphogenetic protein (BMP) signalling pathway activator, and subsequent culturing in the absence of WNT pathway activator and a bone morphogenetic protein (BMP) signalling pathway activator may be carried out in a suitable media, which may be referred to herein as maturation media.

An example maturation media comprises N2 supplement (Price and Brewer (2001) Protocols for Neural Cell Culture 255-264; e.g. Invitrogen, Catalogue No. 17502048), B27 supplement comprising vitamin A (Price and Brewer (2001) Protocols for Neural Cell Culture 255-264; e.g. Invitrogen, Catalogue No. 17504044), insulin, 2-mercaptoethanol, glutamine and non-essential amino acids.

A particularly suitable medium is the maturation media used in the examples or the maturation media disclosed below.

Any medium may further comprise nutrients and/or buffers. Preferred nutrients include a carbohydrate, especially a mono-hexose or mono-pentose, such as glucose or fructose.

Suitable culture conditions for use in the methods of the invention include, for example:
(a) culturing at about 36-39° C. or 36.5-37.5° C., preferably about 37° C.;
(b) culturing at about 4-6% or 4.5-5.5% $CO_2$, preferably about 5% $CO_2$; and/or
(c) culturing at least about 95%, 96%, 97%, 98% or 99% humidity, preferably about 100% humidity.

A further example EB media is (per 50 mL): 40 ml DMEM/F12 (Invitrogen Catalogue No. 11330-032); 10 ml Knock-out serum replacement (KOSR; Invitrogen Catalogue No. 10828-028); 1.5 ml embryonic stem cell-quality FBS; 0.5 ml GlutaMAX (Invitrogen Catalogue No. 35050-038); 0.5 ml MEM-non-essential amino acids (MEM-NEAA; Sigma Catalogue No. M7145); 100 µl of 50 mM 2-ME (e.g. Life Technologies Catalogue No. 31350-010); 4 ng/ml bFGF (e.g. Peprotech Catalogue No. 100-18B) (added immediately before use; 1:2500); and 1:100 Rock inhibitor (Y27632; VWR Catalogue No. 688000-5) (added immediately before use).

A further example neural induction media is (per 100 mL): 100 ml DMEM/F12 (Invitrogen Catalogue No. 11330-032); 1 ml N2 supplement (Invitrogen Catalogue No. 17502048); 1 ml Glutamax supplement (Invitrogen Catalogue No. 35050-038); 1 ml MEM-NEAA (Sigma Catalogue No. M7145); and 100 ul Heparin solution (Sigma Catalogue No. H3149).

A further example expansion media is (per 250 mL): 125 ml DMEM/F12 (Invitrogen Catalogue No. 11330-032); 125 ml Neurobasal medium (Invitrogen Catalogue No. 21103049); 1.25 ml N2 supplement (Invitrogen Catalogue No. 17502048); 5 ml B27 supplement (Invitrogen Catalogue No. 12587010 or 17504044); 62.5 ul insulin (Sigma Catalogue No. 19278); 250 ul of 50 mM 2-ME solution (e.g. Life Technologies Catalogue No. 31350-010); 2.5 ml Glutamax supplement (Invitrogen Catalogue No. 35050-038); 1.25 ml MEM-NEAA (Sigma Catalogue No. M7145); and 2.5 ml Penicillin/Streptomycin (Sigma Catalogue No. P0781).

A further example maturation media is (per 250 mL): 125 ml DMEM/F12 (Invitrogen Catalogue No. 11330-032); 125 ml Neurobasal medium (Invitrogen Catalogue No. 21103049); 1.25 ml N2 supplement (Invitrogen Catalogue No. 17502048); 5 ml B27 supplement (Invitrogen Catalogue No. 12587010 or 17504044); 62.5 ul insulin (Sigma Catalogue No. 19278); 250 ul of 50 mM 2-ME solution (e.g. Life Technologies Catalogue No. 31350-010); 2.5 ml Glutamax supplement (Invitrogen Catalogue No. 35050-038); 1.25 ml MEM-NEAA (Sigma Catalogue No. M7145); and 2.5 ml Penicillin/Streptomycin (Sigma Catalogue No. P0781).

Methods for Screening and Assaying

In one aspect, the invention provides use of the choroid plexus organoid of the invention for drug discovery screening or assaying drug toxicity.

In some embodiments, the use is for testing the ability of a candidate agent to cross the blood-cerebrospinal fluid (CSF) barrier.

In another aspect, the invention provides a method for testing the ability of a candidate agent to cross the blood-cerebrospinal fluid (CSF) barrier, comprising contacting the choroid plexus organoid of the invention with the candidate agent and determining if the candidate agent crosses the epithelium.

For example, the candidate agent may be added to the culture medium of a culture comprising the choroid plexus organoid and incubated. Subsequently, for example after a suitable period of time, the liquid in the one or more cysts of the choroid plexus organoid may be extracted and analysed for the presence of the candidate agent. Any suitable technique known to the skilled person may be used to assay for the presence of the candidate agent. For example, agents may be identified using mass spectrometric methods.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Materials and Methods

Stem Cell Culture

Human H9 and H1 ES cells were obtained from WiCell and have been approved for these studies by the UKSCB Steering Committee, iPS cells (IMR90-4) were obtained from WiCell and all cell lines were verified pluripotent and mycoplasma free. Cells were maintained in culture and fed with StemFlex culture media (Gibco A3349401).

Cerebral and Choroid Plexus Organoid Culture Conditions

Embryoid bodies (EBs) were prepared from single cell suspension from hES and iPSCs as previously described (1). Stem Cell Technologies Cerebral Organoid kit (catalogue n. 08570, 08571) reagents were used for the generation of cerebral and ChP organoids. EBs were generated using either fibrous microscaffolds and 18,000 hES or iPS cells, or fewer cells (2000-4000) in the absence of microscaffolds to generate smaller EBs, in both cases to increase surface area and improve neural induction efficiency as previously reported (2). These were plated in 96well U-bottom low attachment plates with EB media and 50 µM Y-27632 ROCK inhibitor for 3 days, followed by 2 days in EB media alone. On day 5 media was replaced with NI media in the same 96-well. After two days EBs were embedded in 20 µl matrigel using sheets of dimpled parafilm and incubated for 20 min at 37° C. as previously described (2). EBs were then transferred to a 6-well plate with 3 ml of Expansion media per well. For ChP patterning, on day 10 treatment with 3 µM CHIR and 20 ng/ml BMP4 in Maturation media was used keeping a maximum number of 6 EBs in each 5 cm dish. The treatment was kept for 7 days in maturation media. On day 15 organoids were moved to an incubator with a shaker and were fed every 3-4 days with maturation media. From day 30 dissolved matrigel (1:50) was added to the maturation media.

Immunostaining and Immunoblotting

Organoids were fixed in 4% PFA overnight at 4° C. then washed in PBS three times, 10 min each and then moved to 30% sucrose buffer at 4° C. for at least 24h. Organoids were then embedded in gelatin and sectioned as previously described (1). After blocking and permeabilisation with 0.25% Triton and 1% donkey serum buffer, sections were incubated overnight with the following primary antibodies: sheep anti-TTR (1:500, Abcam, ab9015), mouse anti-ZO1 (1:300, BD Transduction, 610966), rabbit anti-Aqp1 (1:200, Abcam ab15080), mouse anti-MRP1 (1:200, Abcam ab24102), rabbit anti-MRP4 (1:200, Cell Signaling Technology, 12705), rabbit anti-Sox2 (1:300, Abcam, ab97959), rabbit anti-CLIC6 (1:500 for immunostaining, 1:1000 for immunoblot, Abcam, ab204567), rabbit anti-Foxg1 (1:200 for immunostaining, 1:1000 for immunoblot, Abcam, ab18259), mouse anti-GAPDH (1:1000, Abcam, ab8245), rabbit anti-IGF2 (1:200 for immunostaining, 1:1000 for immunoblot, Abcam, ab9574), rat anti-histone H3 phosphorylated (PH3, 1:300, Abcam ab10543), mouse anti-keratin 18 (Krt18, 1:200, Novus biologicals NBP2-47985), rabbit anti-serotonin (5HT2C, 1:200, Sigma S5545); rabbit anti-CCDC67 (1:200, Abcam ab102688), mouse anti-Foxj1 (1:100, Thermo Fisher 14-9965-82); rabbit anti-Arl13b (1:200, Proteintech 17711-1-AP), rabbit anti-DLK1 (1:200, Abcam, ab21682), sheep anti-Tbr2 (1:200, R&D Systems, AF6166), mouse anti-HuC/D (1:500, LifeTech, A21271), mouse anti-LAT1 (1:50, Santa Cruz, sc-374232), rabbit anti-Pgp/MDR1 (1:200, Cell Signaling Technology, 12683). Secondary antibodies labelled with Alexafluor 488, 568, 647 were applied for 1 h at room temperature after three 10 min PBS washes. To mark the nuclei, DAPI was added to the secondary antibody incubation. Slides were then washed three times in PBS and then mounted with Prolong Diamond mounting media. For histological analysis, sections were subsequently immersed in hematoxylin and then eosin, dehydrated with ethanol and xylene and finally mounted using xylene based mountant media. Images were acquired using a Zeiss LSM 780 confocal microscope (Carl Zeiss) and prepared using Fiji (NIH).

For immunoblotting, organoids were snap-frozen in liquid nitrogen and subsequently homogenised in RIPA buffer with 1:100 Halt protease inhibitors (Thermo Fisher) to produce a tissue extract. To collect iCSF, organoids were washed in fresh media twice and fluid was collected via mouth pipetting using a glass capillary. Protein concentration was measured using Bradford assay. Samples containing approximately 10 μg of protein were then prepared with NuPAGE LDS Sample Buffer 4× and DTT 1M and then heated for 15 min at 95° C. Protein samples and ladder were loaded into a polyacrylamide gel and run at 90 mV for 2h. Samples were transferred to a PVDF membrane (Immobilon) for 3 h at 4° C. Membranes were blocked in 5% milk in PBS-T and incubated with primary antibodies overnight at 4° C. After 3 washes in PBS, secondary antibodies Alexafluor conjugated were added for 1 h at room temperature. Membranes were imaged using a Li-COR Odyssey CLx Infrared Imaging System.

Single Cell RNA Sequencing and Analysis

Single cell dissociation was performed by first pooling two organoids for each condition: 55-day telencephalic organoids (sample 1), 53-day choroid plexus (sample 2), 27-day choroid plexus (sample 3), and 46-day choroid plexus (sample 4), into a 15-ml conical tube. Samples were incubated in 1 ml of Accumax (Sigma, A7089) with 400 μg DNase I and 15 μM actinomycin D at 37 C for 20 min with gentle agitation. At 5 min intervals, the sample tubes were flicked and at the end pipetted up and down 10 times with a P1000 tip. Large clumps were allowed to settle and supernatant collected, to which 100 μl FBS was added before filtration on a 35 μm filter tube (Corning, 352235). Samples were then spun at 300×g for 5 min. Cell pellet was then cleaned of dead cells using the Dead Cell Removal kit and MACS column (Miltenyi, 130-090-101) before another spin at 300×g for 5 min. Cells were resuspended in an appropriate volume of 0.04% BSA in PBS to load 16,000 cells were well on the 10× Chromium system (10× Genomics).

Single cell RNA-seq libraries were prepared according to manufacturer's instructions using the 10× Genomics Chromium Single Cell 3' Library & Gel Bead Kit v3 (10× Genomics) workflow. The Chromium Controller was run according to the protocol producing the single cell gel beads in emulsion mixture. Reverse transcriptase reaction and subsequent amplification was carried out on a C1000 Touch Thermal Cycler (Biorad) and libraries were quality tested using a 2100 Bioanalyzer Instrument (Agilent). Samples were pooled together and sequenced on two lanes of S1 flowcell of the Novaseq sequencer (Illumina).

Raw sequencing output was converted to the standard fastq format by bcl2fastq, before running through CellRanger Count (version 3.1.0, 10× Genomics) which also performed read alignment using STAR with GRCh38 human reference genome. QC output revealed 10,327 cells, with mean reads per cell of 39,973 and median UMI counts per cell of 4,660 for sample 1; 8,573 cells, with mean reads per cell of 41,815 and median UMI counts per cell of 11,899 for sample 2; 5,347 cells, with mean reads per cell of 67,938 and median UMI counts per cell of 16,252 for sample 3; 8,603 cells, with mean reads per cell of 45,030 and median UMI counts per cell of 9,927 for sample 4. The filtered feature barcode matrix for each sample was then analysed further with the Seurat v3 R package by first merging the matrices then normalizing for read depth across cells, scaling the data, and variable feature finding using SCTransform. Both mitochondrial mapping percentage and cell cycle were regressed out during normalization to remove these confounding sources of variation. Unbiased clustering was performed by principle component analysis (PCA) using ElbowPlot to guide selection of the number of dimensions (4), followed by FindNeighbors, FindClusters, and UMAP dimensionality reduction visualization. Clusters were identified based on the top 10 differentially expressed genes in each cluster, as well as analysis of known marker genes.

For comparison with in vivo data, subsets for each individual cluster were first generated. For comparison with human developing brain scRNA-seq, expression matrix and metadata from Nowakowski et al. (3) were downloaded from the UCSC Cell Browser and processed through Seurat v3 with cell cycle state regression and PCA cluster analysis with UMAP visualization, similar to above, to yield 12 clusters identified based on top differentially expressed genes and known marker genes. Subsets were then generated for each of these clusters. Normalized feature count data for each of the cluster subsets from organoids and human in vivo were averaged across single cells within each cluster followed by calculation of Pearson's correlation coefficient across the matrix and unbiased hierarchical cluster analysis using the heatmap.2 function with manhattan method and ward.D2 clustering.

For comparison with mouse embryonic bulk RNA-seq data, raw feature counts were downloaded from NCBI GEO (GSE66312) (4) and TPM calculated followed by conversion to human gene names and removal of duplicates and genes absent in human. A cutoff TPM of 1 in at least one of the samples was set, followed by calculation of mean across 1) the whole choroid plexus samples and 2) the sorted epithelial cell samples. Data was then log transformed and merged with organoid subset clusters (averaged as above). Genes not represented in all compared groups were removed followed by scaling and principle component analysis.

Electron Microscopy

Organoids were fixed in glass vials with 2.5% glutaraldehyde and 2% paraformaldehyde (EM grade, Agar Scientific) in 0.1M cacodylate buffer, pH7.4 (CB) overnight at 4° C. The following day, they were rinsed 6 times over the course of the day with CB and stored overnight at 4° C. Samples were then rinsed once more and postfixed with 1% osmium textroxide in CB on ice and in the dark for 1 hour, washed five times over one hour with distilled water, and dehydrated in an ascending ethanol series (30%, 50%, 70%, 90%, 100%) then propylene oxide for 10 min at each step. The dehydrated samples were infiltrated and embedded in CY212 Araldite epoxy resin. Pale gold 70 nm sections were cut from the embedded samples and contrasted with saturated aqueous uranyl acetate. Electron micrographs were recorded at 80 kV on a FEI Tecnai Spirit TEM.

Mass Spec Data Analysis

Organoids were washed using PBS or fresh media and iCSF samples were collected by mouth-pipetting with a glass microcapillary. Organoid fluid and media were centrifuged at 500 g for 5 min to remove dead cells and debris and subsequently analysed via mass spectrometry. Polyacrylamide gel slices (1-2 mm) containing the purified proteins were prepared for mass spectrometric analysis using the Janus liquid handling system (PerkinElmer, UK). Briefly, the excised protein gel pieces were placed in a well of a 96-well microtitre plate and destained with 50% v/v acetonitrile and 50 mM ammonium bicarbonate, reduced with 10 mM DTT, and alkylated with 55 mM iodoacetamide. After alkylation, proteins were digested with 6 ng/μL endoproteinase Asp-N (Promega, UK) overnight at 37° C. The resulting peptides were extracted in 2% v/v formic acid, 2% v/v acetonitrile. The digest was analysed by nano-scale capillary LC-MS/MS using an Ultimate U3000 HPLC (Thermo Scientific Dionex, San Jose, USA) to deliver a flow of approximately 300 nL/min. A C18 Acclaim PepMap100 5 μm, 100 μm×20 mm nanoViper (Thermo Scientific Dionex, San Jose, USA), trapped the peptides prior to separation on a C18 Acclaim PepMap100 3 µm, 75 µm×250 mm nanoViper (ThermoScientific Dionex, San Jose, USA). Peptides were eluted with a 60 min gradient of acetonitrile (2% to 80%). The analytical column outlet was directly interfaced via a nano-flow electrospray ionisation source, with a hybrid quadrupole orbitrap mass spectrometer (Q-Exactive Plus Orbitrap, ThermoScientific, San Jose, USA). Data dependent analysis was carried out, using a resolution of 30,000 for the full MS spectrum, followed by ten MS/MS spectra. MS spectra were collected over a m/z range of 300-2000. MS/MS scans were collected using a threshold energy of 27 for higher energy collisional dissociation (HCD). LC-MS/MS data were then searched against a protein database (UniProt KB) using the Mascot search engine programme (Matrix Science, UK) (5). Database search parameters were set with a precursor tolerance of 10 ppm and a fragment ion mass tolerance of 0.8 Da. One missed enzyme cleavage was allowed and variable modifications for oxidized methionine, carbamidomethyl cysteine, pyroglutamic acid, phosphorylated serine, threonine and tyrosine, and methyl arginine were included. MS/MS data were validated and emPAI values were calculated using the Scaffold programme (Proteome Software Inc., USA) (6). In order to compare corresponding proteins across samples of different species, only the highest emPAI value was considered as the peptide count for a given protein for each sample. Thus, for example, only the human TTR emPAI value was taken for the human samples (organoids and human adult CSF), while bovine TTR emPAI value was taken for the fetal bovine CSF, and mouse TTR emPAI value for the mouse embryonic CSF. This enabled us to compare corresponding homologous proteins across the samples despite their different accession numbers.

NMR Sample Preparation and Analysis

For NMR experiments, ChP organoids were incubated in complete IDM+A media without phenol red and 1:50 Geltrex (Gibco, A14132-02) for 2 h, 12h, 24 h, 48h or 72h. Organoid media and iCSF were collected and centrifuged at 500 g for 5 min to remove debris. $^1$H-NMR spectra were acquired using a Bruker Ultrashield 400 Plus operating at 400.1 MHz. Samples consisting of $H_2O/D_2O$ mixtures were analyzed using HOD suppression to collect $^1$H-NMR data. Chemical shifts (6) are shown in ppm. The yields of conversion were determined by relative integration of the signals in the $^1$H-NMR spectra. Data analysis was performed using MestReNova (version 7.0) and GraphPad Prism (version 7.0b).

For comparison between in vitro and in vivo levels of small molecules in CSF, in vivo unbound CSF to blood plasma ratio, $K_{p,uu,CSF}$, was calculated as the ratio of the unbound drug in CSF ($C_{u,CSF}$) to that in blood plasma ($C_{u,p}$) similar to previously described (7) (eq A).

$$K_{p,uu,CSF} = \frac{C_{u,CSF}}{C_{u,p}} \quad (A)$$

The amount of unbound drug in each of CSF and plasma is the product of the total drug concentration ($C_p$) or ($C_{CSF}$) and the fraction of drug that is unbound ($f_{u,p}$) or ($f_{u,CSF}$)(eqs B and C).

$$C_{u,p} = C_p f_{u,p} \quad (B)$$

$$C_{u,CSF} = C_{CSF} f_{u,CSF} \quad (C)$$

$C_p$, $C_{CSF}$, and $f_{u,p}$ were taken from literature (Table S2). However, because of the difficulty in obtaining large amounts of CSF, for most drugs $f_{u,CSF}$ is not known. Therefore, $f_{u,CSF}$ was calculated from $f_{u,p}$ where drug-protein dissociation was taken to be the same in plasma and CSF (eq D), correcting for the decreased plasma protein content of CSF by taking the albumin CSF to plasma ratio ($Q_{alb}$) as 0.005 as previously reported in humans.

$$f_{u,CSF} = \frac{1}{1 + Q_{alb}\left(\frac{1}{f_{u,p}} - 1\right)} \quad (D)$$

Because the NMR measurements of in vitro fluids detected unbound drug, the ratio ($K_{m,uu,iCSF}$) was a simple function of the ratio of drug in in vitro CSF ($C_{u,iCSF}$) to drug in media ($C_{u,m}$) (eq E).

$$K_{m,uu,iCSF} = \frac{C_{u,iCSF}}{C_{u,m}} \quad (E)$$

Example 1

As previously reported, cerebral organoids are characterized by intrinsic self-organisation with more recent protocols giving rise predominantly to forebrain identities (13, 14) which also includes ChP epithelium (FIG. 7A) (9, 13). Therefore, in order to study the development of human ChP we established a protocol based upon the cerebral organoid method to generate ChP in a reliable and reproducible manner.

In vitro derivation of ChP cells using the dorsalising factor Bmp4 both alone (15) and in combination with the Wnt-activator molecule CHIR (16) has been reported before.

Figure 7:
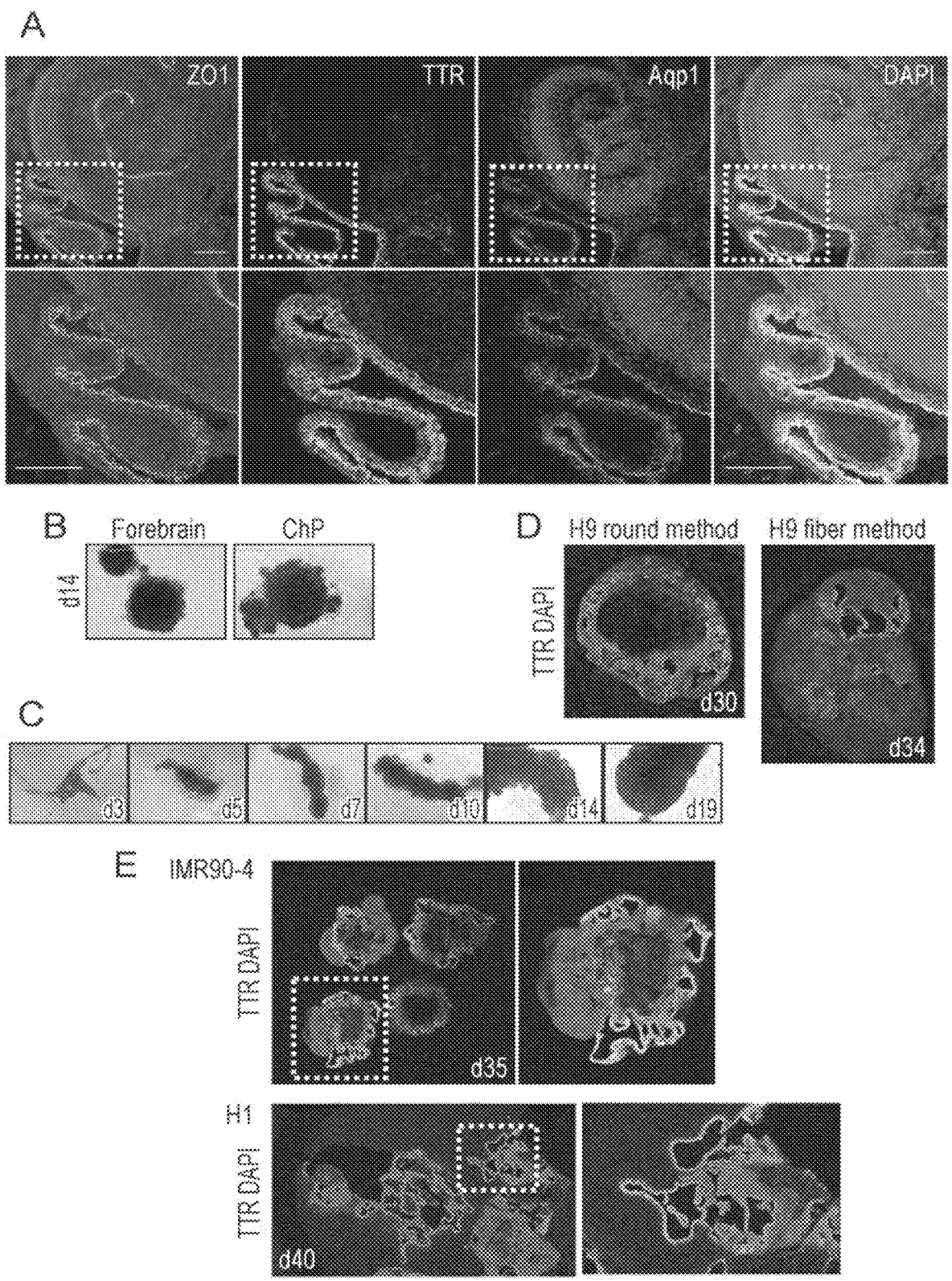
FIG. 7. (A) Confocal images of a forebrain organoid with a convoluted, cuboidal ChP epithelium staining positive for the markers TTR, ZO1 and Aqp1. Scale bar: 100 µm. (B) Comparison of treated, ChP organoids versus untreated, forebrain organoids at day 14. Arrowheads point to the elongated neuroepithelial buds in early treated ChP organoids. Scale bar: 1 mm. (C) Bright field images of different stages of the protocol using the fiber seeding method. Scale bar 1000 µm. (D) Representative confocal images of H9 ChP organoids generated using the round and the fiber method, at day 30 and 34 respectively. Scale bar: 500 µm. (E) Representative confocal images of iPSC IMR90-4 organoids at day 35 and of H1 organoids at day 40, treated with BMP4 and CHIR at day 10. ChP tissue in the organoids is stained for TTR (green, anti-sheep Alexafluor 488) and nuclei are visualized with DAPI. Scale bar: 1000 µm (crop: 500 µm).

Therefore, to promote ChP fate in cerebral organoids, Bmp4 and CHIR were given as a pulse starting at day 10 of the improved cerebral organoid protocol (see Methods) (FIG. 1A, 7B, 7C) (7, 9, 13). At day 14, undirected forebrain organoids developed large, rounded neuroepithelial lobes whereas in Bmp4/CHIR treated organoids we observed more elongated neuroepithelial tissues (FIG. 7B). This observation is consistent with the in vivo development of the ChP from the neuroepithelium of the dorsal midline which progressively becomes more elongated and expands in the lumen of the cerebral ventricles (1, 17, 18). Compared to forebrain organoids, which predominantly developed large lobes with dorsal cortex identity (FIG. 1B, 1C), ChP organoids appeared almost entirely enriched in ChP cuboidal epithelium (FIG. 1B, 1C). Comparison of histological sections of ChP organoids at 40 days with human embryonic ChP at 15 weeks post conception and with ChP from embryonic mouse brain at E18.5 showed a close resemblance in complexity and organization between the human embryonic sample and the organoid tissue (FIG. 1D).

In vivo, ChP epithelium initially develops as a pseudostratified epithelium, followed by an intermediate columnar stage, and maturing into a highly folded cuboidal epithelium (1, 18, 19). To confirm tissue specificity, we performed staining for the ChP marker TTR, the neural stem cell marker Sox2 and the tight junction marker ZO1 at early and late time points (FIG. 1E, FIG. 1F). ChP organoids treated with Bmp4 and CHIR developed a pseudostratified neuroepithelium with TTR positive areas by day 28 (FIG. 1E). By day 39, treated organoids developed a more columnar, polarised ChP epithelium, increasingly enriched in TTR immunostaining, with relatively strong ZO1 expression in cell-cell junctions, and sparse Sox2 immunostaining (FIG. 1F). Quantification of TTR-positive regions showed a reproducible a enrichment in treated organoids compared to untreated controls (FIG. 1G). Together, these data demonstrate a reliable and reproducible generation of ChP tissue in vitro from different lines of human pluripotent stem cells and with two different seeding methods.

Figure 8:
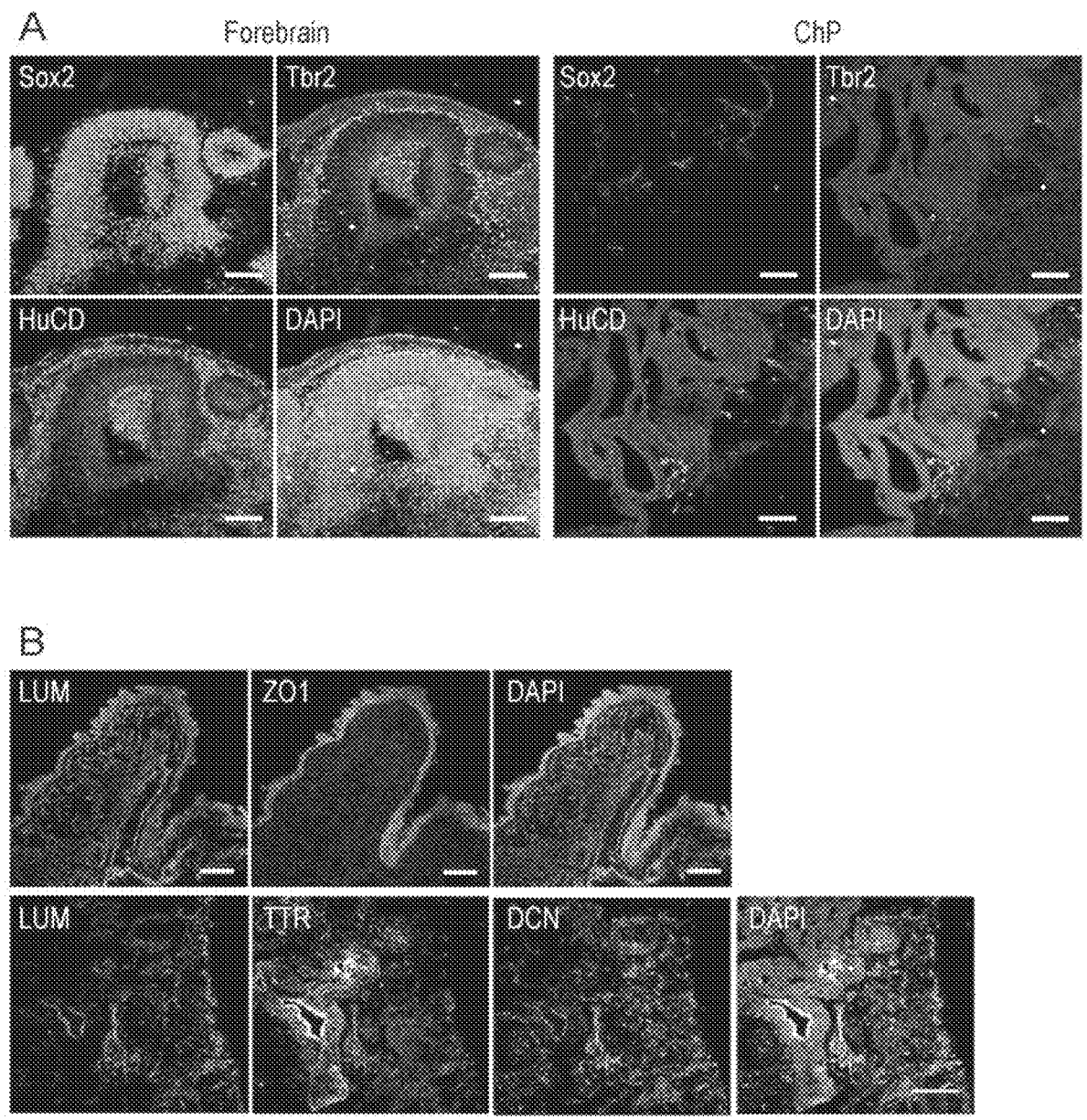
FIG. 8. (A) Representative confocal images of H1 forebrain and ChP organoids stained for Sox2 (magenta, anti-rabbit Alexafluor 568), the cortical intermediate progenitor marker Tbr2 (grey, anti-sheep Alexafluor 647), the neuronal marker HuC/D (green, anti-mouse Alexafluor 488). Scale bar: 100 µm. (B) Representative confocal images of H1 ChP organoids stained for DCN (green, anti-mouse Alexafluor 488), LUM (magenta, anti-rabbit Alexafluor 568), ZO1 (grey, anti-mouse Alexafluor 647), TTR (grey, anti-sheep Alexafluor 647) and DAPI in blue. Scale bar: 100 µm.

The ChP expresses the highest levels in the brain of the channel protein-chloride intracellular channel (CLIC6) (20). We could detect CLIC6 in ChP organoid epithelium both by immunohistochemistry and by immunoblot compared with control, untreated organoids. In parallel, lower levels of forebrain marker Foxg1 were detected in treated organoids compared to controls. Cortex-specific Tbr2 positive intermediate progenitors and HuC/D positive neurons were also largely reduced in early ChP organoids and almost completely absent in mature ChP organoids compared to controls (FIG. 8A).

Figure 2:
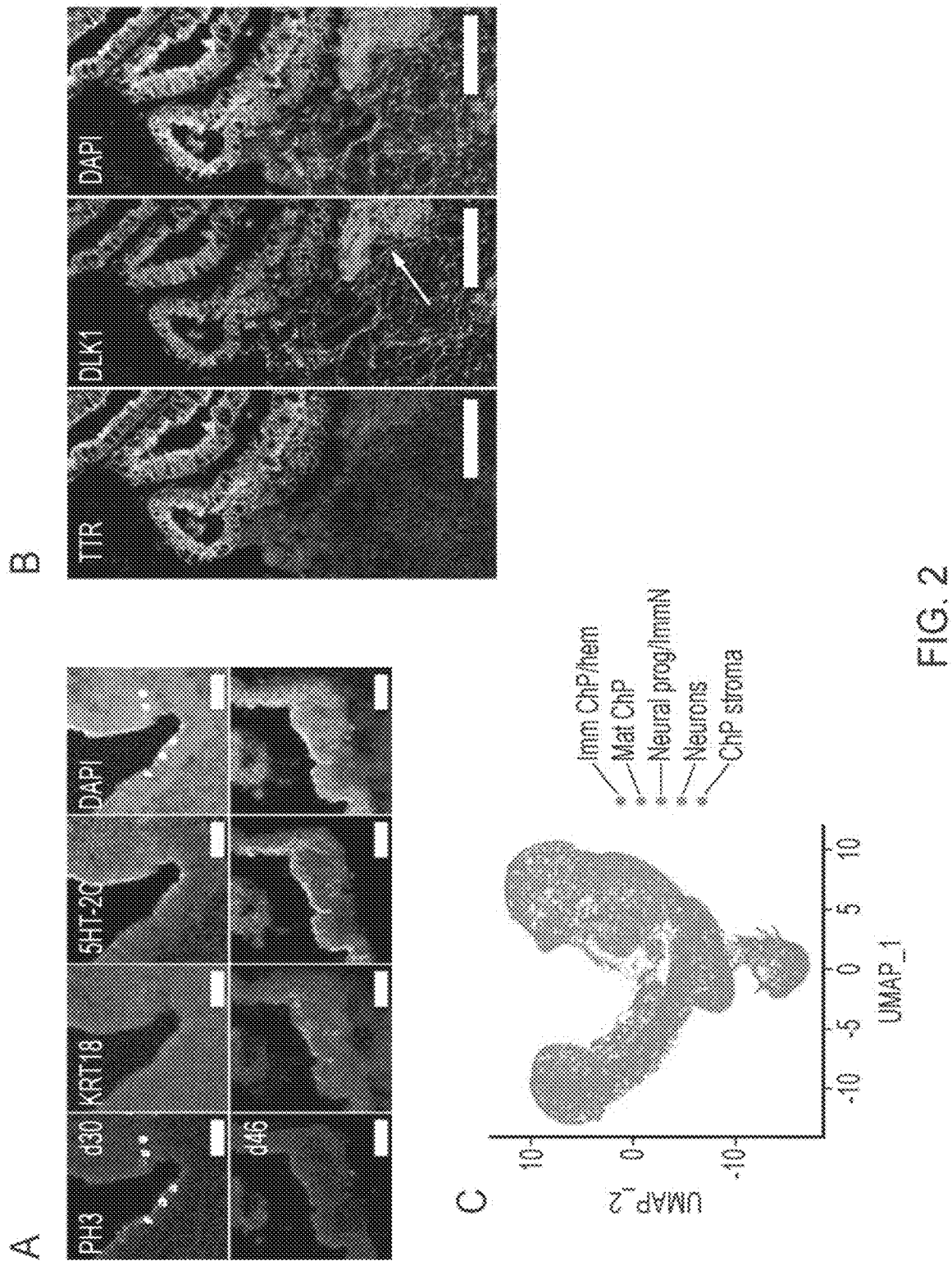
FIG. 2. Organoids reproduce histological features of human choroid plexus. (A) Representative confocal images of H1 organoids at day 30 and 46 stained for Krt18 (green, anti-mouse Alexafluor 488), 5HT-2C (magenta, anti-rabbit Alexafluor 568), PH3 (grey, anti-rat Alexafluor 647) and DAPI in blue. Scale bar: 50 m. (B) Confocal images of ChP epithelium and stromal tissue from organoids staining positive for TTR (magenta) and DLK1 (green, anti-rabbit Alexafluor 488). Scale bar: 100 µm. (C) UMAP showing the population architecture identified by scRNAseq of all combined samples (telencephalic organoid collected at day 55, ChP organoids collected at day 27, 46 and 53). (D) UMAPs showing progressive enrichment in ChP populations in the treated organoids compared to telencephalic organoid. (E) UMAPs showing enrichment of genes involved in ChP development and maturation (CLIC6, HRT2C, MSX1, PAX6), the cortical neuron marker DCX and the stromal marker COL1A1 in the identified scRNAseq clusters. (F) Violin plots showing expression levels of ChP immature/hem (OTX2, RSPO3, PAX6), mature (TTR, KRT18, CA2, NME5, KCNJ13, CA12) and stromal markers (LUM, DCN, DLK1) identified by scRNAseq analysis.
Figure 2:
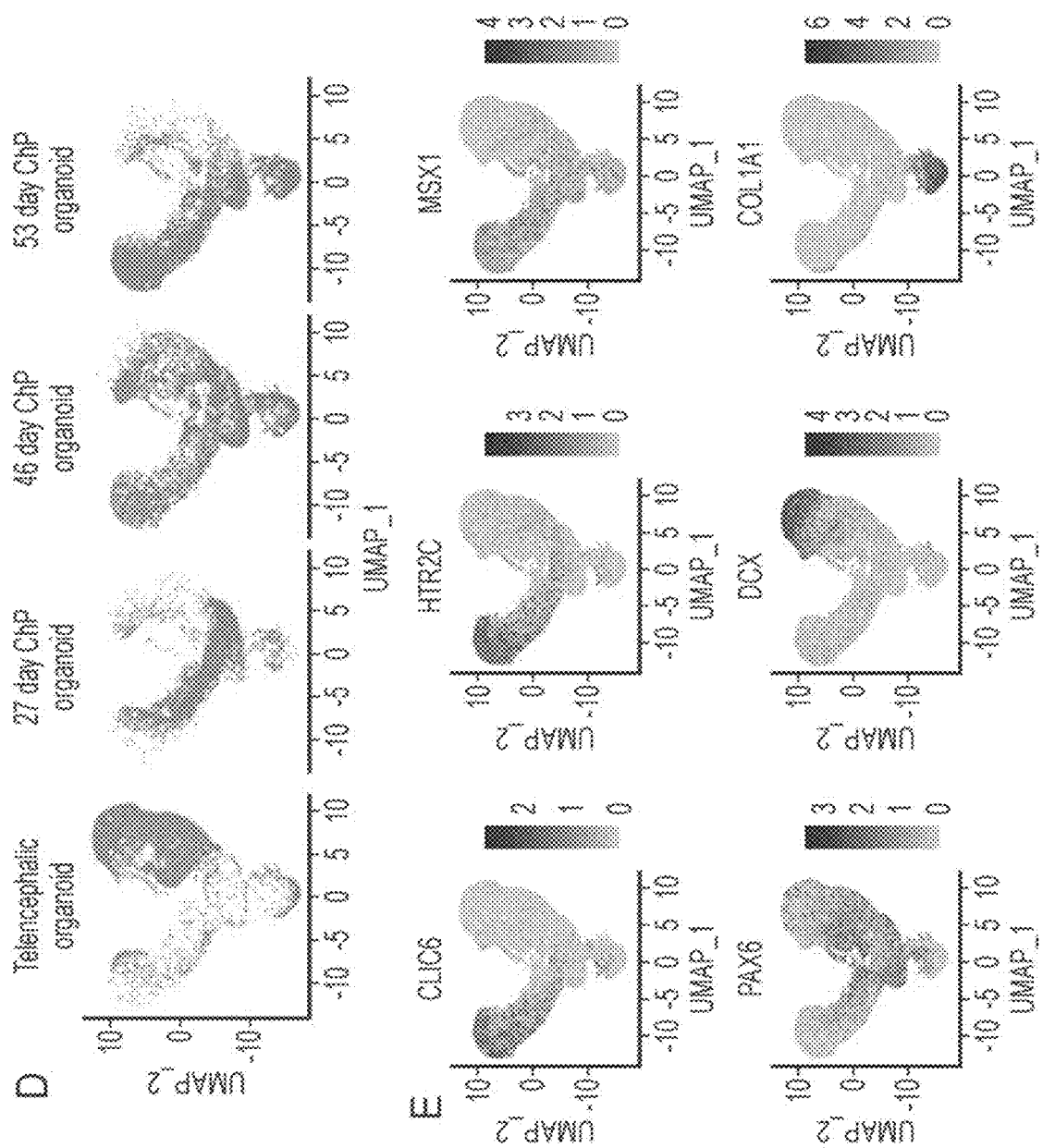
Figure 2:
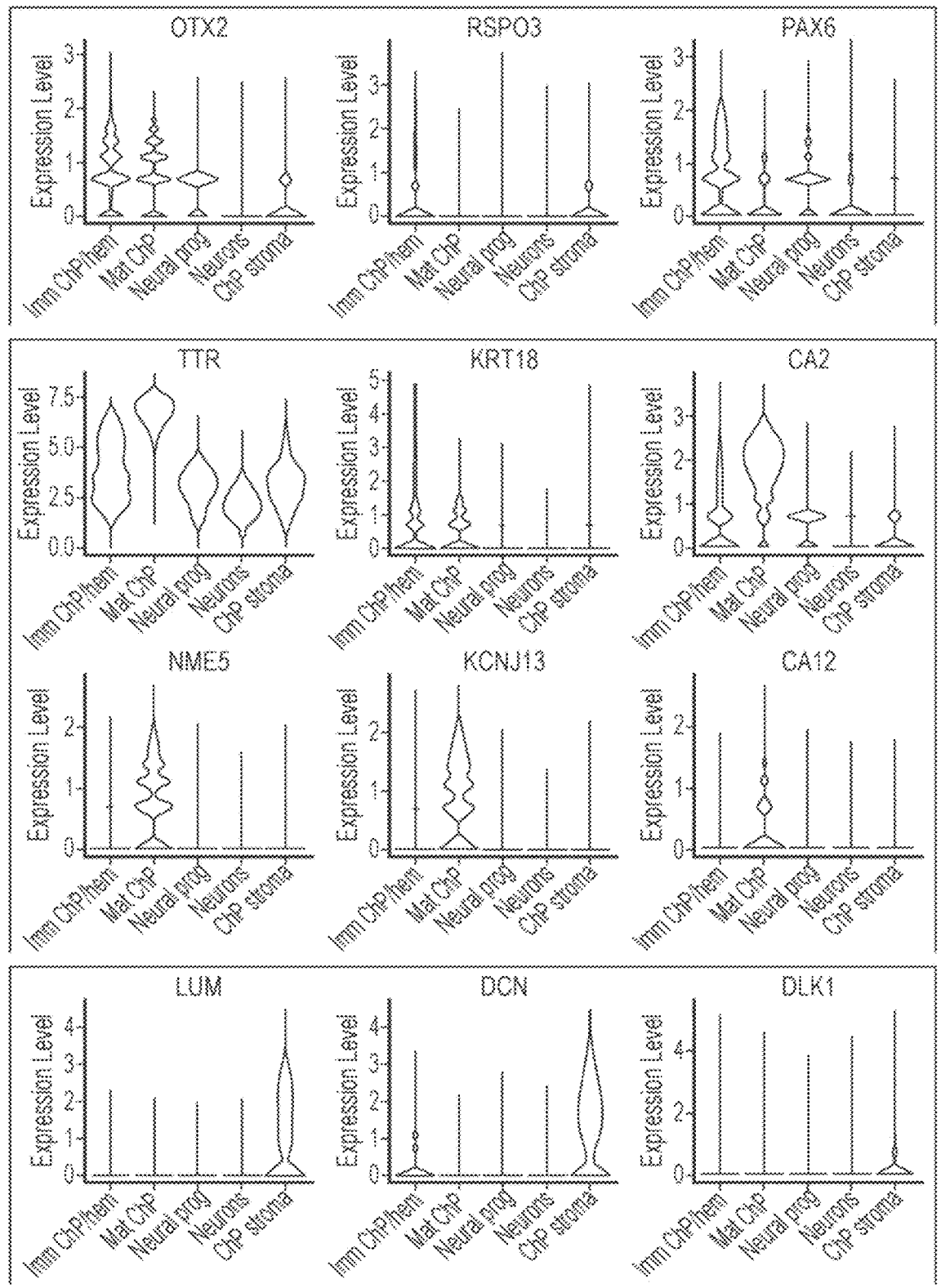

The ChP contains both epithelial and stromal components: the polarized epithelium apically faces the lumen of the ventricle and surrounds a stromal core, exposed to the fenestrated capillaries. To better characterize the different cell populations present in the ChP organoids, we performed single cell RNA-sequencing (scRNA-seq) sampling two organoids from three separate batches of ChP organoids at different maturation stages and two untreated telencephalic organoids as a control (FIG. 2C, FIG. 2). Combined analysis identified the expected clusters of cells expressing markers of neurons and progenitors of neurons in untreated organoids, while immature and mature ChP identities were enriched in ChP organoids (FIG. 2C). Unbiased analysis revealed a consistent and progressive enrichment over time in ChP populations in the treated organoids (FIG. 2D). Older treated organoids displayed a larger component of ChP mature epithelial cells as well as enrichment in the stromal cell population compared to earlier stage organoids and the untreated control (FIG. 2D). Consistent with our previous stainings, we confirmed the expression of CLIC6 and of other specific ChP markers such as the serotonin receptor HRT2C (21) (FIG. 2E). As expected, the immature ChP/hem cluster of cells expressed higher levels of early regulatory factors involved in ChP development such as homeobox protein MSX1, OTX2, R-spondin 3 (RSPO3) and PAX6 (FIG. 2E, FIG. 2F). Mature ChP cell populations expressed higher levels of TTR, carbonic anhydrase 2 and 12 (CA2, CA12), nucleoside diphosphate kinase homolog 5 (NME5), inward rectifier potassium channel 13 (KCNJ13) and of the epithelial marker keratin 18 (Krt18) (FIG. 2F.) A gradient of maturation in the ChP epithelium in vivo, with more mature Krt18 positive cells positioned distally into the lateral ventricle, has been previously reported (21). Krt18 was enriched in more mature ChP organoids compared to early, immature ones (FIG. 2A). To investigate the stromal component of the ChP in our system, we looked at the expression of DLK1 (delta-like noncanonical notch ligand 1), a gene expressed in ChP mesenchyme (21), by immunohistochemistry (FIG. 2B). Expression of DLK1 and of other ChP stromal proteins (lumican, LUM and decorin, DCN) was detected in areas of the organoid surrounding ChP and within the epithelium (FIG. 2B, 8B). In agreement with these results, the ChP stromal population detected by scRNA-seq expressed high levels of DCN, LUM and DLK1 (FIG. 2F), as well as the extracellular matrix component collagen alpha-1 chain 1 (COL1A1) (FIG. 2E). These data suggest that in vitro derived ChP organoids develop both epithelial and stromal components.

Figure 3:
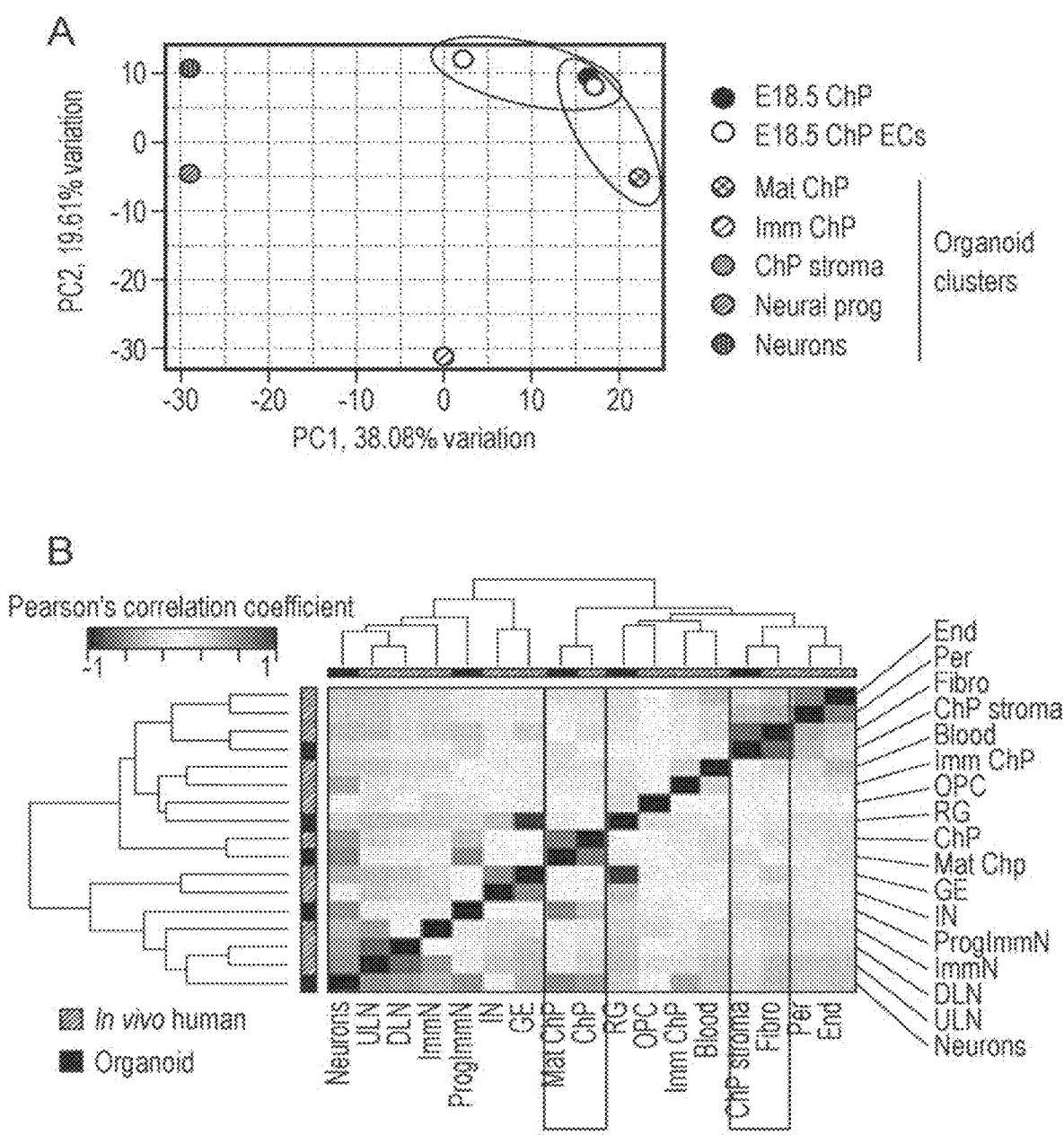
FIG. 3. Choroid plexus organoids develop specialized epithelial features and closely recapitulate genetic architecture of human in vivo tissue. (A) PCA of E18.5 mouse embryonic whole ChP and isolated ChP epithelial cells (ECs) with organoid clusters from scRNA-seq. (B) Pearson's correlation analysis of in vivo human samples with organoid clusters. (C) Color-coded heatmap showing unbiased clustering of organoid with in vivo human samples. (D) Pearson's correlation analysis of mouse, human and organoid samples. (E) Violin plots showing expression levels of regional ChP markers for lateral (LV, LY6E), third (3V, INS) and fourth (4V, PENK) ventricle. (F) Violin plots showing expression of DYNLRB2, FOXJ1 and AQP1 in organoid cell populations identified by scRNAseq. (G) Confocal images of H1 ChP organoids at day 40 and d46 respectively stained for CCDC67 (green, anti-rabbit Alexafluor 488), TTR (grey, anti-sheep Alexafuor 647), Foxj1 (magenta, anti-mouse Alexafluor 568), Arl13b (green, anti-rabbit Alexafluor 488) and DAPI in blue. Scale bar: 50 µm and 100 µm (zoom-in: 20 µm). (H) Confocal images of H1 ChP organoid at day 40 and in vivo ChP from a mouse embryo (E18.5) staining positive for Aqp1 (magenta, anti-rabbit Alexafluor 568) and TTR (green, anti-sheep Alexafluor 488), Nuclei in blue are stained for DAPI. Scale bar: 50 µm. (I) Electron microscopy images showing extensive microvilli on the apical side of ChP epithelium from organoids. Arrowheads indicate cilia (C), tight junctions (TJ), multivesicular bodies (MVB) and extracellular vesicles (Ex). Scale bar: 1 m. (J) Violin plots showing expression levels of APOE, CLU, PLTP in organoid cell clusters identified by scRNAseq. (K) Representative confocal images of H1 organoids at d30 and d46 stained for lipid droplets (LipidTox, grey), TTR (magenta, anti-sheep Alexafluor 568), PH3 (green, anti-rat Alexafluor 488) and DAPI in blue. Scale bar: 50 µm.
Figure 3:
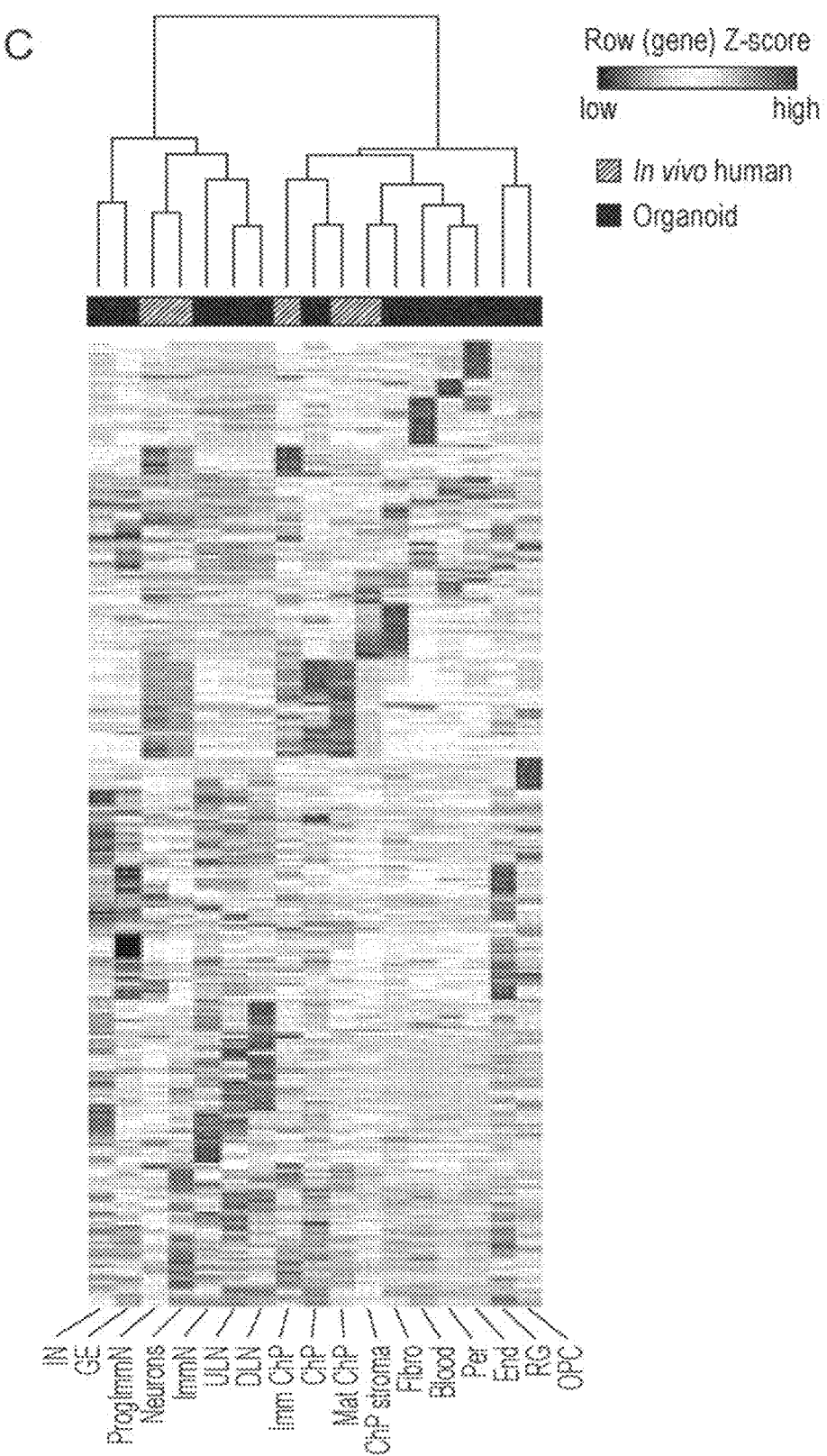
Figure 3:
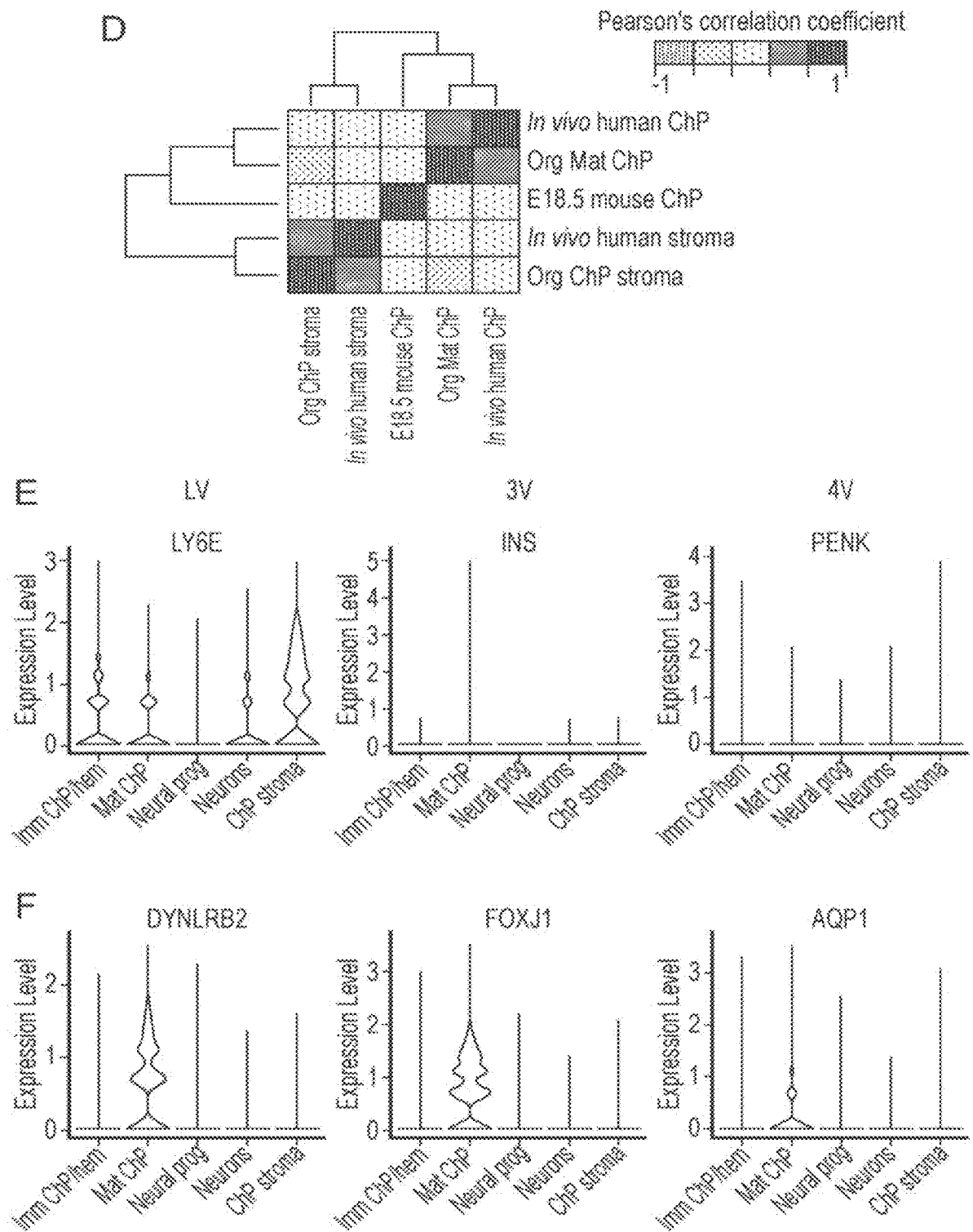
Figure 3:
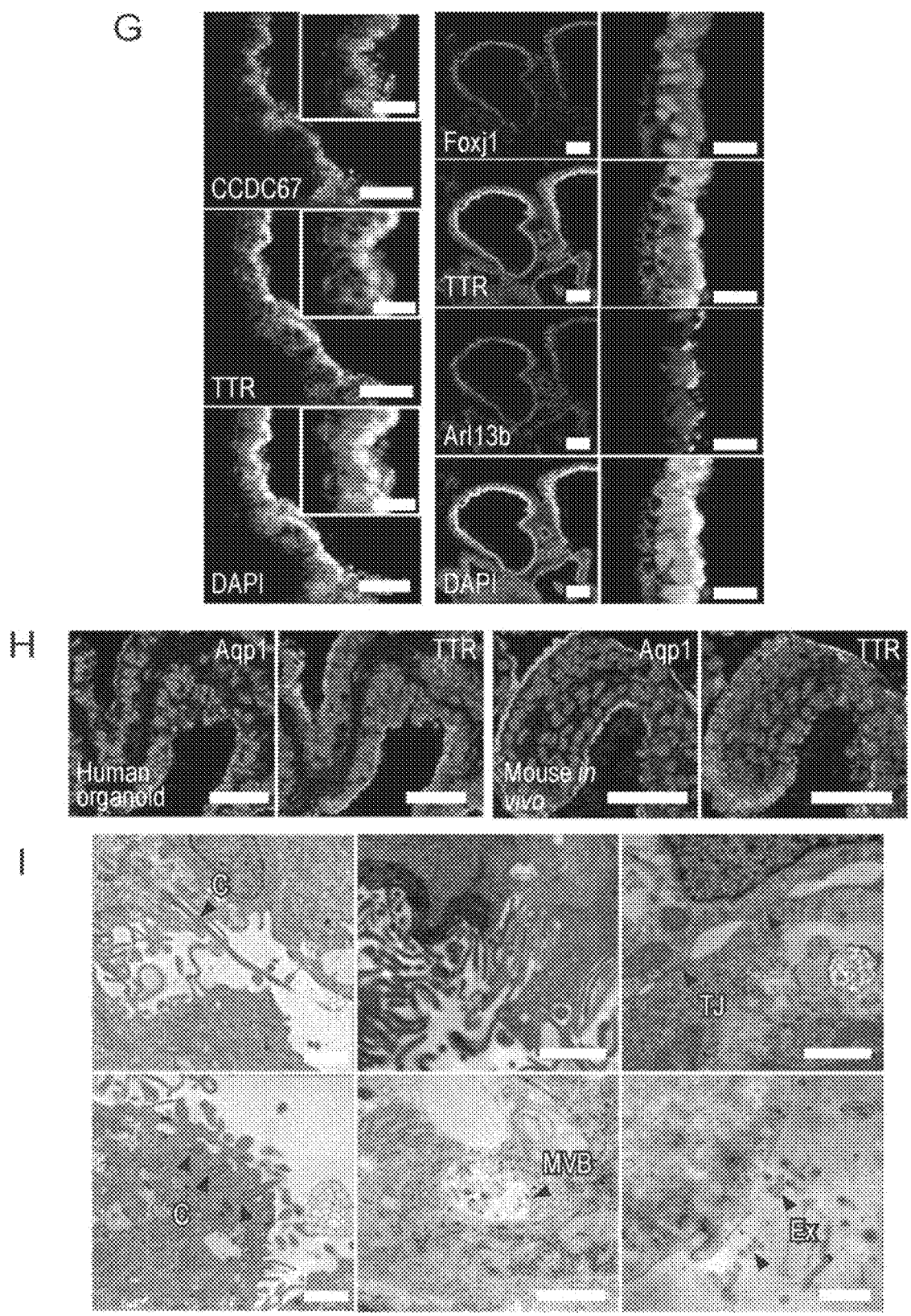
Figure 3:
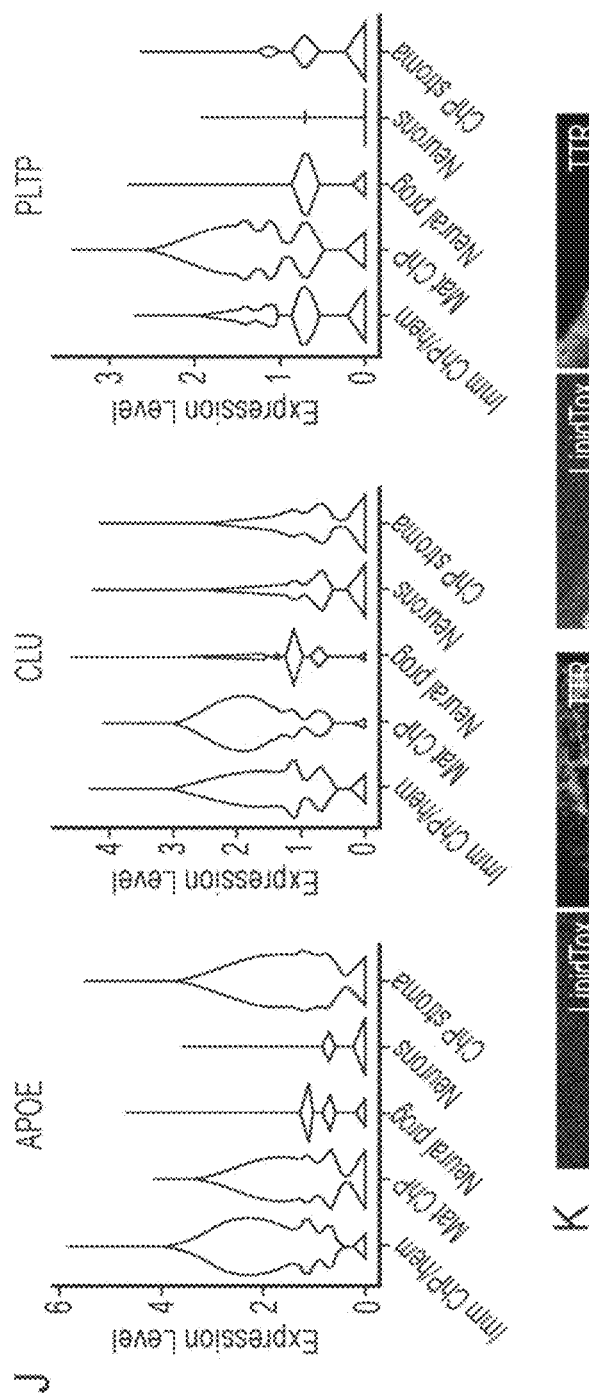
Figure 3:
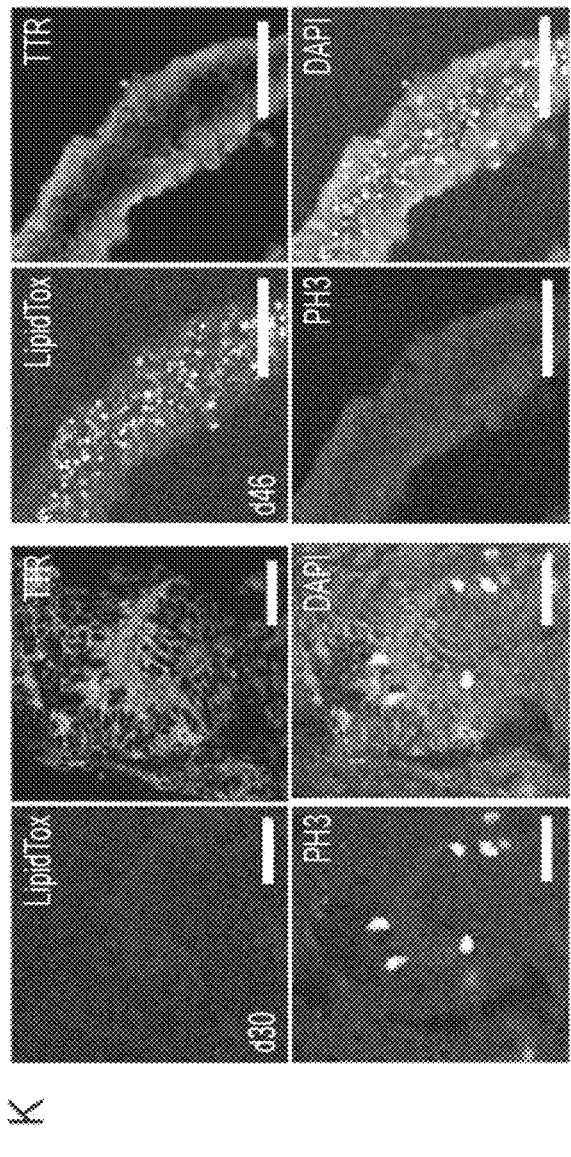

We next sought to identify similarities between our in vitro model and the ChP tissue in vivo. We performed unbiased clustering and principal component analysis (PCA) with published datasets of mouse ChP tissue (1) and developing human brain (2) (FIG. 3A-D). First, we performed PCA between our identified organoid clusters and RNAseq data from in vivo E18.5 mouse embryonic whole ChP and isolated epithelial ChP cells (4). We could observe the closest proximity between ChP from in vivo samples and our mature ChP cluster compared with other identified clusters (FIG. 3A). We then performed correlation analysis between the organoid clusters and those of in vivo human developing brain (22) revealing a high correlation between organoid and in vivo ChP clusters, and between organoid and in vivo stromal clusters (FIG. 3B). Further unbiased hierarchical clustering revealed clustering of organoid mature and immature ChP together with in vivo ChP, and organoid ChP stroma clustering with in vivo stromal identity (FIG. 3C). To further investigate whether our system could better model specifically human ChP, we then compared the organoid mature ChP cluster to both in vivo human and mouse (FIG. 3D) revealing a higher correlation with human ChP than with mouse (FIG. 3D). Finally, examination of specific regional ChP markers (4, 24) revealed the choroid plexus organoids to be of lateral ventricle identity rather than third or fourth ventricle (FIG. 3E) consistent with their telencephalic origin. These data overall demonstrate that the ChP epithelial and stromal composition of the organoids seems to recapitulate the cell composition and genetic architecture of the human ChP in vivo.

To examine the extent of maturation of ChP organoids we looked at previously described markers of ChP maturation. We could observe the presence of ciliary markers, suggested to be expressed during ChP epithelial maturation (3), as well the marker of more mature ChP epithelium aquaporin 1 (AQP1). We could detect an enrichment in cilia genes such as DYNLRB2 and FOXJ1 in the mature ChP cluster, as well as enrichment in AQP1 (FIG. 3F). Staining further revealed the presence of CCDC67 and FOXJ1, both regulators of ciliogenesis, and the ciliary protein ARL13B which stained tufts of apical cilia in the ChP epithelium (FIG. 3G). Staining for AQP1 also confirmed the presence of this more mature marker, showing localization on the apical side of the epithelium, similar to in vivo (FIG. 3H). The ChP epithelium is an extremely efficient secretory machinery (23) with numerous microvilli enhancing its surface area on the apical side, motile cilia and a dense cytoplasmic vesicular network. To further investigate whether ChP organoids recapitulate these fundamental ultrastructural features we performed EM imaging. We observed primary cilia, extensive microvilli apically located, tight junctions between cells, multi-vesicular bodies and numerous extracellular vesicles (FIG. 3I; indicated by arrowheads). In line with its roles in brain lipid metabolism, we also observed an enrichment in lipid droplets, and lipoproteins (ApoE, clusterin/ApoJ, and phospholipid transfer protein PLTP)_(FIG. 3J). These features along with a loss of actively cycling cells positive for the cell cycle marker phosphohistone H3 (PH3) (FIG. 3K), suggest a quite mature secretory epithelium in ChP organoids.

Figure 4:
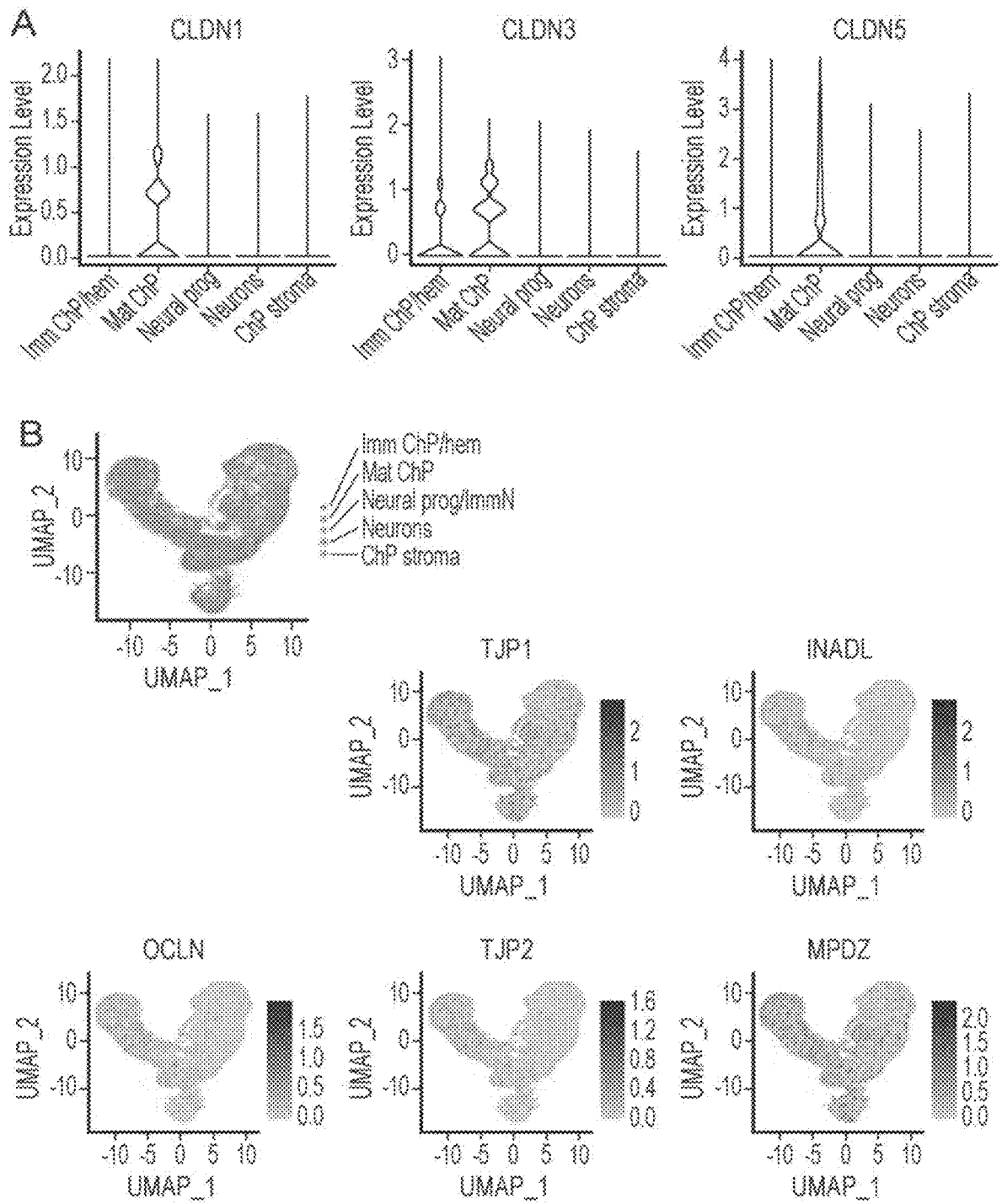
FIG. 4. Choroid plexus organoids develop fluid-filled compartments and form a tight barrier. (A) Violin plots showing expression levels of claudin 1, 3 and 5 in organoid cell clusters identified by scRNAseq. (B) UMAPs showing different organoid populations and enrichment in tight junction proteins in ChP immature and mature clusters. Visualization of tight junction proteins TJP1 and TJP2, occludin (OCLN), INADL and MPDZ. (C) Representative images of human H1 ChP organoids at day 40 staining positive for TTR (magenta, anti-sheep Alexafluor 568), claudin 1 (green, anti-rabbit Alexafluor 488) claudin 3 (green, anti-rabbit Alexafluor 488) claudin 4 (red, anti-mouse Alexafluor 568) and claudin 5 (green, anti-rabbit Alexafluor 488). Nuclei in blue are labeled with DAPI. Scale bar: 50 µm. (D) Representative bright field images of untreated forebrain organoids and of ChP organoids that developed fluid-filled compartments. Scale bar: 1 cm. Zoomed bright field image of a ChP organoid that developed self-contained fluid compartment. Scale bar: 1 mm. (E) Confocal images of the epithelium surrounding the organoid fluid-filled compartment staining positive for ZO1 (grey, anti-mouse Alexafluor 647), TTR (green, anti-sheep 488), Aqp1 (red, anti-rabbit Alexafluor 568). Nuclei are labeled in blue with DAPI. Scale bar: 50 µm.
Figure 4:
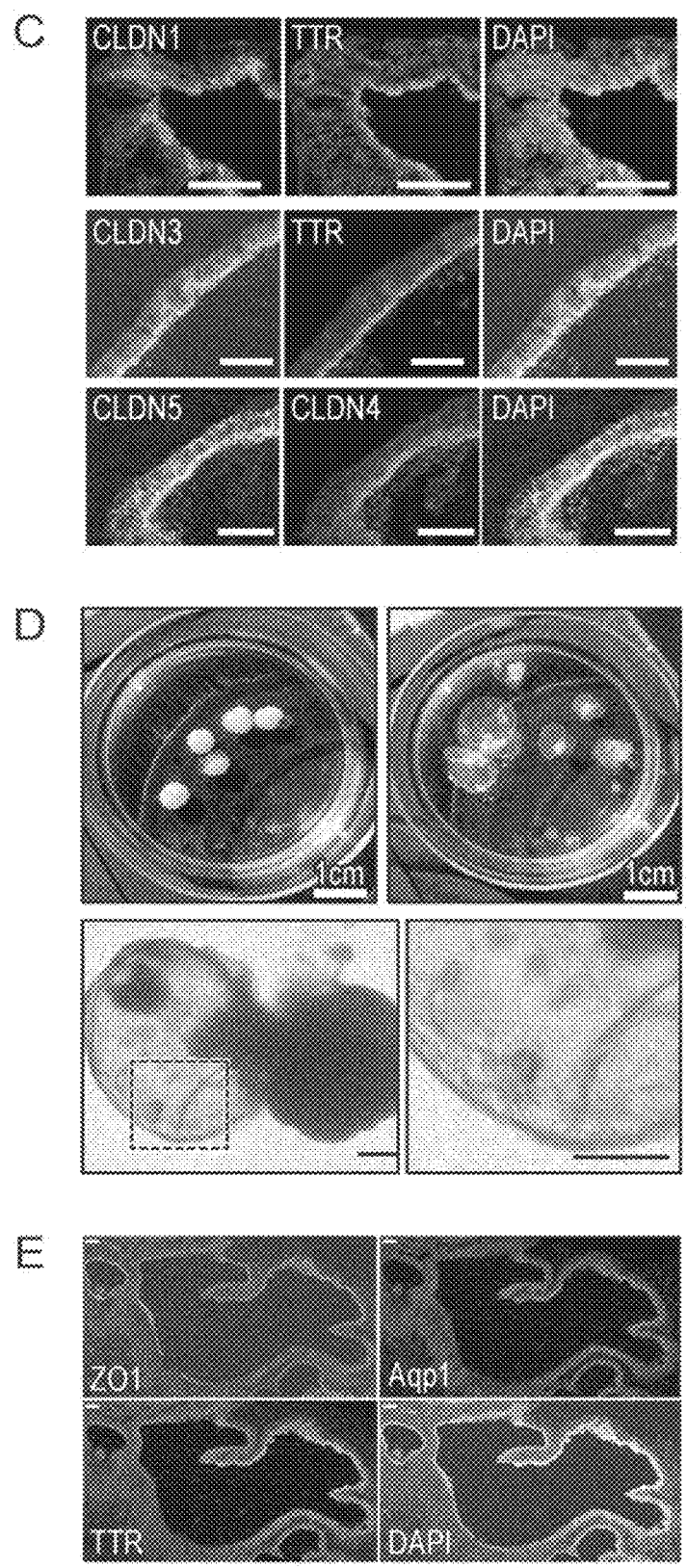
Figure 11:
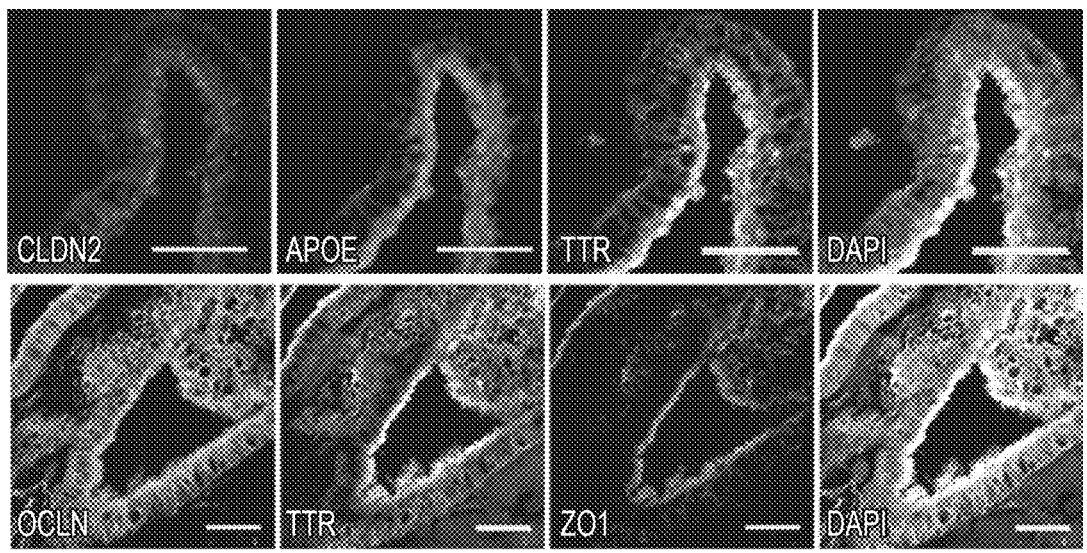
FIG. 11. (A—top) ChP epithelium from human organoids stained for TTR (grey, anti-sheep Alexafluor 647), claudin 2 (green, anti-rabbit Alexafluor 488) and APOE (magenta, anti-mouse Alexafluor 568). Scale bar: 50 µm. DAPI in blue labels the nuclei. (A—bottom) Staining for tight junction marker occludin (green, anti-rabbit Alexafluor 488), TTR (grey, anti-sheep Alexafluor 647), ZO1 (magenta, anti-mouse Alexafluor 568) and DAPI in blue of ChP epithelium from human organoids. Scale bar: 50 µm. (B) Bright field image of ChP organoid with self-contained iCSF fluid, isolated from media incubated for 2 h with 647-Alexafluor labeled 10 kDa-dextran. (C) Fluorescent intensity measured in media and iCSF after 2h incubation with 70 kDa Oregon green-dextran, 10 kDa Alexa 647-dextran and 3-5 kDa FITC-dextran. (D) NMR spectra of Dopa, L-Dopa and control (Ctrl) iCSF measured after 2h incubation.
Figure 11:
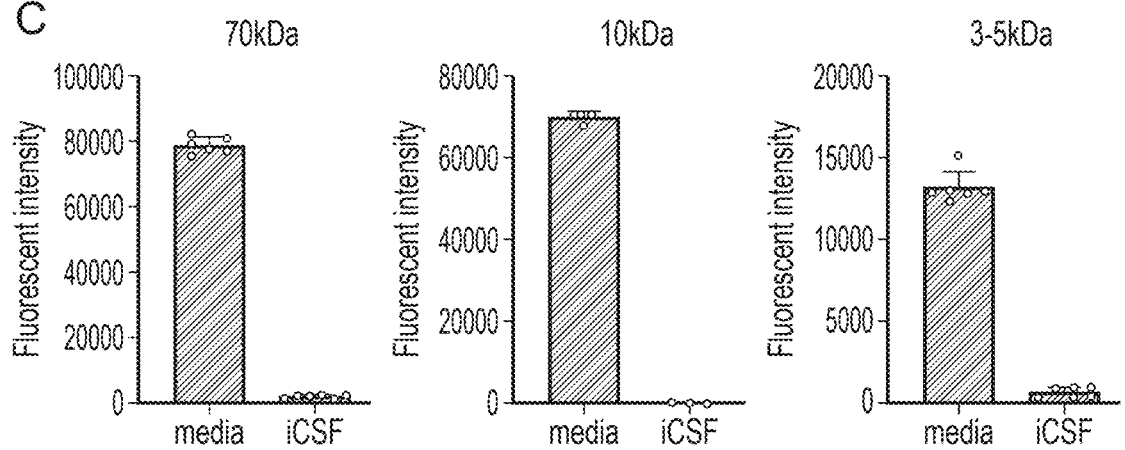
Figure 11:
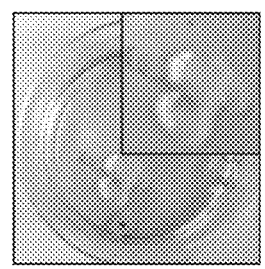
Figure 11:
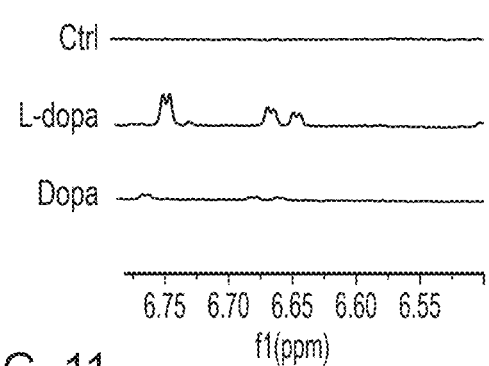
Figure 12:
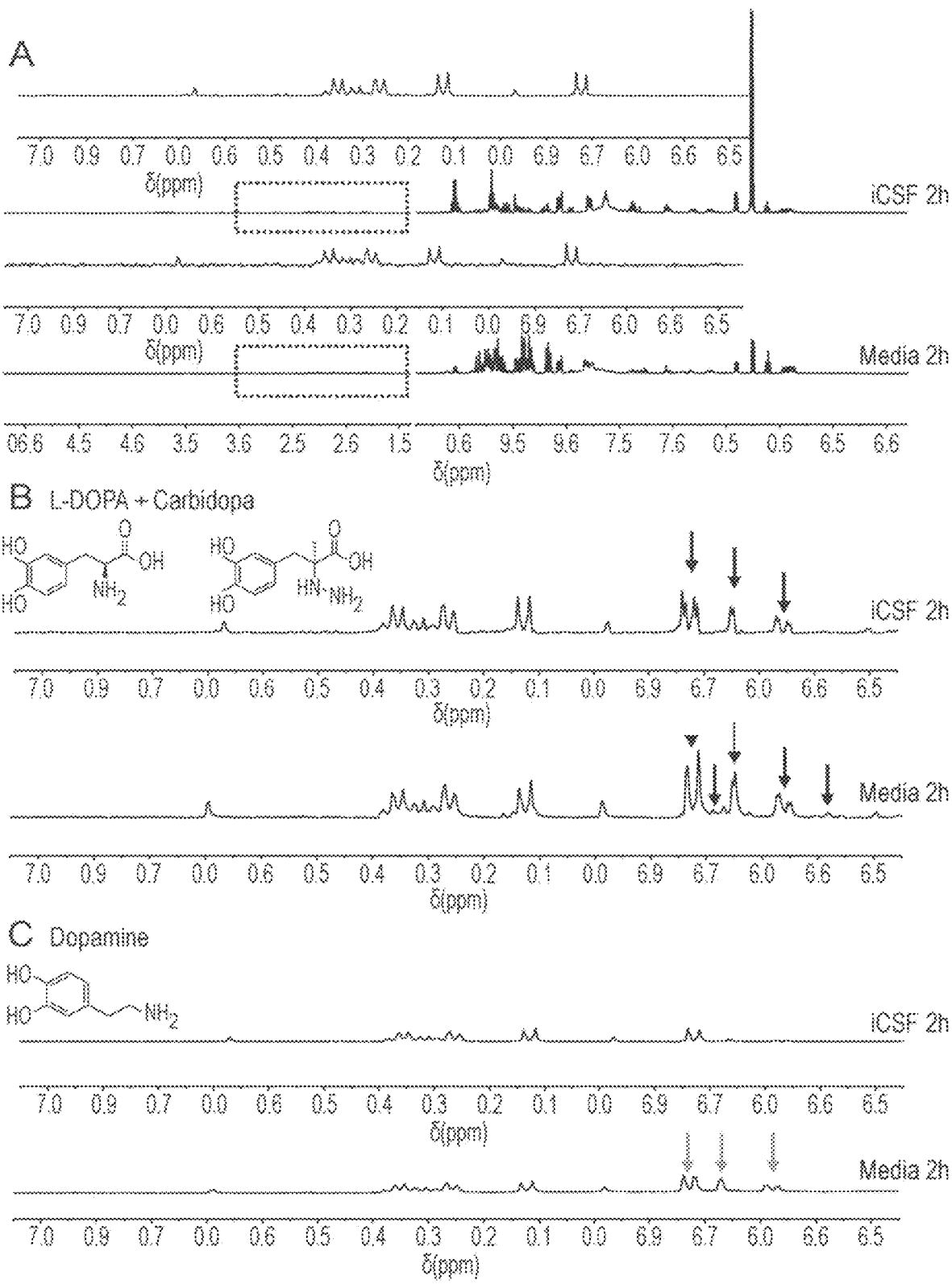
FIG. 12. (A)$^1$H-NMR analysis ($H_2O/D_2O$) of the control samples (media and iCSF). Expansions of the spectra are reported for clarity. (B)$^1$H-NMR analysis ($H_2O/D_2O$) of samples upon incubation with L-Dopa (500 µM) and Carbidopa (500 µM). (C)$^1$H-NMR analysis ($H_2O/D_2O$) of samples upon incubation with Dopamine (500 µM) (500 µM). Arrows indicate the peaks of interest.
Figure 13:
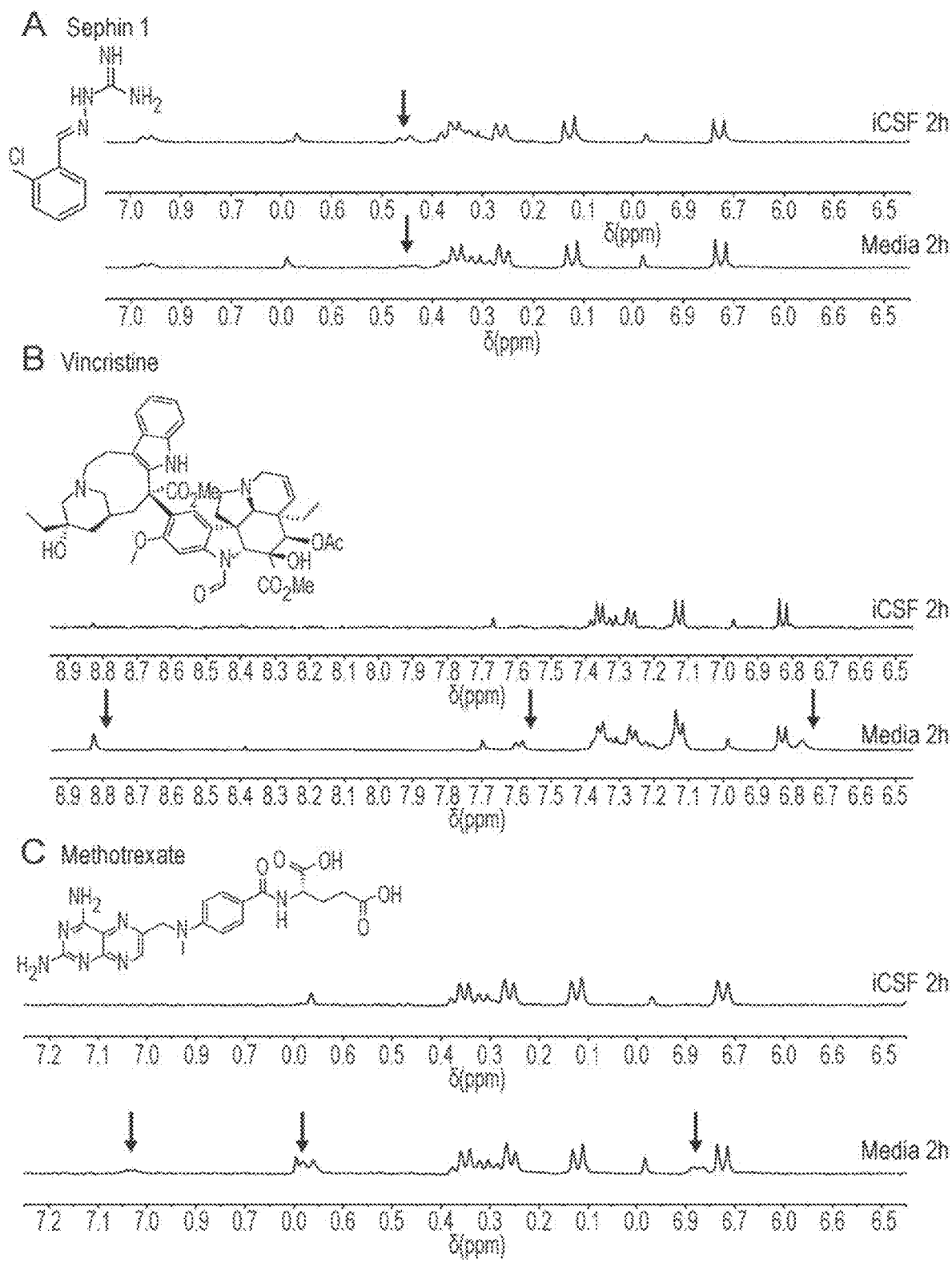
FIG. 13. (A)$^1$H-NMR analysis ($H_2O/D_2O$) of the samples (media and iCSF) upon incubation with (A) Sephin 1 (500 µM), (B) Vincristine (500 µM), (C) Methotrexate (500 µM). Expansions of the spectra are reported for clarity. Arrows indicate the peaks of interest.
Figure 14:
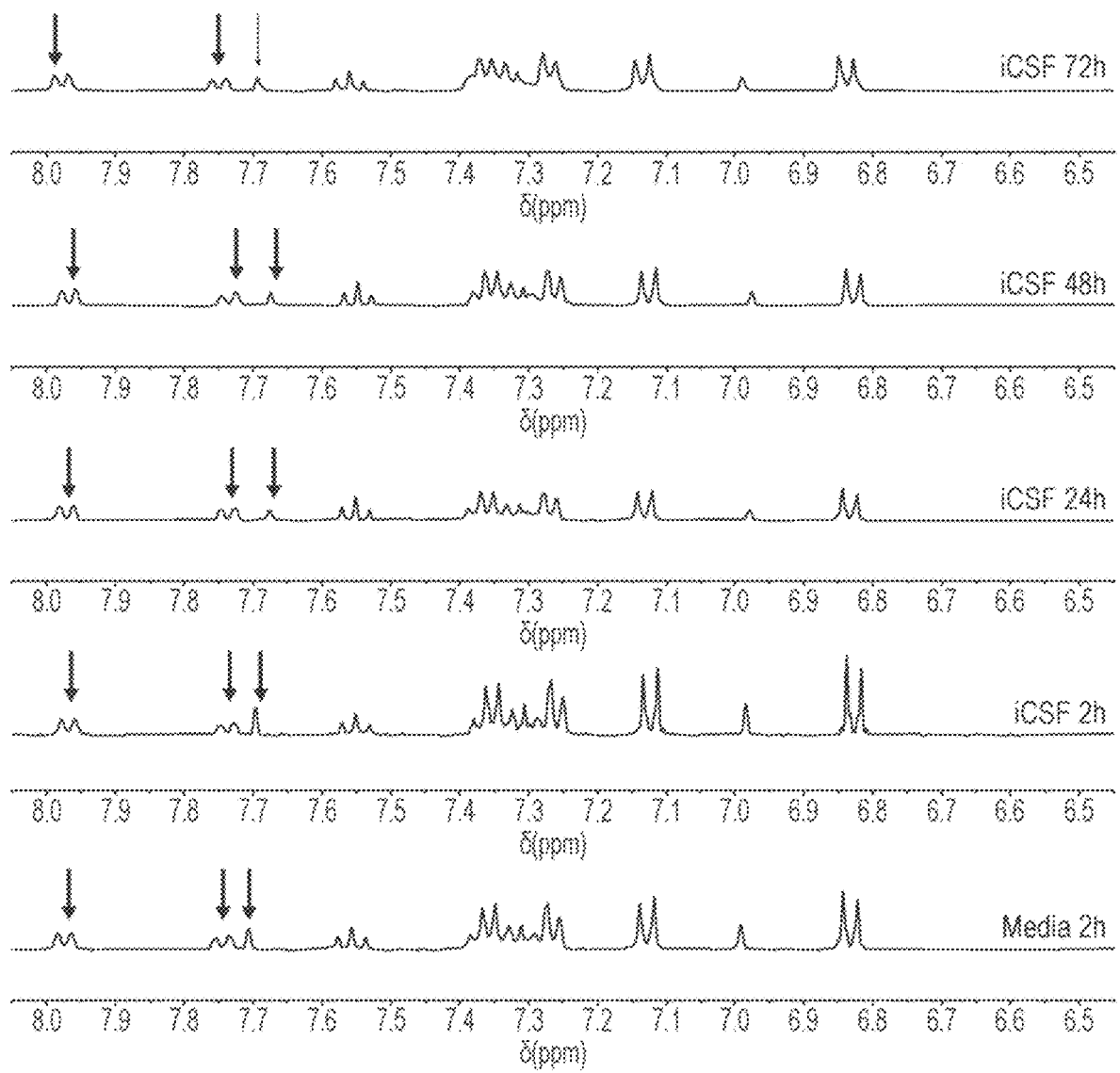
FIG. 14. (A)$^1$H-NMR analysis ($H_2O/D_2O$) of the samples (media and iCSF) upon incubation with Bupropionyl (500 µM). Expansions of the spectra are reported for clarity. Arrows indicate the peaks of interest.
Figure 15:
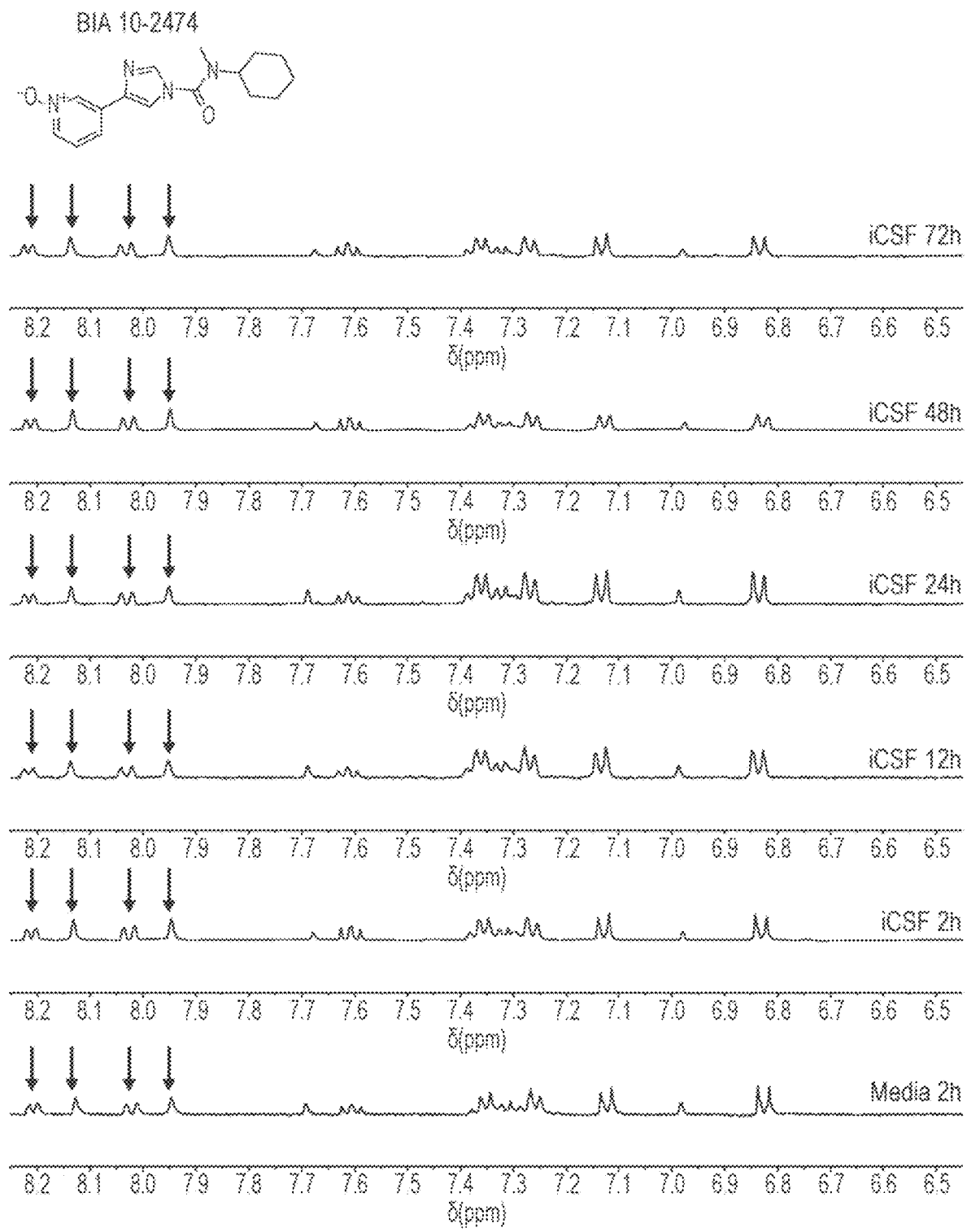
FIG. 15. (A)$^1$H-NMR analysis ($H_2O/D_2O$) of the samples (media and iCSF) upon incubation with BIA10-2474 (500 µM). Expansions of the spectra are reported for clarity. Arrows indicate the peaks of interest.

Next, we asked whether ChP organoids could develop a tight barrier by examining the expression of tight junctions markers such as claudins and occludin which seal the intercellular spaces in between cells of the ChP epithelial barrier (25, 26). The scRNA-seq revealed the presence of several of the claudins (FIG. 4A) as well as other tight junction components occludin (OCLN), ZO1 (TJP1), ZO2 (TJP2), and PDZ proteins PATJ (INADL) and MPDZ (FIG. 4B). Staining revealed apical localization of claudin 1, 3, 4 and 5 in the ChP organoid polarized epithelium and validated their expression enrichment (FIG. 4C). Low levels of claudin 2 were also observed in ChP organoid epithelium as well as the presence of OCLN (FIG. 11A). Finally, to directly assess the barrier function of the ChP epithelium we applied fluorescently labeled dextrans of varying molecular weights (70, 10 and 3-5 kDa) and examined their entry into the organoids. After 2h incubation, no apparent leakage of 10 kDa Alexa-647 labeled dextrans was visible inside the organoid (FIG. 11B). Fluorescent intensity of media and internal fluid collected after 2h incubation with 70 kDa, 10 kDa and 3-5 kDa labeled dextrans confirmed the complete exclusion of these molecules from the organoid (FIG. 11).

Figure 9:
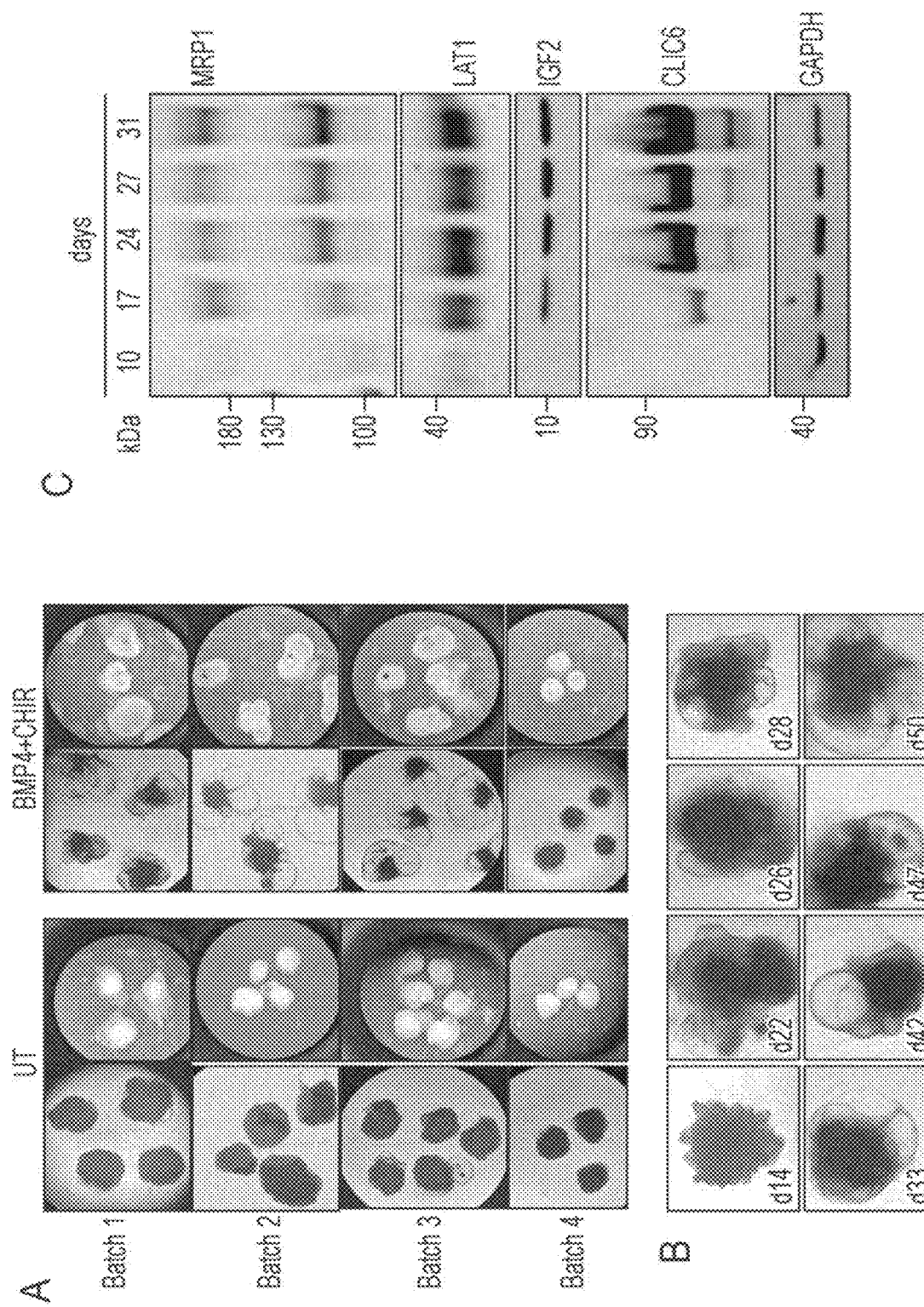
FIG. 9. (A) Representative bright field images of 4 independent batches of H1 untreated and BMP4+CHIR treated organoids (from top to bottom: 57, 54, 46, 40 days). (B) Time course series of images of H1 treated ChP organoids that show development and expansion of iCSF compartments from day 14 to day 50. Scale bar: 1000 µm. (C) Immunoblot for ChP epithelial transporters MRP1, LAT1, CLIC6, secreted protein IGF2, and the loading control GAPDH of ChP organoid lysates from day 10 to day 31.

A striking feature of ChP organoids was the later development of large fluid-filled compartments or cysts containing a colorless liquid, which were rarely present or completely absent in forebrain, untreated organoids (FIG. 4D, FIG. 9A-B). We found that these compartments were completely isolated from the media and could be maintained with continued addition of dissolved Matrigel to the media. We observed the same cuboidal epithelium surrounded these compartments and displaying polarized orientation with apical markers Aqp1 and ZO1 on the luminal side towards the fluid (FIG. 4D).

Figure 5:
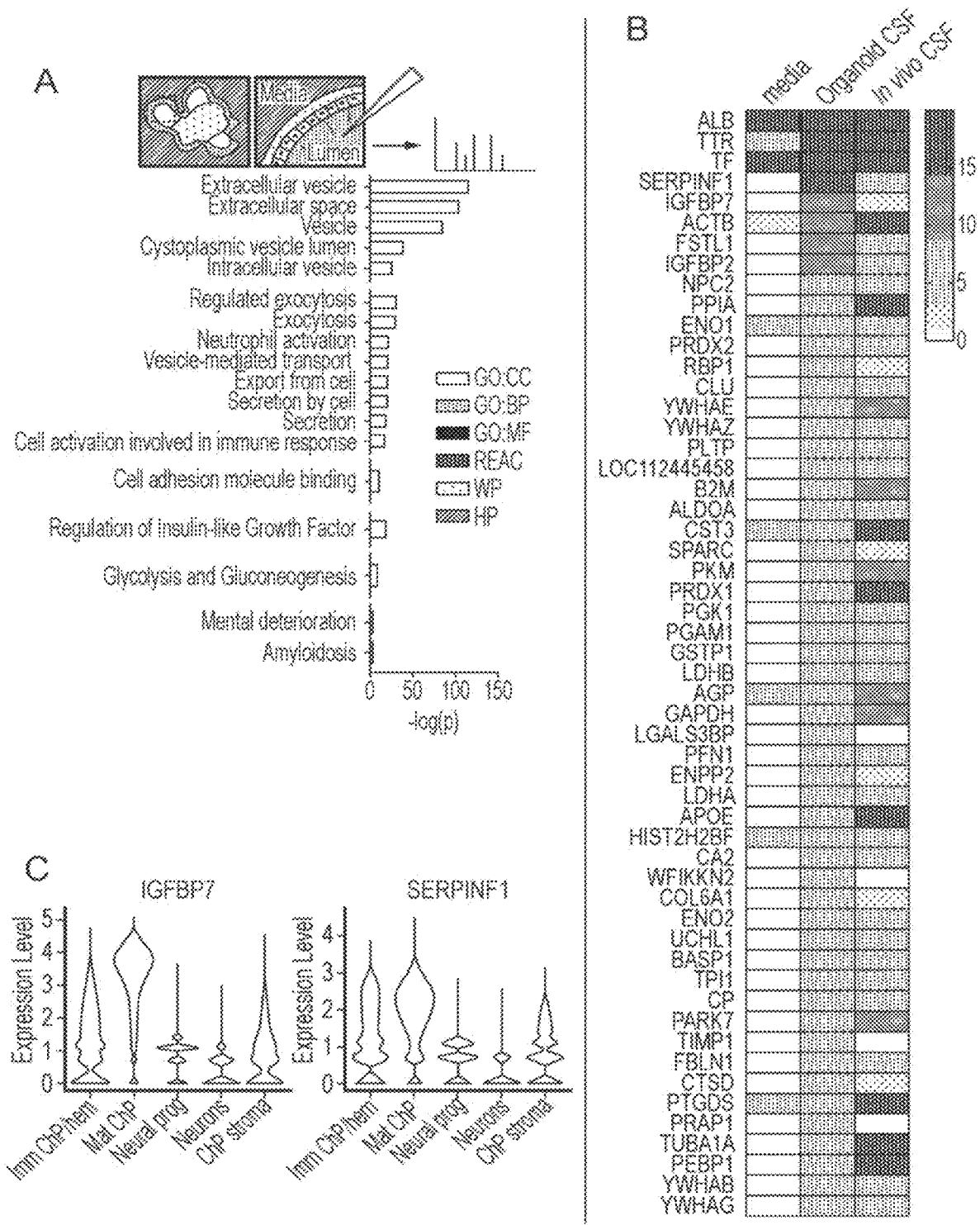
FIG. 5. Human developmental proteins are secreted by choroid plexus organoids. (A) gProfileR analysis of proteins detected in iCSF from at least 2 organoid batches showing significant ($p<0.05$) enrichments for GO categories cellular component (GO:CC), molecular function (GO:MF) and biological process (GO:BP), REAC, WP, HP databases. (B) Color-coded heatmap showing relative abundance (emPAI values) of proteins detected in organoid iCSF from at least two organoid batches (3 H9 batches, one H1 and one iPSCs batch) and their corresponding values in media and in in vivo CSF samples pool which includes human adult CSF (hCSF, telencephalic CSF, n=3 healthy donors, Caltag-Medsystem), bovine fetal CSF (bCSF, BiolVT) and embryonic mouse CSF (msCSF, E12.5-13.5). Values shown are means of proteins with emPAI≥1. (C) Violin plots of secreted proteins IGFBP7 and SERPINF1 expression levels in organoid cell clusters identified by scRNAseq analysis. (D) UMAPs showing enrichments in secreted proteins RBP1, IGF2, NPC2 and the specific transporters SLC23A2 and SLC46A1 in different cell populations identified by organoid scRNAseq. (E) Two color-coded heatmaps (emPAI values): on the top, abundant proteins with an emPAI≥1 detected only in human-derived samples (organoid iCSF and adult hCSF); on the bottom, abundant developmentally related proteins with an emPAI≥1 detected only in organoid iCSF and in embryonic or fetal in vivo CSF. (F) Immunoblot validation of IGF2 and TTR in organoid total lysate from H9 untreated and treated, ChP organoids, media and iCSF from 3 independent batches. (G) Representative confocal images of ChP epithelium from organoids staining positive for IGF2 (green, anti-rabbit Alexafluor 488) and TTR (grey, anti-sheep Alexafluor 647). Nuclei are labeled with DAPI in blue. Scale bar: 100 m. (H) Venn diagram plot of CSF proteins present in human early embryonic (Carnegie stage 20), adult and ChP organoid.
Figure 5:
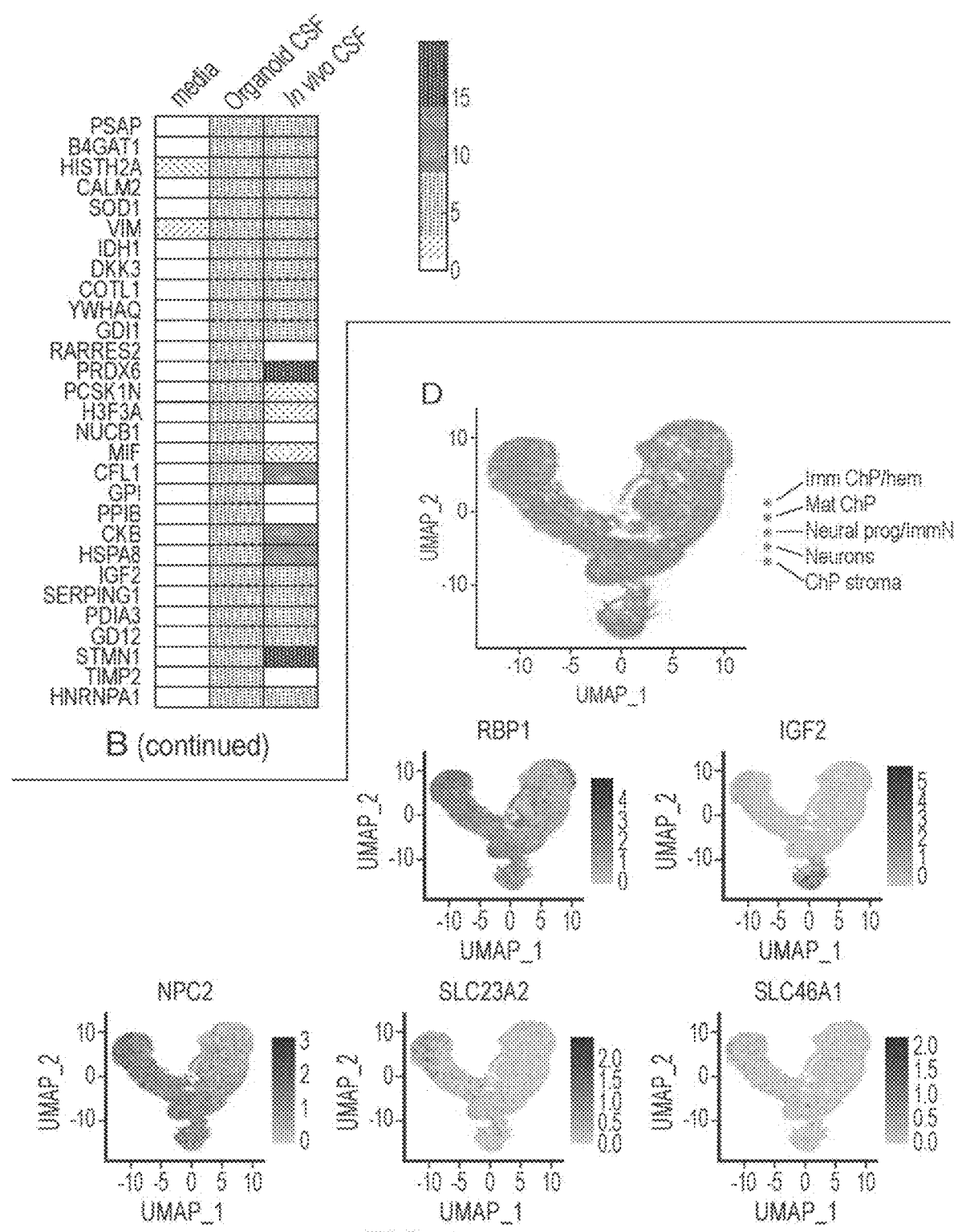
Figure 5:
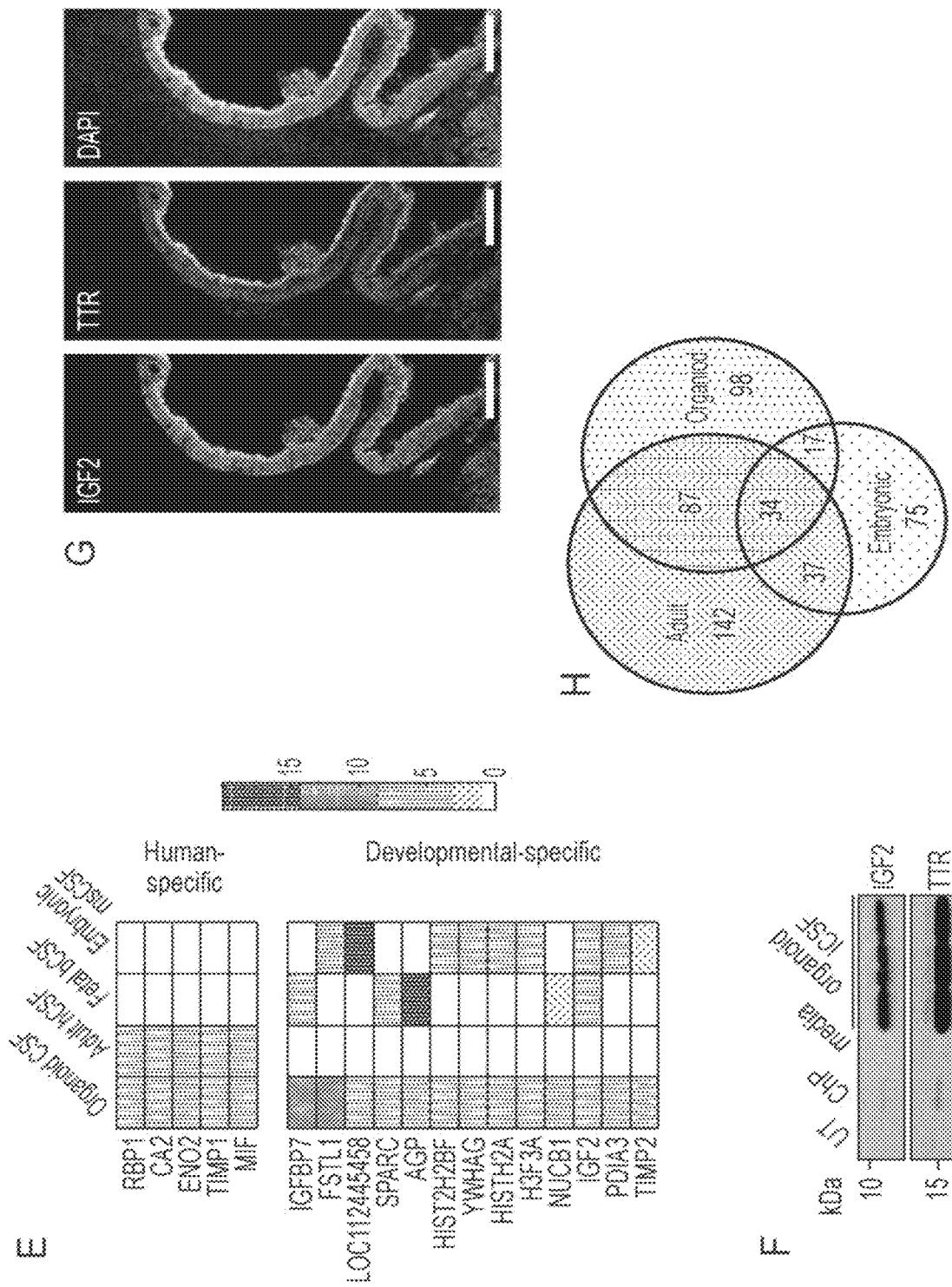
Figure 10:
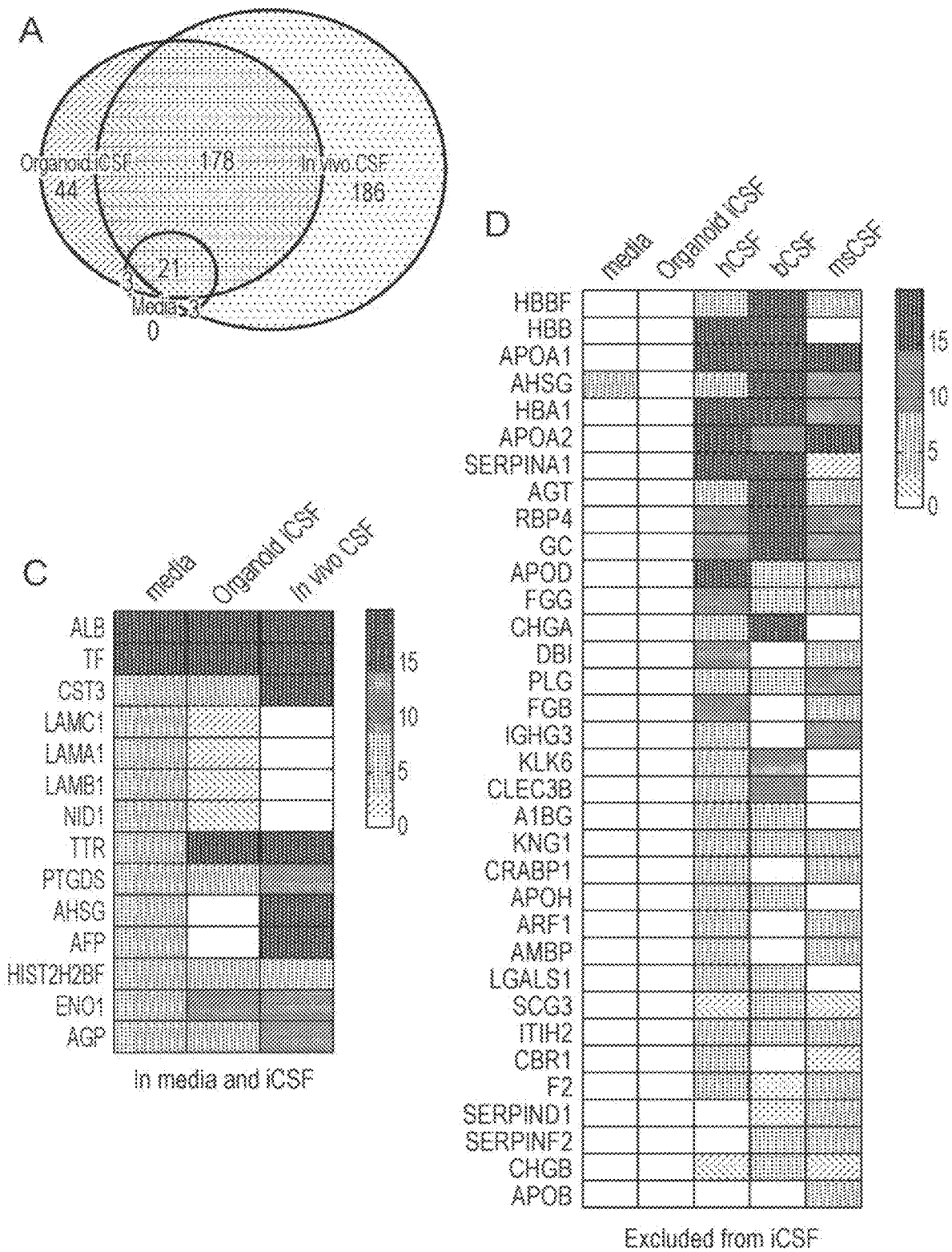
FIG. 10. (A) Venn diagram of proteins detected by mass spectrometry with an emPAI≥1 in at least one sample in media, organoid iCSF and in vivo CSF samples. (B) Color-coded heatmap of the same proteins in FIG. 3E showing all samples analysed by mass spectrometry. Proteins with emPAI≥1 detected in at least two iCSF samples are shown. (C) Color-coded heatmap of abundant proteins (emPAI≥1) excluded or absent from the organoid iCSF, but present in at least two in vivo samples. (D) Color-coded heatmap showing abundant proteins (emPAI≥1) shared between media and iCSF (mean of five samples shown) from at least two organoid batches and the mean of the in vivo CSF samples from human adult CSF (hCSF), bovine fetal CSF (bCSF) and embryonic mouse CSF (msCSF, E12.5-13.5). (F) Histogram showing top categories from gProfileR analysis with significant (p<0.05) enrichment.
Figure 10:
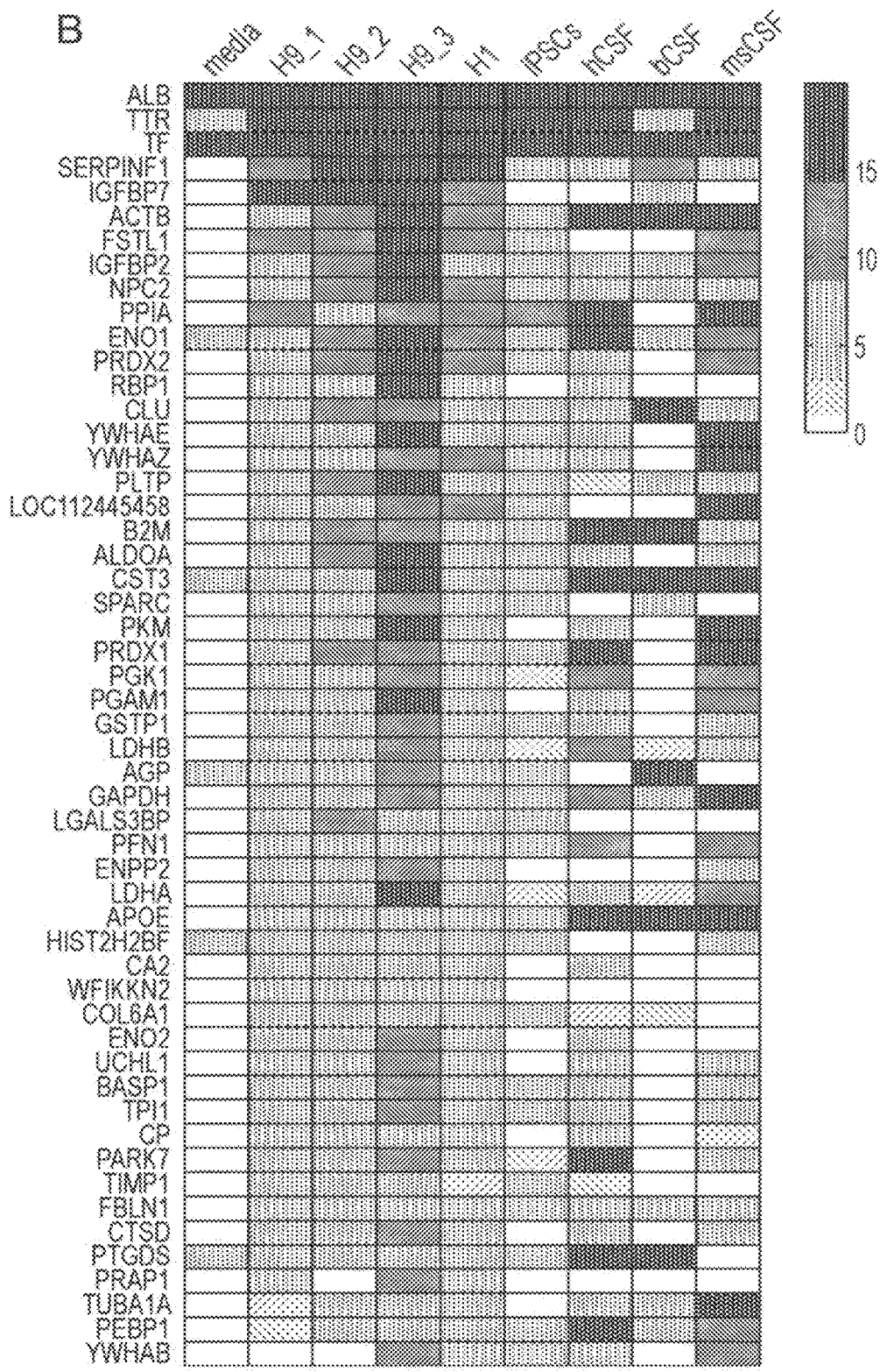
Figure 10:
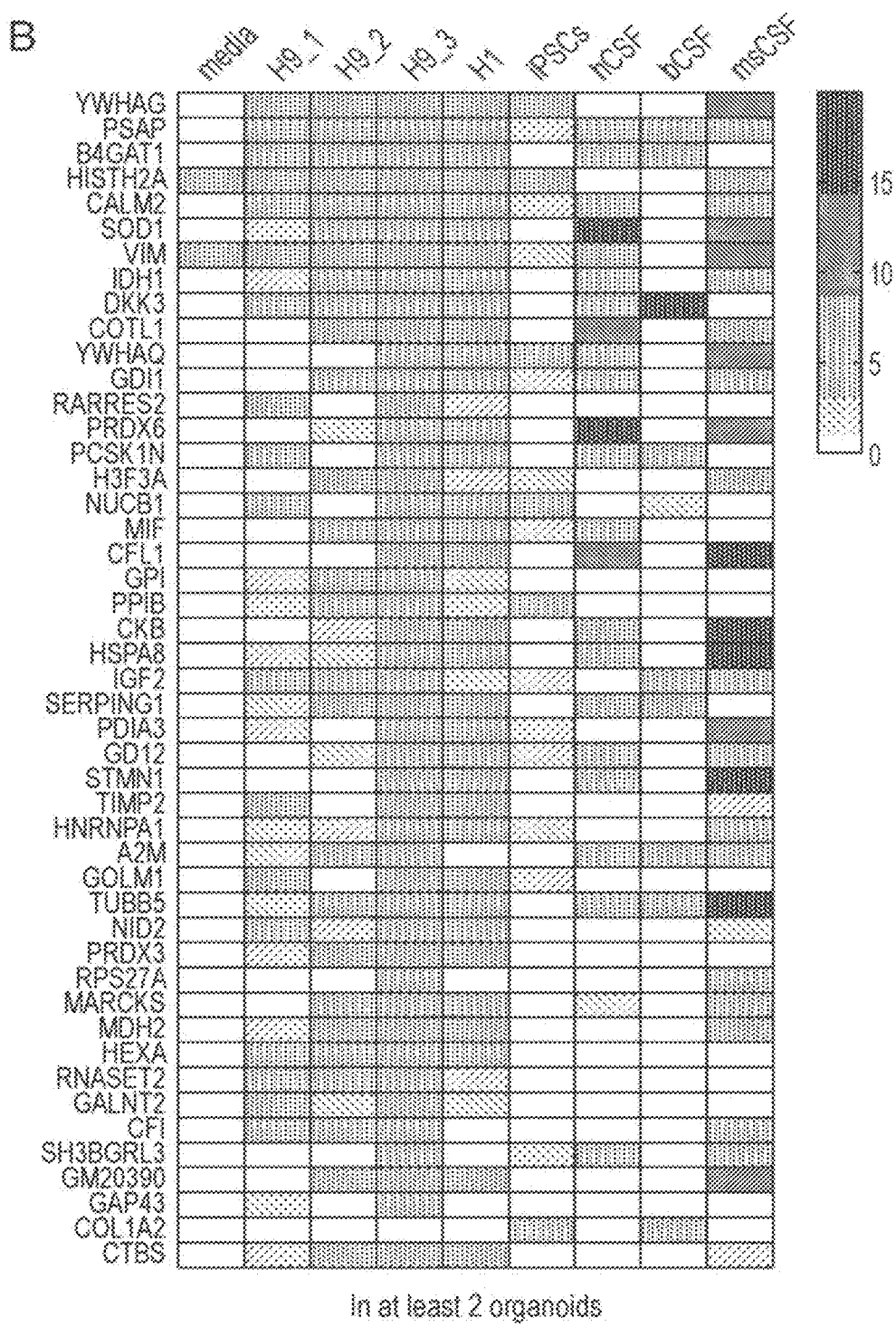
Figure 10:
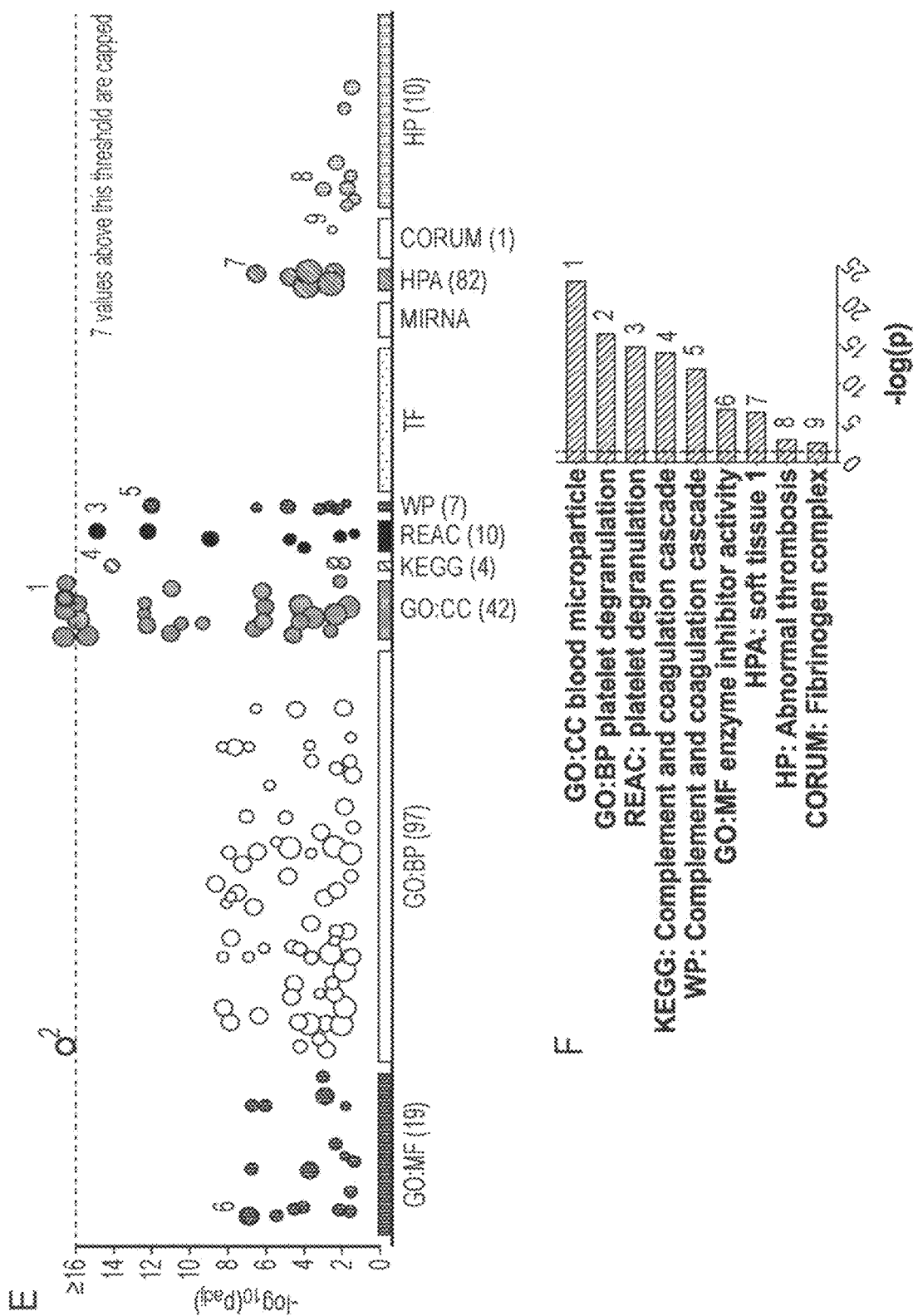

To investigate the composition of this fluid we performed mass spectrometry analysis to compare in vitro organoid CSF-like fluid (iCSF) (3 batches of H9, 1 batch of H1 and 1 batch of iPSCs IMR-90), with 3 different in vivo samples (human adult telencephalic CSF pooled from 3 healthy donors, mouse embryonic CSF at E13.5, and fetal bovine CSF) as well as media. We detected in total 248 abundant proteins in organoid iCSF of which 199 were in common with in vivo CSF samples (FIG. 10A). Gene Ontology Analysis revealed that the GO:CC categories "extracellular vesicle" and "extracellular space", and the GO:BP categories "export from cell" and "secretion from cell" were enriched in the organoid fluid proteome (FIG. 5A). Insulin-like growth factors, particularly IGF2, are secreted by the ChP and regulate cortical progenitor proliferation in developmental CSF (2). Consistent with the role of IGFs in developmental CSF, REAC category "Regulation of Insulin-like Growth Factor" was also significantly enriched in organoid iCSF.

We next focused on proteins detected in at least 2 organoid iCSF samples in order to rule out technical artifacts, and we then examined the most abundant proteins with a reported a emPAI value of 1, based on the number of observed peptides. Of these 83 abundant proteins detected in organoid iCSF, 80 were also detected in in vivo samples, further pointing to a high similarity (FIG. 5B, 10C, 0D). Among these proteins, we detected several biomarkers such as clusterin (CLU), phospholipid transfer protein (PLTP) and apolipoprotein E (APOE) (FIG. 5B, Supplementary Table 1). Many of the proteins detected in iCSF, such as Insulin-like growth factor binding protein 7 (IGFBP7), Serpin Family F Member 1 (SERPINF1), Niemann-Pick disease type C2 protein (NPC2) and retinol-binding protein 1, could also be detected in the scRNA-seq ChP clusters (FIG. 5C, FIG. 5D) further validating their production. A subset of proteins were only present in the human organoid and adult human CSF samples suggesting potentially human-specific secretion (FIG. 5E). We also detected several developmental-specific CSF proteins, including Insulin-like growth factor 2 (IGF2), IGFBP7, and Follistatin-like protein 1 (FSTL1), absent in the adult human sample, indicating that the iCSF secreted by the ChP organoid retains at least some developmental features of human CSF (FIG. 5E). IGF2 levels in organoid fluid were validated by immunoblot (FIG. 5G, FIG. 8C), and immunohistochemistry revealed its presence in the ChP epithelium (FIG. 5H). Consistent with the unique role of ChP in the transport of folate and vitamin C, both vital for brain homeostasis and function (27, 28), we detect enrichment of specific transporters involved in the trafficking of these nutrients: SLC23A2 (vitamin C) and SLC46A2 (folate) in ChP epithelial clusters (FIG. 5D).

We next asked what stage the iCSF from organoids best matches by further comparing with a previously published proteomics dataset of human embryonic Carnegie Stage 20 CSF (29). We could observe a larger overlap of organoid iCSF with the adult CSF, with 121 proteins in common compared to 51 proteins shared between iCSF and embryonic in vivo CSF (FIG. 5E), indicating that iCSF is probably more similar to adult CSF but still retains some developmental features.

Overall, there was very good agreement between the in vitro and the in vivo samples; however, in order to fully ascertain the similarity to in vivo, we further examined the proteins with unusual distributions. First, while the vast majority of proteins detected were not present in the media, pointing to a highly selective barrier, proteomic analysis revealed that of the 14 abundant proteins in the media, 13 were also present in organoid iCSF (FIG. 10C, 10D). Importantly, most of these were also detected in in vivo samples, and included proteins such as albumin (ALB) and transferrin (TF), which are actively transported across the ChP epithelium. Those not detected in vivo are proteins provided by the Matrigel including several laminins. Second, there were several proteins detected reproducibly in the in vivo samples but not in the organoid iCSF that warranted further examination as these could be factors that the organoid failed to properly produce. However, we found that proteins detected exclusively in the in vivo CSF samples but not in the organoid iCSF showed an enrichment in GO:CC "blood microparticle", GO:BP "platelet degranulation" and KEGG: "Complement and coagulation cascade" (FIG. 10B, 10E, 10F). This could be explained by the fact that the invasive procedure of lumbar puncture (spinal tap) CSF collection often results in contamination with peripheral blood and bone marrow. Thus, one of the advantages of the organoid system is that ChP organoids lack the vascular component; therefore, we expect this fluid to be exclusively ChP secretome. Together, these findings suggest that: 1. ChP organoids develop self-contained compartments, distinct from the surrounding media by a tight, epithelial barrier, 2. ChP organoids actively secrete CSF-like fluid enriched in human, developmental-specific CSF proteins, free of blood contaminants.

Figure 6:
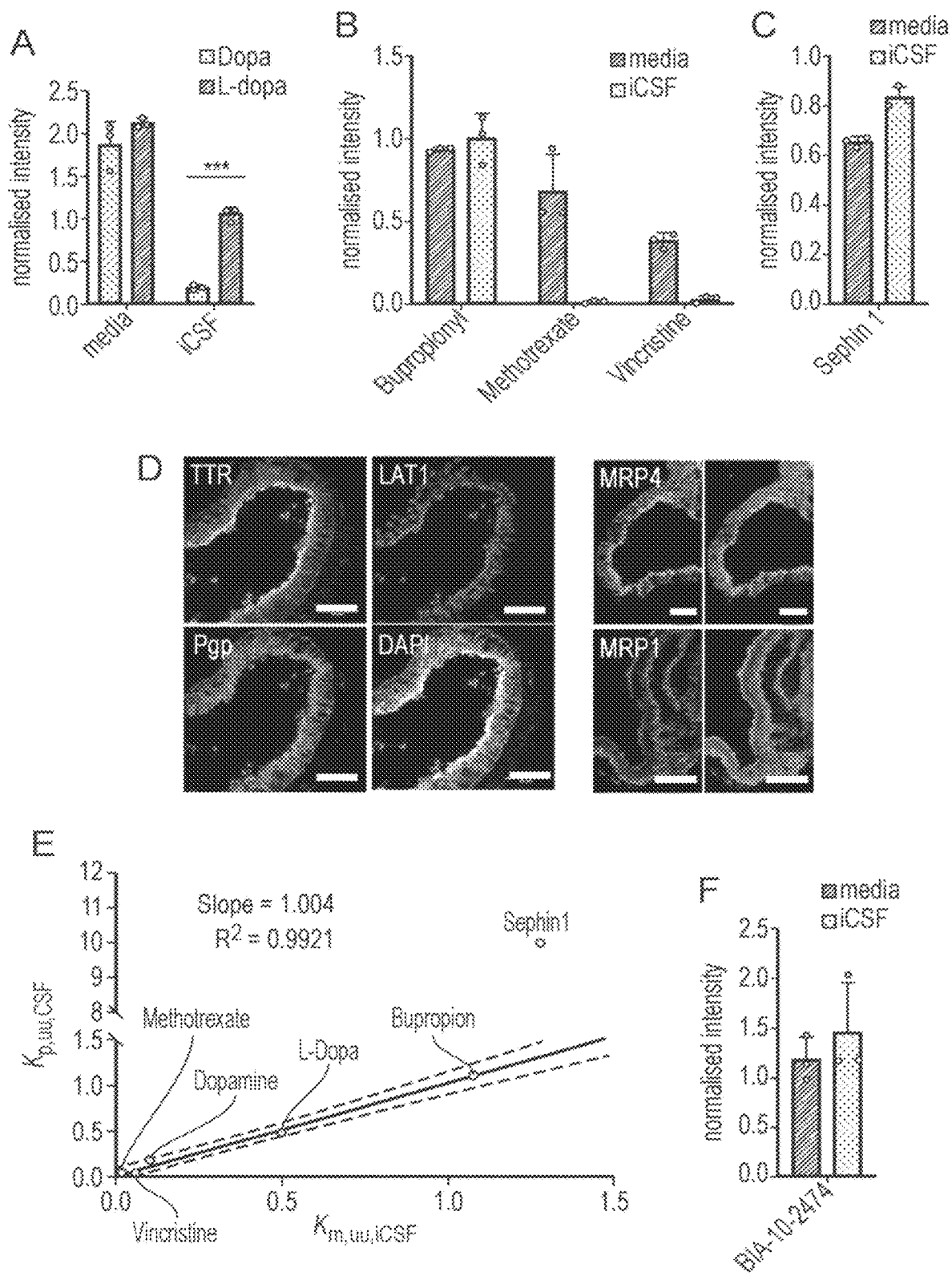
FIG. 6. Choroid plexus organoids model human brain barrier permeability. (A) Relative quantifications of NMR spectra of Dopa and L-Dopa in media and iCSF. (B) Relative NMR spectra quantifications of bupropionyl, methotrexate and vincristine in media and iCSF after 2h incubation. (C) Relative quantifications of NMR spectra of sephin 1 in media and iCSF after 2h incubation. (D) Representative images of ChP epithelium from organoids staining positive for TTR (grey, anti-sheep Alexafluor 647), LAT1 (magenta, anti-mouse Alexafluor 568), Pgp (green, anti-rabbit Alexafluor 488), transporters MRP4 (green, anti-rabbit Alexafluor 488) and MRP1 (green, anti-rabbit Alexafluor 488). Scale bar: 50 µm. Nuclei are labeled in blue with DAPI. (E) Pharmacokinetic model showing correlation ($R^2=0.9921$; Slope=1.004) between in vivo CSF/plasma ratio ($K_{p,uu,CSF}$) and in vitro iCSF/media ratio ($K_{m,uu,iCSF}$) of unbound drugs (Supplementary Table 5). Sephin 1 (red dot) in vivo CSF/plasma measurements are reported in mice to have a much greater value than that detected in human organoids (45). (F) Relative quantifications of NMR spectra of BIA 10-2474 in media and iCSF after 2h incubation. (G) Time course analysis of the ratio of BIA 10-2474 and bupropionyl in iCSF to media at 2 h, 12h, 24 h and 72h. (All drugs were tested in n=3 independent experiments; Supplementary Table 2). (H) Schematic diagram to show that ChP organoids may be exploited as a human in vitro pre-clinical model to predict quantitatively the permeability of unknown compounds and also their dynamics over time.
Figure 6:
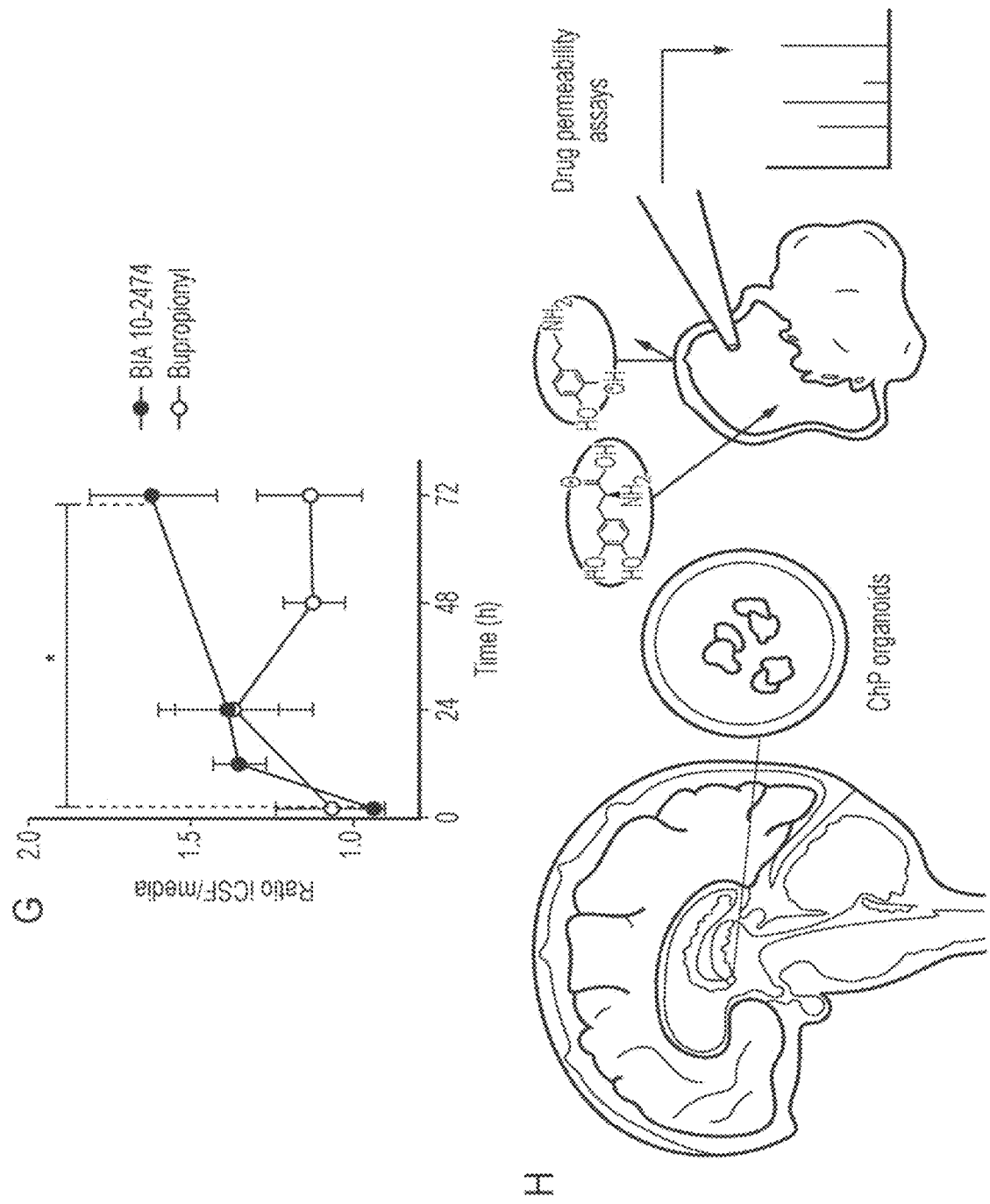

As part of its selective barrier function, the ChP epithelium is also highly selective to small molecules, including therapeutics. Thus, in order to test for such selective permeability to small molecules, we applied various therapeutically relevant small molecules and assayed their permeability by NMR analysis of organoid iCSF. As a proof of principle, we tested the permeability of the barrier to dopamine (Dopa) and its precursor, Levodopa (L-Dopa), since these are highly similar molecules with very different permeability in vivo, and such specificity has not previously been reported in any in vitro models of the BBB. It is well established that Dopa doesn't enter the brain in vivo, whereas L-Dopa is actively transported in to the CSF via the LAT-1 transporter (30-33) and is therefore given as the therapeutic agent in dopamine replacement therapy in patients with Parkinson's disease. We incubated the organoids with Dopa and with L-Dopa in the presence of Carbidopa, a small molecule that prevents the conversion of L-Dopa into Dopa (34, 35). After 2h, we could detect the presence of both L-Dopa and Dopa in the media but only L-Dopa was detectable in the iCSF, consistent with the in vivo properties of a CNS barrier (FIG. 6A, FIG. 11E). L-Dopa iCSF/media ratio was consistently higher compared to Dopa iCSF/media ratio suggesting that our model exhibited the same selectivity to small molecules as in vivo (FIG. 6A).

These findings suggest there may be proper expression of key transporters in the blood-CNS barrier. Indeed, we were able to detect expression of the transporter LAT-1 on the apical side of the ChP organoid epithelium (FIG. 6D, FIG. 9C), which explains the proper transport of L-Dopa seen in our permeability assay. We also stained for the well-known efflux pump P-glycoprotein 1 (Pgp or multidrug resistance protein 1, MDR1), which stops drugs from entering the brain via ATP-dependent mechanisms (36, 37) (FIG. 6D). We detected apical and subapical expression of Pgp, which seemed to localize to intracellular vesicles, in ChP epithelium (FIG. 6D). Pgp localization in ChP has not been well-established (38, 39), however, it is reported to have a role in pumping molecules from the CSF to the blood (38, 40). Additional important efflux transporters in the ChP are MRP1 and MRP4, which prevent toxic compounds and unwanted signals from reaching the CSF (38, 41). MRP1 was both apically and basally localized on the ChP epithelium at 40 days in culture (FIG. 6D, FIG. 9C), while RP4 was apically expressed in ChP epithelium (FIG. 6D). These results suggest that in vitro generated ChP epithelium endogenously expresses transport and export pumps that are critical for the correct function of the B-CSF-B in human brain.

We next tested whether the system could quantitatively predict drug permeability. For this purpose, we performed similar permeability experiments to test bupropionyl, an antidepressant known to readily cross the BBB (42), and two chemotherapeutic compounds, methotrexate and vincristine, which poorly cross the BBB (43, 44). As predicted, bupropionyl was readily detectable in the iCSF after 2h, while methotrexate and vincristine were completely excluded from the iCSF (FIG. 6B). Most importantly, we found a very high correlation between in vitro iCSF/media ratios and the in vivo CSF/plasma ratios reported in the literature for the same drugs ($R^2=0.9921$). Not only that but the actual values corresponded remarkably well (as indicated by a slope of 1.004), indicating that this in vitro system can qualitatively and quantitatively recapitulate the permeability of drugs reported in vivo (FIG. 6E).

These results suggest that the ChP organoid system could be used to model and predict CNS permeability of unknown drugs. To test this theory, we turned to Sephin 1, a novel inhibitor of the regulatory subunit PPP1R15A of protein phosphatase 1, which has been shown to cross the BBB and to have a protective CNS role against protein misfolding in a mouse model of Charcot-Marie Tooth-1B (45). Pre-clinical or clinical data of this molecule in humans are not yet available, but Phase I clinical trials are under way so any additional human in vitro data would be informative. Using the same experimental conditions as previously described, sephin 1 was detectable iCSF after 2h incubation, indicating that this compound could also cross the human CNS barrier (FIG. 6C). Notably, however, the permeability in the human organoid model was much lower than that described in the mouse model, suggesting a higher dose may be needed in humans to achieve the same CNS levels.

Issues related to the pharmacokinetic profile of drugs account for most clinical trial failures (46, 47). One extreme example involved the compound BIA-10-2474, a fatty acid amide hydrolase inhibitor that was in development for treatment of several medical conditions such as chronic pain and multiple sclerosis (48, 49). Sadly, Phase I clinical trials were abruptly halted when six trial participants exhibited severe neurotoxicity, one of whom died (49, 50). Investigations conducted by the French Ministry of Health suggested several possible explanations, one of which was toxic drug accumulation in the brain that was not evident in any animal model tested (49-51). However, because further studies were halted, the exact cause is still unknown. Given the failure to detect such adverse effects in animal models, we sought to test whether the human ChP organoids could potentially more accurately predict human CNS permeability and test the accumulation theory. We compared the pharmacokinetic profile of BIA-10-2474 to a safe compound, bupropionyl, which readily crosses the epithelial barrier but has not been shown to exhibit such toxic accumulation. Similar to bupropionyl, BIA-10-2474 was able to cross the ChP epithelial barrier after 2h incubation (FIG. 6F). However, compared to the bupropionyl, which stabilized to baseline levels after 24h, BIA-10-2474 continued to accumulate in the iCSF (FIG. 6G). These data are consistent with a theory that BIA-10-2474 may have accumulated in the brains of the trial participants, pointing to a potential explanation for why this drug failed in clinical trial. In summary, our findings suggest that the organoid system could be exploited as a human in vitro pre-clinical model to not only predict quantitatively the permeability of unknown compounds, but also their dynamics over time (FIG. 6H).

In conclusion, ChP organoids can be used to study in an unprecedented and reliable manner the development and function of human ChP. This organ is relatively understudied, but is garnering increasing attention due to its important roles in development and diseases such as neurodegeneration.

Supplementary Table 1. ChP organoids secrete human disease-related biomarkers. Table showing the biomarkers detected in iCSF (31 of the 50 most abundant iCSF proteins are shown), the disease or condition in which the biomarker levels are altered and the relevant literature. Asterisks mark the proteins detected also in the media (8-59).

Supplementary Table 2. Time points permeability experiments. Table showing cell line, number of batches, date of collection of the iCSF (DIV) of the relative drugs tested on ChP organoids shown in FIG. 6.

Supplementary Table 3. Time points iCSF for proteomics. Table showing cell line, batches generation date and date of collection of iCSF (DIV) of samples used for proteomic analysis shown in FIG. 5. Asterisk indicates samples pooled together.

Supplementary Table 4. Time points in vivo CSF for proteomics. Table showing type and size of in vivo samples used for proteomic analysis shown in FIG. 5. Asterisk indicates samples pooled together.

Supplementary Table 5. In vivo and in vitro data on drug CSF levels. Table showing measurements of unbound small molecules in CSF and plasma (in vivo) or media (in vitro) and the calculated ratios (K) (60-68).

SUPPLEMENTARY TABLE 1

| Biomarker | Disease/Condition | Reference |
| --- | --- | --- |
| ALB | Barrier integrity | Costa et al. 2018; Lewczuk et al. 2018, Ghasemzadeh et al. 2008 |
| TTR | AD, ALS | Schultz et al. 2010, Ranganathan et al. 2005 |
| TF | Hydrocephalus, prion disorder | Futakawa et al. 2012; Singh et al. 2011 |
| SERPINF1 | AD, dementia | Perrin et al. 2011; Nielsen et al. 2007 |
| IGFBP7 | Ataxia-Telangiectasia (A-T), cognitive impairment | Dzieciatkowska et al. 2011; Poljak et al. 2014 |
| IGFBP2 | AD | Bonham et al. 2018; Äberg et al. 2015 |
| PRDX2 | Vestibular schwannoma | Huang et al. 2019 |
| CLU | Severe Subarachnoid Hemorrhage, AD | Wąsik et al. 2017, Jongbloed et al. 2015 |
| YWHAE | HIV neurocognitive impairment | Morales et al. 2013; Morales et al. 2012 |
| YWHAZ | Spianl cord injury, early multiple sclerosis | Lubieniecka et al. 2011, Martínez-Yélamos et al. 2001 |
| PLTP | MS, AD | Vuletic et al. 2015; Vuletic et al. 2014; Vuletic et al. 2005 |
| B2M | Preterm meningitis, viral meningitis, encephalitis | Muñoz et al. 2019, Svatoňová et al. 2014 |
| CST3 | ALS | Tsuji-Akimoto et al. 2009; Ren et al. 2015 |
| SPARC | AD, central nervous system leukemia | Vafadar-Isfahani et al. 2012; Mo et al. 2019 |
| PKM | AD | Sathe et al. 2018 |
| PGAM1 | AD, Creutzfeldt-Jakob disease | Dayon et al. 2018; Chenet al. 2014 |
| AGP | AD | Quaranta et al. 2019 |
| PFN1 | Neural tube closure defects, cerebral adrenoleukodystrophy | Yan et al. 2017; Orchard et al. 2019 |
| ENPP2 | AD, mild cognitive impairment | McLimans and Willette 201, Heywood et al. 2015; McLimans et al. 2017 |
| LDHA | Meningitis, encephalitis, hydrocephalus | Khosroshahi et al. 2015; Kamat et al. 1999 |
| APOE | AD, MS | Shilde et al. 2018 |
| CA2 | Brain stroke, gliomas | Parkkila et al. 2003; Khwaja et al. 2006 |
| WFIKKN2 | Central nervous system leukemia | Mo et al. 2019; Guo et al. 2015 |
| UCHL1 | Aneurysmal subarachnoid hemorrhage, MS | Lewis et al. 2010; Dobson et al. 2013 |
| BASP1 | Vestibular schwannoma | Huang et al. 2019 |
| TPI1 | Spinal cord injury | Streijger et al. 2017; Albayar et al. 2019 |
| CP | Neurocognitive Impairment, AD | Kessler et al. 2006; Kallianpur et al. 2019 |
| PARK7 | PD | Saito 2017; Parnetti et al. 2013; Hong et al. 2010 |
| TIMP1 | AD, vascular dementia | Bjerke et al. 2011; Duits et al. 2015 |
| CTSD | Spinal cord injury, ALS | Albayar et al. 2019 |
| PTGDS | Meningioma, Schizofrenia | Kim et al. 2012; Martins-De-Souza et al. 2010 |

SUPPLEMENTARY TABLE 2

Time points permeability experiments

| Cell line | Batches | DIV | Drug tested |
| --- | --- | --- | --- |
| H1 | 3 | 48d, 45d, 51d | Dopamine |
| H1 | 3 | 41d, 53d, 54d | Levodopa + carbidopa |
| H1 | 4 | 63d, 39d, 40d | Bupropionyl |
| H1 and H9 | 2 | 66d, 68d | Methotrexate |
| H1 and H9 | 2 | 76d, 80d, 83d | Sephin-1 |
| H1 | 4 | 44d, 46d, 49d | BIA10-2474 |
| H1, H9 | 3 | 42d, 63d, 66d | Vincristine |

SUPPLEMENTARY TABLE 3

Time points iCSF for proteomics

| Cell line | batch generation date | DIV |
| --- | --- | --- |
| H1* | 10 Jul. 2018, 10 Aug. 2018 | 79, 48 |
| H9_1 | 15 Jun. 2018 | 75 |
| H9_2 | 17 Jun. 2018 | 73 |
| H9_3 | 22 Jun. 2018 | 68 |
| iPSCs IMR90-4 | 11 Sep. 2018 | 58 |

SUPPLEMENTARY TABLE 4

Time points in vivo CSF for proteomics

| Sample (in vivo) | Size |
| --- | --- |
| Human adult telencephalic CSF | 3* |
| Mouse embryonic CSF E12.5-13.5 | ~20 (from 2 litters)* |
| Fetal Bovine CSF | 10* |

SUPPLEMENTARY TABLE 5

Comparison drug permeability to in vivo

| Compound | $C_{CSF}$ | In vivo $C_p$ | $f_{u,p}$ | $K_{p,uu,CSF}$ | References | In vitro $K_{m,uu,iCSF}$ |
| --- | --- | --- | --- | --- | --- | --- |
| Methotrexate | 0.27 µM | 15.8 µM | 0.42 | 0.04 | Evans et al. (1983) | 0.01 |
| Bupropion | 7.1 ng/ml | 29.8 ng/ml | 0.21 | 1.11 | Golden et al. (1988) Friden et al. (2009) | 1.07 |

SUPPLEMENTARY TABLE 5-continued

Comparison drug permeability to in vivo

| Compound | $C_{CSF}$ | $C_p$ | In vivo $f_{u, p}$ | $K_{p, uu, CSF}$ | References | In vitro $K_{m, uu, iCSF}$ |
|---|---|---|---|---|---|---|
| Dopamine | 9.01 ng/ml (Δ upon injection) | 67.4 ng/ml | 0.72 | 0.185 | Seri et al. (1984) Onasch et al. (2000) | 0.10 |
| L-DOPA | ~150 ng/ml | ~400 ng/ml | 0.76 | 0.49 | Rizzo et al. (1996) Benetello et al. (1993) | 0.50 |
| Vincristine^ | 0.855 nM | 20.5 nM | — | 0.042 | Jackson el al. (1981) Sethi et al. (1980) | 0.06 |
| Sephin 1* | ~110 ng/g | ~11 ng/ml | — | 10[#] | Das et a. (2015) | 1.28 |

[#]Total compound brain to plasma ratio
^Unbound concentrations reported, average of two measurements
*In vivo data from mouse
Values marked by ~ are estimates from graphs in the relevant references.

All publications mentioned in the above specification are herein incorporated by reference. Various modifications and variations of the disclosed products, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

References for Example 1

1. Lun, M. P., Monuki, E. S. and Lehtinen, M. K. (2015) Development and functions of the choroid plexus-cerebrospinal fluid system. Nat. Rev. Neurosci., 16, 445-457.
2. Lehtinen, M. K. and Walsh, C. A. (2011) Neurogenesis at the Brain-Cerebrospinal Fluid Interface. Annu. Rev. Cell Dev. Biol., 27, 653-679.
3. Silva-Vargas, V., Maldonado-Soto, A. R., Mizrak, D., Codega, P. and Doetsch, F. (2016) Age-Dependent Niche Signals from the Choroid Plexus Regulate Adult Neural Stem Cells. Cell Stem Cell, 19, 643-652.
4. Lun, M. P., Johnson, M. B., Broadbelt, K. G., Watanabe, M., Kang, Y. -j., Chau, K. F., Springel, M. W., Malesz, A., Sousa, A. M. M., Pletikos, M., et al. (2015) Spatially Heterogeneous Choroid Plexus Transcriptomes Encode Positional Identity and Contribute to Regional CSF Production. J. Neurosci., 35, 4903-4916.
5. Ghersi-Egea, J. F., Strazielle, N., Catala, M., Silva-Vargas, V., Doetsch, F. and Engelhardt, B. (2018) Molecular anatomy and functions of the choroidal blood-cerebrospinal fluid barrier in health and disease. Acta Neuropathol., 135, 337-361.
6. Redzic, Z. (2011) Molecular biology of the blood-brain and the blood-cerebrospinal fluid barriers: Similarities and differences. Fluids Barriers CNS, 8, 3.
7. Lancaster, M. and Knoblich, J. A. (2014) Generation of cerebral organoids from human pluripotent stem cells. Nat. Protoc., 9, 2329-2340.
8. Camp, J. G., Badsha, F., Florio, M., Kanton, S., Gerber, T., Wilsch-Brauninger, M., Lewitus, E., Sykes, A., Hevers, W., Lancaster, M., et al. (2015) Human cerebral organoids recapitulate gene expression programs of fetal neocortex development. Proc. Natl. Acad. Sci. U.S.A, 112, 15672-7.
9. Lancaster, M. A., Renner, M., Martin, C., Wenzel, D., Bicknell, L. S., Hurles, M. E., Homfray, T., Penninger, J. M., Jackson, A. P. and Knoblich, J. A. (2013) Cerebral organoids model human brain development and microcephaly. Nature, 501, 373-379.
10. Quadrato, G., Brown, J. and Arlotta, P. (2016) The promises and challenges of human brain organoids as models of neuropsychiatric disease. Nat. Med., 22, 1220-1228.
11. Quadrato, G., Nguyen, T., Macosko, E. Z., Sherwood, J. L., Min Yang, S., Berger, D. R., Maria, N., Scholvin, J., Goldman, M., Kinney, J. P., et al. (2017) Cell diversity and network dynamics in photosensitive human brain organoids. Nature, 545, 48-53.
12. Evolution, H. B., Pollen, A. A., Bhaduri, A., Andrews, M. G., Haussler, D., Eichler, E. E., Kriegstein, A. R., Pollen, A. A., Bhaduri, A., Andrews, M. G., et al. (2019) Establishing Cerebral Organoids as Models of Article Establishing Cerebral Organoids as Models of Human-Specific Brain Evolution. Cell, 176, 743-756.e17.
13. Lancaster, M. A., Corsini, N. S., Wolfinger, S., Gustafson, E. H., Phillips, A. W., Burkard, T. R., Otani, T., Livesey, F. J. and Knoblich, J. A. (2017) Guided self-organization and cortical plate formation in human brain organoids. Nat. Biotechnol., 35, 659-666.
14. Giandomenico, S. L., Mierau, S. B., Gibbons, G. M., Wenger, L. M. D., Masullo, L., Sit, T., Sutcliffe, M., Boulanger, J., Tripodi, M., Derivery, E., et al. (2019) Cerebral organoids at the air-liquid interface generate diverse nerve tracts with functional output. Nat. Neurosci., 22, 669-679.
15. Watanabe, M., Kang, Y.-J., Davies, L. M., Meghpara, S., Lau, K., Chung, C.-Y., Kathiriya, J., Hadjantonakis, A.-K. and Monuki, E. S. (2012) BMP4 Sufficiency to Induce Choroid Plexus Epithelial Fate from Embryonic Stem Cell-Derived Neuroepithelial Progenitors. J. Neurosci., 32, 15934-15945.
16. Sakaguchi, H., Kadoshima, T., Soen, M., Narii, N., Ishida, Y., Ohgushi, M., Takahashi, J., Eiraku, M. and Sasai, Y. (2015) Generation of functional hippocampal neurons from self-organizing human embryonic stem cell-derived dorsomedial telencephalic tissue. Nat. Commun., 6, 1-11.
17. Currie, D. S., Cheng, X., Hsu, C. and Monuki, E. S. (2005) Direct and indirect roles of CNS dorsal midline cells in choroid plexus epithelia formation. Development, 132, 3549-3559.
18. Liddelow, S. A. (2015) Development of the choroid plexus and blood-CSF barrier. Front. Neurosci., 9, 1-13.
19. Lehtinen, M. K., Bjornsson, C. S., Dymecki, S. M., Gilbertson, R. J., Holtzman, D. M. and Monuki, E. S. (2013) The Choroid Plexus and Cerebrospinal Fluid:

Emerging Roles in Development, Disease, and Therapy. *J. Neurosci.*, 33, 17553-17559.
20. Sathyanesan, M., Girgenti, M. J., Banasr, M., Stone, K., Bruce, C., Guilchicek, E., Nairn, A. and Williams, K. (2012) A molecular characterization of the choroid plexus and stress-induced gene regulation. *Transl. Psychiatry*, 2, e139-9.
21. Dani, N., Mccabe, C., Cui, J., Shipley, F. B. and Jang, A. (2019) A cellular and spatial map of the choroid plexus across brain ventricles and ages. *bioRxiv*.
22. Nowakowski, T. J., Bhaduri, A., Pollen, A. A., Alvarado, B., Mostajo-Radji, M. A., Di Lullo, E., Haeussler, M., Sandoval-Espinosa, C., Liu, S. J., Velmeshev, D., et al. (2017) Spatiotemporal gene expression trajectories reveal developmental hierarchies of the human cortex. *Science* (80-.)., 358, 1318-1323.
23. Damkier, H. H., Brown, P. D. and Praetorius, J. (2013) Cerebrospinal Fluid Secretion by the Choroid Plexus. *Physiol. Rev.*, 93, 1847-1892.
24. Neil Dani1*, Rebecca H. Herbst2, 3*, Naomi Habib2, 4*, Head1, J., Dionne2, D., Nguyen2, L., McCabe2, C., Cui1, J., Frederick B. Shipley1,5, Jang1, A., et al. (2019) A cellular and spatial map of the choroid plexus across brain ventricles and ages.
25. Steinemann, A., Galm, I., Chip, S., Nitsch, C. and Reese, T. (2016) Claudin-1, -2 and -3 Are Selectively Expressed in the Epithelia of the Choroid Plexus of the Mouse from Early Development and into Adulthood While Claudin-5 is Restricted to Endothelial Cells. 10, 1-10.
26. Wolburg, H., Wolburg-buchholz, K., Liebner, S. and Engelhardt, B. (2001) Claudin-1, claudin-2 and claudin-11 are present in tight junctions of choroid plexus epithelium of the mouse. 307, 77-80.
27. Wollack, J. B., Makori, B., Ahlawat, S., Koneru, R., Picinich, S. C., Smith, A., Goldman, I. D., Qiu, A., Cole, P. D., Glod, J., et al. (2008) Characterization of folate uptake by choroid plexus epithelial cells in a rat primary culture model. 10.1111/j.1471-4159.2007.05095.x.
28. Ulloa, V., Saldivia, N., Ferrada, L., Salazar, K., Martinez, F., Silva-a, C., Magdalena, R., Oviedo, M. J., Montecinos, H., Torres-vergara, P., et al. (2019) Basal Sodium-Dependent Vitamin C Transporter 2 polarization in choroid plexus explant cells in normal or scorbutic conditions. 10.1038/s41598-019-50772-2.
29. Zappaterra, M. D., Lisgo, S. N., Lindsay, S., Gygi, S. P., Walsh, C. A. and Ballif, B. A. (2007) A comparative proteomic analysis of human and rat embryonic cerebrospinal fluid. *J. Proteome Res.*, 6, 3537-3548.
30. Duelli, R., Enerson, B. E., Gerhart, D. Z. and Drewes, L. R. (2000) Expression of Large Amino Acid Transporter LA T 1 in Rat Brain Endothelium. 37764, 1557-1562.
31. Dickens, D., Chiduza, G. N., Wright, G. S. A., Pirmohamed, M., Antonyuk, S. V and Hasnain, S. S. (2017) Modulation of LAT1 (SLC7A5) transporter activity and stability by membrane cholesterol. *Nat. Publ. Gr.*, 1, 1-13.
32. Uchino, H., Kanai, Y., Kim, D. O. K., Wempe, M. F., Chairoungdua, A., Morimoto, E., Anders, M. W. and Endou, H. (2002) Transport of Amino Acid-Related Compounds Mediated by L-Type Amino Acid Transporter 1 (LAT1): Insights Into the Mechanisms of Substrate Recognition. *Mol. Pharmacol.*, 61, 729-737.
33. Dolgodilina, E., Imobersteg, S., Laczko, E., Welt, T., Verrey, F. and Makrides, V. (2016) Brain interstitial fluid glutamine homeostasis is controlled by blood-brain barrier SLC7A5/LAT1 amino acid transporter. *JCBFM*, 36, 1929-1941.
34. Zhu, H., Lemos, H., Bhatt, B., Islam, B. N., Singh, A., Gurav, A., Huang, L., Browning, D. D., Mellor, A., Fulzele, S., et al. (2017) Carbidopa, a drug in use for management of Parkinson disease inhibits T cell activation and autoimmunity. *PLoS One*, 12, e0183484.
35. Durso, R., Evans, J. E., Josephs, E., Szabo, G., Evans, B., Fernandez, H. H. and Browne, T. R. (2000) Variable Absorption of Carbidopa Affects Both Peripheral and Central Levodopa Metabolism. *J Clin Pharmacol*, 40, 854-860.
36. Assema, D. M. E. Van, Lubberink, M., Boellaard, R., Schuit, R. C., Windhorst, A. D., Scheltens, P., Lammertsma, A. A. and Berckel, B. N. M. Van (2012) P-Glycoprotein Function at the Blood—Brain Barrier: Effects of Age and Gender. *Mol. Imaging Biol.*, 14, 771-776.
37. Schinkel, A. H. (1999) P-Glycoprotein, a gatekeeper in the blood-brain barrier. *Adv. Drug Deliv. Rev.*, 36, 179-194.
38. Vallabhaneni V. Rao, Julie L. Dahlheimer, Mark E. Bardgett, Abraham Z. Snyder, Rick A. Finch, Alan C. Sartorelli, D. P.-W. (1999) Choroid plexus epithelial expression of MDR1 P glycoprotein and multidrug resistance-associated protein contribute to the blood-cerebrospinal-fluid drug-permeability barrier. 96, 3900-3905.
39. Nagaya, Y., Nozaki, Y., Takenaka, O., Watari, R., Kusano, K., Yoshimura, T. and Kusuhara, H. (2016) Drug Metabolism and Pharmacokinetics Investigation of utility of cerebrospinal fluid drug concentration as a surrogate for interstitial fluid concentration using microdialysis coupled with cisternal cerebrospinal fluid sampling in wild-type and Mdr1a (–/–. Drug Metab. *Pharmacokinet.*, 31, 57-66.
40. Ek, C. J., Wong, A., Liddelow, S. A., Johansson, P. A., Dziegielewska, K. M. and Saunders, N. R. (2010) Efflux mechanisms at the developing brain barriers: ABC-transporters in the fetal and postnatal rat. *Toxicol. Lett.*, 197, 51-59.
41. Uchida, Y., Zhang, Z., Tachikawa, M. and Terasaki, T. (2015) Quantitative targeted absolute proteomics of rat blood-cerebrospinal fluid barrier transporters: comparison with a human specimen. *J. Neurochem.*, 134, 1104-1115.
42. Summerfield, S. G., Zhang, Y. and Liu, H. (2016) Examining the Uptake of Central Nervous System Drugs and Candidates across the Blood-Brain Barrier s. *J. Pharmacol. Exp. Ther.*, 358, 294-305.
43. Angelov, L., Doolittle, N. D., Kraemer, D. F., Siegal, T., Barnett, G. H., Peereboom, D. M., Stevens, G., Mcgregor, J., Jahnke, K., Lacy, C. A., et al. (2009) Blood-Brain Barrier Disruption and Intra-Arterial Methotrexate-Based Therapy for Newly Diagnosed Primary CNS Lymphoma: A Multi-Institutional Experience. *J. Clin. Oncol.*, 27, 3503-3509.
44. Zylber-Katz, E., Gomori, J. M., Schwartz, A., Lossos, A., Bokstein, F. and Siegal, T. (2000) Pharmacokinetics of methotrexate in cerebrospinal fluid and serum after osmotic blood-brain barrier disruption in patients with brain lymphoma. *Clin. Pharmacol. Ther.*, 67, 631-641.
45. Das, I., Krzyzosiak, A., Schneider, K., Wrabetz, L., Antonio, M. D., Barry, N., Sigurdardottir, A. and Bertolotti, A. (2015) Preventing proteostasis diseases by selective inhibition of a phosphatase regulatory subunit. 348, 239-243.
46. Wong, C. H. I. H., Siah, K. W. E. I. and Lo, A. W. (2019) Estimation of clinical trial success rates and related. *Biostatistics*, 20, 273-286.

47. Cummings, J. L., Morstorf, T. and Zhong, K. (2014) Alzheimer's disease drug-development pipeline: few candidates, frequent failures. *Alzheimers. Res. Ther.*, 6, 1-7.
48. Otrubova, K., Ezzili, C. and Boger, D. L. (2012) The Discovery and Development of Inhibitors of Fatty Acid Amide Hydrolase (FAAH). *Bioorg. Med. Chem. Lett.*, 21, 4674-4685.
49. Kaur, R., Sidhu, P. and Singh, S. (2016) *What failed BIA 10-2474 Phase I clinical trial? Global speculations and recommendations for future Phase I trials. J. Pharmacol. Pharmacother.*, 7, 120-126.
50. Butler, D. and Callaway, E. (2016) Scientists in the dark after fatal French clinical trial. *Nature*, 529, 236-264.
51. Bird, S. M., Bailey, R. A., SI, M. and Senn, S. (2017) Statistical issues in first-in-human studies on BIA 10-2474: neglected comparison of protocol against practice. *Pharm Stat.*, 16, 100-106.
52. Nicolas, J.-M. (2015) Blood-Brain Barrier in Drug Discovery: Optimizing Brain Exposure of CNS Drugs and Minimizing Brain Side Effects for Peripheral Drugs.
53. Dobson, P. D. and Kell, D. B. (2008) Carrier-mediated cellular uptake of pharmaceutical drugs: an exception or the rule?7

References for Materials and Methods and Supplementary Tables

1. Lancaster, M. and Knoblich, J. A. (2014) Generation of cerebral organoids from human pluripotent stem cells. *Nat. Protoc.*, 9, 2329-2340.
2. Lancaster, M. A., Corsini, N. S., Wolfinger, S., Gustafson, E. H., Phillips, A. W., Burkard, T. R., Otani, T., Livesey, F. J. and Knoblich, J. A. (2017) Guided self-organization and cortical plate formation in human brain organoids. *Nat. Biotechnol.*, 35, 659-666.
3. Nowakowski, T. J., Bhaduri, A., Pollen, A. A., Alvarado, B., Mostajo-radji, M. A., Lullo, E. Di, Haeussler, M., Sandoval-espinosa, C., Liu, S. J., Velmeshev, D., et al. (2017) Spatiotemporal gene expression trajectories reveal developmental hierarchies of the human cortex. 1323, 1318-1323.
4. Lun, M. P., Johnson, M. B., Broadbelt, K. G., Watanabe, M., Kang, Y. -j., Chau, K. F., Springel, M. W., Malesz, A., Sousa, A. M. M., Pletikos, M., et al. (2015) Spatially Heterogeneous Choroid Plexus Transcriptomes Encode Positional Identity and Contribute to Regional CSF Production. *J. Neurosci.*, 35, 4903-4916.
5. Pappin, D. J. C., Creasy, D. M., Cottrell, J. S. and Perkins, D. N. (1999) Probability-based protein identification by searching sequence databases using mass spectrometry data. *Electrophoresis*, 20, 3551-67.
6. Keller, A., Nesvizhskii, A. I., Kolker, E. and Aebersold, R. (2002) Empirical Statistical Model To Estimate the Accuracy of Peptide Identifications Made by MS/MS and Database Search. *Anal. Chem.*, 74, 5383-5392.
7. Fridén, M., Winiwarter, S., Jerndal, G., Bengtsson, O., Hong, W., Bredberg, U., Hammarlund-Udenaes, M. and Antonsson, M. (2009) Structure-brain exposure relationships in rat and human using a novel data set of unbound drug concentrations in brain interstitial and cerebrospinal fluids. *J. Med. Chem.*, 52, 6233-6243.
8. Costa, M., Horrillo, R., Ortiz, A. M., Perez, A., Mestre, A., Ruiz, A., Boada, M. and Grancha, S. (2018) Increased Albumin Oxidation in Cerebrospinal Fluid and Plasma from Alzheimer's Disease Patients. *J. Alzheimer's Dis.*, 63, 1395-1404.
9. Ghasemzadeh, N., Nyberg, F. and Hjerten, S. (2008) Original Paper Highly selective artificial gel antibodies for detection and quantification of biomarkers in clinical samples. II. Albumin in body fluids of patients with neurological disorders. *J Sep Sci*, 31, 3954-3958.
10. Bonham, L. W., Geier, E. G., Steele, N. Z. R., Holland, D., Miller, B. L., Dale, A. M., Desikan, R. S. and Yokoyama, J. S. (2018) Insulin-Like Growth Factor Binding Protein 2 Is Associated With Biomarkers of Alzheimer's Disease Pathology and Shows Differential Expression in Transgenic Mice. *Front. Neurosci.*, 12, 1-10.
11. Äberg, D., Isgaard, J., Wallin, A., Johansson, J.-O., Adreasson, U., Blennow, K., Zetterberg, H., Aberg, N. D. and Svensson, J. (2015) Increased Cerebrospinal Fluid Level of Insulin-like Growth Factor-II in Male Patients with Alzheimer's Disease. *J. Alzheimer's Dis.*, 48, 637-646.
12. Huang, X., Xu, J., Shen, Y., Zhang, L., Xu, M., Chen, M. and Ren, J. (2019) Protein profiling of cerebrospinal fluid from patients undergoing vestibular schwannoma surgery and clinical significance. *Biomed. Pharmacother.*, 116, 108985.
13. Wasik, N., Sokol, B., Holysz, M., Manko, W., Juszkat, R., Jagodzinski, P. P. and Jankowski, R. (2017) Clusterin, a New Cerebrospinal Fluid Biomarker in Severe Subarachnoid Hemorrhage: A Pilot Study. *World Neurosurg.*, 107, 424-428.
14. Jongbloed, W., Dijk, K. D. Van, Mulder, S. D. and Berg, W. D. J. Van De (2015) Clusterin Levels in Plasma Predict Cognitive Decline and Progression to Alzheimer's Disease. *J. Alzheimer's Dis.*, 46, 1103-1110.
15. Morales, D., Hechavarria, R., Wojna, V. and Acevedo, S. F. (2013) YWHAE/14-3-3E: a potential novel genetic risk factor and CSF biomarker for HIV neurocognitive impairment. *J. Neurovirol*, 19, 471-478.
16. Morales, D., Skoulakis, E. C. M. and Acevedo, S. F. (2012) 14-3-3s are potential biomarkers for HIV-related neurodegeneration. *J. Neurovirol*, 18, 341-353.
17. Lubieniecka, J. M., Streijger, F., Lee, J. H. T., Stoynov, N., Liu, J., Mottus, R., Pfeifer, T., Kwon, B. K., Coorssen, J. R., Foster, L. J., et al. (2011) Biomarkers for Severity of Spinal Cord Injury in the Cerebrospinal Fluid of Rats. *PLoS One*, 6, e19247.
18. Martinez-Yélamos, A., Saiz, A., Sanchez-Valle, R., Casado, V., Ramón, J. M., Graus, F., Arbizu, T. and In (2001) 14-3-3 protein in the CSF as prognostic marker in early multiple sclerosis. *Neurology*, 57, 722-725.
19. Vuletic, S., Kennedy, H., Albers, J. J., Killestein, J., Vrenken, H., Lütjohann, D. and Teunissen, C. E. (2014) Cerebrospinal fluid apolipoprotein E and phospholipid transfer protein activity are reduced in multiple sclerosis; relationships with the brain MRI and CSF lipid variables. *Mult. Scler. Relat. Disord.*, 3, 533-541.
20. Ranganathan, S., Williams, E., Ganchev, P., Gopalakrishnan, V., Urbinelli, L., Newhall, K., Cudkowicz, M. E., Jr, R. H. B. and Bowser, R. (2005) Proteomic profiling of cerebrospinal fluid identifies biomarkers for amyotrophic lateral sclerosis. *J Neurochem*, 95, 1461-1471.
21. Vuletic, S., Peskind, E. R., Marcovina, S. M., Quinn, J. F., Cheung, M. C., Kennedy, H., Kaye, J. A., Jin, L. and Albers, J. J. (2005) Reduced CSF PLTP Activity in Alzheimer's Disease and Other Neurologic Diseases; PLTP Induces ApoE Secretion in Primary Human Astrocytes In Vitro. *J. Neurosci. Res.*, 80, 406-413.
22. Batista Muñoz, A., Hadley, S., Sanz, M. I., Quijano, T. A. and Camprubl', M. (2019) Role of beta-2-microglobulin as a biomarker in very preterm and extremely preterm infants with CNS inflammation. *PLoS One.*
23. Svatoňová, J., Bolecká, K., Adam, P. and Lánská, V. (2014) Beta2-Microglobulin as a Diagnostic Marker in Cerebrospinal Fluid: A Follow-Up Study. *Dis. Markers,* 2014, I-6.
24. Tsuji-Akimoto, S., Yabe, I., Niino, M., Kikuchi, S. and Sasaki, H. (2009) Cystatin C in cerebrospinal fluid as a biomarker of ALS. *Neurosci. Lett.,* 452, 52-55.
25. Ren, Y., Zhu, W., Cui, F., Yang, F., Chen, Z., Ling, L. and Huang, X. (2015) Measurement of cystatin C levels in the cerebrospinal fluid of patients with amyotrophic lateral sclerosis. *Int J Clin Exp Pathol,* 8, 5419-5426.
26. Vafadar-Ilsfahani, B., Ball, G., Coveney, C., Lemetre, C., Boocock, D., Minthonc, L., Hanssonc, O., Milesa, A. K., Janciauskienee, S. M., Wardend, D., et al. (2012) Identification of SPARC-like 1 Protein as Part of a Biomarker Panel for Alzheimer's Disease in Cerebrospinal Fluid. *J. Alzheimer's Dis.,* 28, 625-636.
27. Mo, F., Ma, X., Liu, X., Zhou, R., Zhao, Y. and Zhou, H. (2019) Altered CSF Proteomic Profiling of Paediatric Acute Lymphocytic Leukemia Patients with CNS Infiltration. *J. Oncol.,* 2019, 1-8.
28. Sathe, G., Na, C. H., Renuse, S., Madugundu, A. K., Moghekar, A. and Pandey, A. (2018) Quantitative proteomic profiling of cerebrospinal fluid to identify candidate biomarkers for Alzheimer's disease. *Proteomics Clin Appl,* 13, e1800105.
29. Dayon, L., Galindo, A. N., Wojcik, J., Cominetti, O., Corthesy, J., Oikonomidi, A., Henry, H., Kussmann, M., Migliavacca, E., Bowman, G. L., et al. (2018) Alzheimer disease pathology and the cerebrospinal fluid proteome. *Alzheimers. Res. Ther.,* 10, 1-12.
30. Chen, C., Xiao, D., Zhou, W. and Shi, Q. (2014) Global Protein Differential Expression Profiling of Cerebrospinal Fluid Samples Pooled from Chinese Sporadic CJD and non-CJD Patients. *Mol Neurobiol,* 49, 290-302.
31. Schultz, K., Nilsson, K., Nielsen, J. E., Lindquist, S. G., Hjermind, L. E. and Andersen, B. B. (2010) Transthyretin as a potential CSF biomarker for Alzheimer's disease and dementia with Lewy bodies: effects of treatment with cholinesterase inhibitors. *Eur. J. Neurol.,* 17, 456-460.
32. Quaranta, A., Karlsson, i., Ndreu, L., Marini, F., Ingelsson, M. and Thorsen, G. (2019) Glycosylation profiling of selected proteins in cerebrospinal fluid from Alzheimer's disease and healthy subjects. *Anal. Methods,* 11, 3331-3340.
33. Yan, X., Mai, L., Lin, C., He, W. and Yin, G. (2017) CSF-Based Analysis for Identification of Potential Serum Biomarkers of Neural Tube Defects. *Neurosci. Bull.,* 33, 436-444.
34. Orchard, P. J., Nascene, D. R., Gupta, A., Taisto, M. E., Higgins, L., Markowski, T. W. and Lund, T. C. (2019) Cerebral adrenoleukodystrophy is associated with loss of tolerance to profilin. *Eur J Immunol,* 49, 947-953.
35. McLimans, K. E. and Willette, A. A. (2016) Novel CSF Biomarker of Metabolic Dysfunction Predicts AD-like Associations across the Alzheimer's Spectrum. *FASEB J.,* 30, Ib304-Ib304.
36. McLimans, K. E. and Willette, A. A. (2017) Autotaxin is Related to Metabolic Dysfunction and Predicts Alzheimer's Disease Outcomes. *J. Alzheimer's Dis.,* 56, 403-413.
37. Heywood, W. E., Galimberti, D., Bliss, E., Sirka, E., Paterson, R. W., Magdalinou, N. K., Carecchio, M., Reid, E., Heslegrave, A., Fenoglio, C., et al. (2015) Identification of novel CSF biomarkers for neurodegeneration and their validation by a high-throughput multiplexed targeted proteomic assay. *Mol. Neurodegener.,* 10, 1-16.
38. N, K., P, A., M, K., P, S. and K., K. (2015) Spinal Fluid Lactate Dehydrogenase Level Differentiates between Structural and Metabolic Etiologies of Altered Mental Status in Children. *Iran J Child Neurol,* 9, 31-36.
39. Parkkila, A.-K., Parkkila, S., Reunanen, M., Niemela, O., Tuisku, S., Rautakorpi, I. and Rajaniemi, H. (1997) Carbonic anhydrase II in the cerebrospinal fluid: its value as a disease marker. *Eur. J. Clin. Invest.,* 27, 392-397.
40. Guo, Z., Zhang, Y., Zou, L., Wang, D., Shao, C. and Wang, Y. (2015) A Proteomic Analysis of Individual and Gender Variations in Normal Human Urine and Cerebrospinal Fluid Using iTRAQ Quantification. *PLoS One,* 10, 1-17.
41. Lewis, S. B., Wolper, R., Chi, Y., Miralia, L., Wang, Y., Yang, C. and Shaw, G. (2010) Identification and Preliminary Characterization of Ubiquitin C Terminal Hydrolase 1 (UCHL1) as a Biomarker of Neuronal Loss in Aneurysmal Subarachnoid Hemorrhage. *J. Neurosci. Res.,* 88, 1475-1484.
42. Futakawa, S., Nara, K., Miyajima, M., Kuno, A. and Ito, H. (2012) A unique N-glycan on human transferrin in CSF: a possible biomarker for iNPH. *Neurobiol. Aging,* 33, 1807-1815.
43. Dobson, R., Topping, J., Davis, A., Thompson, E. and Giovannoni, G. (2013) Cerebrospinal fluid and urinary biomarkers in multiple sclerosis. *Acta Neurol. Scand.,* 10.1111/ane.12119.
44. Streijger, F., Skinnider, M. A., Rogalski, J. C., Balshaw, R., Shannon, C. P., Prudova, A., Belanger, L., Ritchie, L., Tsang, A., Christie, S., et al. (2017) A Targeted Proteomics Analysis of Cerebrospinal Fluid after Acute Human Spinal Cord Injury. *J. Neurotrauma,* 34, 2054-2068.
45. Albayar, A. A., Roche, A., Swiatkowski, P., Antar, S., Ouda, N., Emara, E., Smith, D. H., Ozturk, A. K. and Awad, B. I. (2019) Biomarkers in Spinal Cord Injury: Prognostic Insights and Future Potentials. *Front. Neurol.,* 10, 1-14.
46. Kessler, H., Pajonk, F., Meisser, P., Hoffmann, K., Supprian, T., Herrmann, W., Obeid, R., Multhaup, G., Falkai, P. and Bayer, T. A. (2006) Cerebrospinal fluid diagnostic markers correlate with lower plasma copper and ceruloplasmin in patients with Alzheimer's disease. *J Neural Transm,* 113, 1763-1769.
47. Kallianpur, A. R., Gittleman, H., Letendre, S., Ellis, R., Bush, W. S. and Heaton, R. (2019) Cerebrospinal Fluid Ceruloplasmin, Haptoglobin, and Vascular Endothelial Growth Factor Are Associated with Neurocognitive Impairment in Adults with HIV Infection. *Mol. Neurobiol.,* 56, 3808-3818.
48. Saito, Y. (2017) DJ-1 as a Biomarker of Parkinson's Disease. In 1037.pp. 149-171.
49. Parnetti, L., Castrioto, A., Chiasserini, D., Persichetti, E., Tambasco, N., El-agnaf, O. and Calabresi, P. (2013) Cerebrospinal fluid biomarkers in Parkinson disease. *Nat. Publ. Gr.,* 9, 131-140.
50. Hong, Z., Shi, Ã. M., Chung, A. K. A., Quinn, J. F., Peskind, E. R., Galasko, D., Jankovic, J., Zabetian, C. P., Leverenz, J. B., Baird, G., et al. (2010) DJ-1 and a-synuclein in human cerebrospinal fluid as biomarkers of Parkinson's disease. *Brain A J. Neurol.,* 133, 713-726.
51. Blennow, K., Wallin, A., Andreasson, U., Bjerke, M. and Zetterberg, H. (2011) Cerebrospinal Fluid Matrix Metalloproteinases and Tissue Inhibitor of Metalloproteinases in Combination with Subcortical and Cortical Biomarkers 52. Duits, F. H., Hernandez-guillamon, M., Montaner, J., Goos, J. D. C., Monta, A., Wattjes, M. P., Barkhof, F., Scheltens, P. and Teunissen, C. E. (2015) Matrix Metalloproteinases in Alzheimer's Disease and Concurrent Cerebral Microbleeds. *J. Alzheimer's Dis.*, 48, 711-720.
53. Singh, A., Beveridge, A. J. and Singh, N. (2011) Decreased CSF Transferrin in sCJD: A Potential Pre-Mortem Diagnostic Test for Prion Disorders. *PLoS One*, 6, e16804.
54. Ho, J. K., Lee, S. K., Yoo, Y. C., Park, N. H., Park, D. B., Yoo, J. S., An, H. J., Park, Y. M. and Gi, K. C. (2012) Proteome analysis of human cerebrospinal fluid as a diagnostic biomarker in patients with meningioma. *Med Sci Monit*, 18, 450-460.
55. Martins-De-Souza, D., Wobrock, T., Zerr, I., Schmitt, A., Gawinecka, J., Schneider-axmann, T., Falkai, P. and Turck, C. W. (2010) Different apolipoprotein E, apolipoprotein A1 and prostaglandin-H2 D-isomerase levels in cerebrospinal fluid of schizophrenia patients. *World J. Biol. Psychiatry*, 11, 719-728.
56. Perrin, R. J., Craig-schapiro, R., Malone, J. P., Shah, A. R., Gilmore, P., Quinn, J. F., Kaye, J. A., Morris, J. C., Holtzman, D. M. and Reid, R. (2011) Identification and Validation of Novel Cerebrospinal Fluid Biomarkers for Staging Early Alzheimer's Disease. *PLoS One*, 6, e16032.
57. Nielsen, H. M., Minthon, L. and Londos, E. (2013) Plasma and CSF serpins in Alzheimer's disease and dementia with Plasma and CSF serpins in Alzheimer disease and dementia with Lewy bodies. *Am. Acad. Neurol.*, 69, 1569-1579.
58. Dzieciatkowska, M., Qi, G., You, J., Bemis, K. G., Sahm, H., Lederman, H. M., Crawford, T. O., Gelbert, L. M., Rothblum-oviatt, C. and Wang, M. (2011) Proteomic Characterization of Cerebrospinal Fluid from Ataxia-Telangiectasia (A-T) Patients Using a LC/MS-Based Label-Free Protein Quantification Technology. *Int. J. Proteomics*, 2011, 1-13.
59. Poljak, A., Hill, M., Hall, R. J., Maclullich, A. M., Raftery, M. J., Tai, J., Yan, S. and Caplan, G. A. (2014) Quantitative proteomics of delirium cerebrospinal fluid. *Transl. Psychiatry*, 4, 1-10.
60. Benetello, P., Furlanut, M., Zara, G., Massimo, B. and Eid Hassan (1993) Plasma Levels of Levodopa and Its Main Metabolites in Parkinsonian Patients after Conventional and Controlled-Release Levodopa-Carbidopa Associations. *Eur. Neurol.*, 33, 69-73.
61. Das, I., Krzyzosiak, A., Schneider, K., Wrabetz, L., Antonio, M. D., Barry, N., Sigurdardottir, A. and Bertolotti, A. (2015) *Preventing proteostasis diseases by selective inhibition of a phosphatase regulatory subunit.* 348, 239-243.
62. Evans, W. E., Hutson, P. R., Stewart, C. D., Cairnes, D. A., Bowman, P. W., Rivera, G. and Crom, W. R. (1983) Methotrexate cerebrospinal fluid and serum concentrations after intermediate-dose methotrexate infusion. *Clin. Pharmacol. Ther.*, 33, 301-307.
63. Golden, R. N., Rudorfer, M. V, Sherer, M. A., Linnoila, M. and Potter, W. Z. (1988) Bupropion in Depression. *Arch Gen Psychiatry*, 45, 139-143.
64. Onash, A., Tanzeen, A., Isgro, F., Boning, D. and Strobel, G. (2000) Effect of intravenous dopamine infusion on plasma concentrations of dopamine and dopamine sulfate in men, during and up to 18 h after infusion. *Eur J Clin Pharmacol.*, 55, 755-759.
65. Rizzo, N., Padoin, C., Palombo, S., Schermann, J.-M. and Girre, C. (1996) Omeprazole and lansoprazole are not inducers of cytochrome P4501A2 under conventional therapeutic conditions. *Eur J Clin Pharmacol.*, 49, 491-495.
66. Seri, I., Tulassay, T., Kiszel, J. and Machay, T. (1984) Cardiovascular response to dopamine in hypotensive preterm neonates.
67. Jackson, D. V, Sethi, V. S., Spurr, C. L. and Mcwhorter, J. M. (1981) Pharmacokinetics of Vincristine in the Cerebrospinal Fluid of Humans1.
68. Jackson, D. V, Sethi, V. S., Long, T. R., Muss, H. B. and Spurr, C. L. (1984) Pharmacokinetics of vindesine bolus and infusion. *Cancer Chemother. Pharmacol.*, 0, 114-119.

The invention claimed is:

1. A choroid plexus organoid comprising:
   (a) an epithelium comprising:
      i) a tight epithelial barrier, and
      ii) apical microvilli; and
   (b) one or more cysts:
      i) surrounded by the epithelium, and
      ii) filled with liquid comprising one or more proteins selected from the group consisting of: transthyretin (TTR), clusterin (CLU), apolipoprotein E (APOE), apolipoprotein A4 (APOA4), lumican (LUM), Serpin Family F Member 1 (SERPINF1), Insulin-like growth factor binding protein 7 (IG-FBP7) secreted protein acidic and rich in cysteine (SPARC), Follistatin-like protein 1 (FSTL1), Insulin-like growth factor binding protein 2 (IGFBP2), phospholipid transfer protein (PLTP), Niemann-Pick disease type C2 protein (NPC2), Fibulin-1 (FBLN1), Ectonucleotide Pyrophosphatase/Phosphodiesterase 2 (ENPP2), Collagen Type I Alpha-1 Chain (COL1A1), Peroxiredoxin-1 (PRDX1), Collagen Type VI Alpha-1 Chain (COL6A1), Cathepsin D (CTSD), Collagen Type I Alpha-2 Chain (COL1A2), Ceruloplasmin (CP) and TIMP metallopeptidase inhibitor 1 (TIMP1).

2. The choroid plexus organoid of claim 1, wherein the epithelium is TTR positive (+), Multidrug resistance-associated protein 1 (MRP1)+, aquaporin 1 (Aqp1)+, and/or zonula occludens (ZO1)+.

3. The choroid plexus organoid of claim 2, wherein the TTR, Aqp1, and/or ZO1 are enriched on an apical side of the epithelium.

4. The choroid plexus organoid of claim 2, wherein the MRP1 is enriched on an apical side of the epithelium and a basal side of the epithelium.

5. The choroid plexus organoid of claim 1, which further comprises (c) stromal cells.

6. The choroid plexus organoid of claim 1, which is a lateral ventricle choroid plexus organoid.

7. The choroid plexus organoid of claim 1 wherein the epithelium comprises primary cilia.

* * * * *

SEQUENCE LISTING

```
<160> NUMBER OF SEQ ID NOS: 1

<210> SEQ ID NO 1
<211> LENGTH: 408
<212> TYPE: PRT
<213> ORGANISM: Homo sapiens
<220> FEATURE:
<223> OTHER INFORMATION: Homo sapiens Bmp4

<400> SEQUENCE: 1

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
```

-continued

```
                        85                  90                  95
Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
            130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
                195                 200                 205

Val Thr Arg Trp Glu Thr Phe Asp Val Ser Pro Ala Val Leu Arg Trp
            210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
                275                 280                 285

Arg Ala Lys Arg Ser Pro Lys His His Ser Gln Arg Ala Arg Lys Lys
            290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
                340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
            370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```